(12) United States Patent
Qin et al.

(10) Patent No.: US 10,106,591 B2
(45) Date of Patent: *Oct. 23, 2018

(54) BMP PEPTIDES AND METHODS OF USE

(71) Applicant: LifeNet Health, Virginia Beach, VA (US)

(72) Inventors: Xiaofei Qin, Virginia Beach, VA (US); Silvia Chen, Virginia Beach, VA (US); Jingsong Chen, Virginia Beach, VA (US); James Clagett, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/690,418

(22) Filed: Aug. 30, 2017

(65) Prior Publication Data

US 2017/0369546 A1    Dec. 28, 2017

Related U.S. Application Data

(63) Continuation of application No. 14/342,561, filed as application No. PCT/US2012/053584 on Sep. 2, 2012.

(60) Provisional application No. 61/530,727, filed on Sep. 2, 2011, provisional application No. 61/530,706, filed on Sep. 2, 2011, provisional application No. 61/530,715, filed on Sep. 2, 2011, provisional application No. 61/536,035, filed on Sep. 18, 2011.

(51) Int. Cl.
*C07K 14/51*   (2006.01)
*A61K 38/48*   (2006.01)
*C12N 5/077*   (2010.01)
*A61K 38/18*   (2006.01)

(52) U.S. Cl.
CPC .......... *C07K 14/51* (2013.01); *A61K 38/1875* (2013.01); *A61K 38/4826* (2013.01); *A61K 38/4873* (2013.01); *A61K 38/4886* (2013.01); *C12N 5/066* (2013.01); *C12N 5/0654* (2013.01); *C12N 5/0655* (2013.01); *C12Y 304/21004* (2013.01); *C12Y 304/22008* (2013.01); *C12Y 304/22038* (2013.01); *C12Y 304/24004* (2013.01); *C12Y 304/24007* (2013.01); *C12Y 304/24019* (2013.01); *C07K 2319/00* (2013.01); *C07K 2319/23* (2013.01); *C07K 2319/24* (2013.01); *C07K 2319/50* (2013.01); *C07K 2319/705* (2013.01); *C12N 2501/155* (2013.01)

(58) Field of Classification Search
None
See application file for complete search history.

(56) References Cited

U.S. PATENT DOCUMENTS

| | | |
|---|---|---|
| 5,770,444 A | 6/1998 | Lee et al. |
| 5,821,056 A | 10/1998 | Lee |
| 7,198,790 B2 | 4/2007 | Lee et al. |
| 2001/0018509 A1 | 8/2001 | Lee et al. |
| 2002/0165361 A1 | 11/2002 | Lee et al. |
| 2005/0136042 A1 | 6/2005 | Betz et al. |
| 2006/0280768 A1 | 12/2006 | Hwang et al. |
| 2009/0017045 A1 | 1/2009 | Lee et al. |
| 2009/0298761 A1 | 12/2009 | Engelman |

FOREIGN PATENT DOCUMENTS

| | | | |
|---|---|---|---|
| EP | 1571159 A1 | | 9/2005 |
| WO | 96/26737 A1 | | 9/1996 |
| WO | 2004/084949 A2 | | 10/2004 |
| WO | WO2008/039525 | * | 8/2008 |
| WO | 2009/102966 A2 | | 8/2009 |
| WO | WO 2010/090523 A1 | | 8/2010 |
| WO | 2011/020115 A2 | | 2/2011 |
| WO | 2011/119833 A2 | | 9/2011 |

OTHER PUBLICATIONS

A0A091TMQ7_9AVES (UniProt accessed Oct. 25, 2017) (Year: 2017).*
Li et al., Molecular Human Reproduction, 15(12):779-88 (2009).
European Office Action for European Patent Application No. 12828239. 9, dated Jan. 26, 2016.
European Communication for European Application No. 12 828 239.9, dated Mar. 7, 2017, 4 pages.
International Search Report issued in corresponding International Patent Application No. PCT/US2012/53584 dated Feb. 5, 2013.
Extended European Search Report issued in corresponding European Patent Application No. 12828239.9 dated Jan. 30, 2015.
Wu et al., "Proteolysis Involving Matrix Metalloproteinase 13 (Collagenase-3) is Required for Chondrocyte Differentiation That is Associated with Matrix Mineralization," Journal of Bone and Mineral Research, 17: 639-651 (2002).
International Preliminary Report on Patentability and Written Opinion issued in corresponding International Patent Application No. PCT/US2012/53584 dated Mar. 4, 2014.
Nickel et al., Journal of Bone and Joint Surgery, vol. 83-A Supplement 1, Part 1, pp. S1-7-S1-14 (2001).

\* cited by examiner

*Primary Examiner* — James H Alstrum-Acevedo
*Assistant Examiner* — Tara L Martinez
(74) *Attorney, Agent, or Firm* — RatnerPrestia

(57) ABSTRACT

The invention relates to truncated growth factors and variants thereof. The invention also relates to methods of making and using the truncated growth factors. The invention further relates to compositions including a protease and a growth factor comprising a bone morphogenic protein (BMP) or a variant thereof. The invention also relates to methods of using the composition.

19 Claims, 17 Drawing Sheets

Specification includes a Sequence Listing.

BMP2 Control (Residues 283-396 of SEQ ID NO: 1)
Trypsin truncated BMP2 (SEQ ID NO: 16)

BMP2 Control (Residues 283-396 of SEQ ID NO: 1)
Collagenase truncated BMP2 (SEQ ID NO: 18)

BMP2 control (Residues 283-396 of SEQ ID NO: 1)
Modified BMP2 (SEQ ID NO: 18)

BMP2 control (Residues 283-396 of SEQ ID NO: 1)
Modified BMP2 (SEQ ID NO: 18)

BMP4 Control (Residues 293-408 of SEQ ID NO: 3)
Modified BMP4 (SEQ ID NO: 19)

BMP5 (Residues 317-454 of SEQ ID NO: 4)
Dispase-modified BMP5 (SEQ ID NOs: 20-28)

BMP5 Control (Residues 317-454 of SEQ ID NO: 4)
Collagenase-modified BMP5 (SEQ ID NOs: 20-28)

Modified rhBMP5 (SEQ ID NOs: 20-28)

BMP7 control (Residues 293-431 of SEQ ID NO: 6)
Collagenase truncated BMP7 (SEQ ID NO: 31)

rhBMP7 Control (Residues 293-431 of SEQ ID NO: 6)
Modified rhBMP7 (SEQ ID NO: 31)

BMP7 control (Residues 293-431 of SEQ ID NO: 6)
Trypsin Modified BMP7 (SEQ ID NO: 30)

rhBMP7 control (Residues 293-431 of SEQ ID NO: 6)
Dispase-treated BMP7 (SEQ ID NO: 31)

rhGDF-6 (Residues 336-455 of SEQ ID NO: 12)
Dispase-modified rhGDF-6 (SEQ ID NO: 34)

GDF-6 control (Residues 336-455 of SEQ ID NO: 12)
Collagenase-modified GDF-6 (SEQ ID NO: 34)

GDF5 control (Residues 382-501 of SEQ ID NO: 13)
Dispase modified GDF5 (SEQ ID NO: 35)

Modified rhBMP14 (SEQ ID NO: 35)

Dispase-treated rhBMP14 (SEQ ID NO: 35)

BMP PEPTIDES AND METHODS OF USE

CROSS-REFERENCE TO RELATED APPLICATIONS

This application is a continuation of U.S. application Ser. No. 14/342,561, filed Nov. 18, 2014, which is a U.S. National Phase Application of International Application No. PCT/US2012/053584, filed Sep. 2, 2012, which claims priority to U.S. Provisional Application Nos. 61/530,706, 61/530,715, 61/530,727, and 61/536,035, filed Sep. 2, 2011, Sep. 2, 2011, Sep. 2, 2011, and Sep. 18, 2011, respectively, all of which are incorporated herein by reference in their entireties.

BACKGROUND OF THE INVENTION

The invention relates to truncated growth factors and variants thereof. The invention also relates to methods of making and using the truncated growth factors.

The invention relates to compositions including a protease and a growth factor comprising a bone morphogenic protein (BMP) or a variant thereof. The invention also relates to methods of using the composition.

SUMMARY OF THE INVENTION

The invention relates to isolated peptides of 137 residues or less, with the peptide comprising an amino acid sequence at least 95% identical to the amino acid sequence of SEQ ID NO:20, 21, 22, 23, 24, 25, 26, 27 or 28.

The invention relates to isolated peptides of 119 residues or less, with the peptide comprising an amino acid sequence at least 95% identical to the amino acid sequence of SEQ ID NO:34.

The invention relates to isolated peptides of 119 residues or less, with the peptide comprising an amino acid sequence at least 95% identical to the amino acid sequence of SEQ ID NO:35.

The invention also relates to fusion proteins comprising the inventive peptides described herein fused to a second peptide, wherein the second peptide comprises an amino acid sequence that is less than 70% identical to the amino acid sequence of SEQ ID NO:40, 41, 42, 43, 44, 45, 46, 47, 48, 54, or 55.

The invention also relates to methods of promoting osteoinductive, chondroinductive, ligament differentiating, and/or tendon differentiating activity, with the methods comprising contacting cells with the inventive peptides described herein.

The invention also relates to methods of administering the inventive peptides described herein to matrices.

The invention also relates to methods of increasing osteogenesis, chondrogenesis, or ligament/tendon genesis in cells comprising administering to the cells the inventive peptides described herein.

The invention also relates to methods of increasing a cellular growth factor activity comprising administering to the cells at least one protease and the growth factor comprising SEQ ID NO: 20, 21, 22, 23, 24, 25, 26, 27, 28, 34 or 35. In some embodiments, the composition comprises two or more proteases.

The invention relates to compositions comprising at least one protease and a growth factor, wherein the growth factor is (i) a bone morphogenic protein (BMP) or (ii) an isolated peptide comprising an amino acid sequence at least 92% identical to any of amino acid sequences of SEQ ID NO: 16-35, wherein the peptide has osteoinductive, chondroinductive, or ligament/tendon differentiating activity. In some embodiments, the composition comprises two or more proteases.

The invention also relates to methods of increasing a growth factor activity comprising administering to the cells the composition described herein.

DETAILED DESCRIPTION OF THE INVENTION

Figure 1:
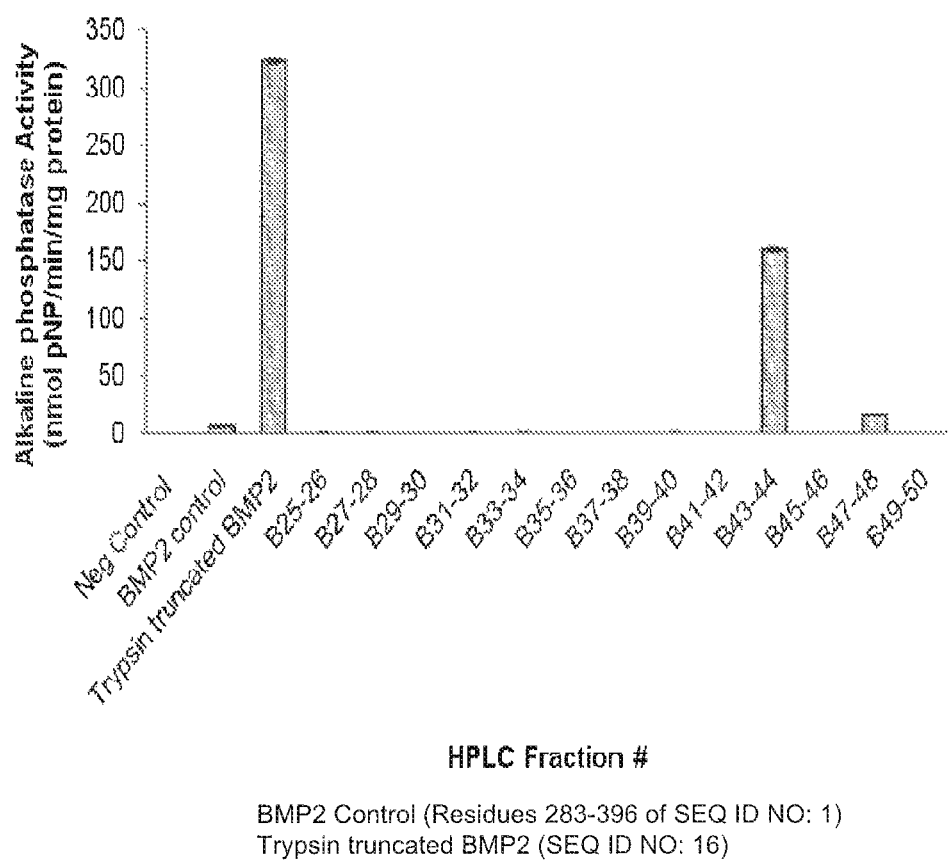
FIG. 1 depicts myoblast expression of alkaline phosphatase after being cultured with rhBMP-2 modified with trypsin. Myoblasts treated with rhBMP-2 modified with trypsin showed significantly greater alkaline phosphatase activity over myoblasts treated with unmodified rhBMP-2.

The invention relates to compositions comprising at least one protease and a growth factor comprising a bone morphogenic protein (BMP) or a variant thereof. In some embodiments, the growth factors are bone morphogenic proteins ("BMP," "hBMP," or "rhBMP"). The term "bone morphogenetic protein" refers to a protein belonging to the BMP family of the TGF-β superfamily of proteins (BMP family) based on DNA and amino acid sequence homology. A protein belongs to the BMP family according to this invention when it has at least 50% amino acid sequence identity with at least one known BMP family member within the conserved C-teiminal cysteine-rich domain which characterizes the BMP protein family. Members of the BMP family may have less than 50% DNA or amino acid sequence identity overall. Examples of BMPs include, but are not limited to, BMP-2, BMP-3, BMP-4, BMP-5, BMP-6, BMP-7, BMP-8, BMP-9, BMP-10, BMP-11, BMP-12, BMP-13, BMP-14, BMP-15, and BMP-16, e.g., amino acid sequences of SEQ ID NO:1-15, respectively. In further embodiments, the growth factors are isolated peptides comprising mature peptide sequences of the BMPs. In additional embodiments, the growth factors are isolated peptides comprising modified growth factors described below. In yet additional embodiments, the growth factors are fusion proteins comprising the modified growth factors described herein fused to a second peptide, wherein the second peptide comprises an amino acid sequence that is less than 70% identical to the amino acid sequences of SEQ ID NO: 36-55.

In some embodiments, the BMPs used in the present invention expressly exclude BMP-2, BMP-4, BMP-5, BMP-7, BMP-13, and BMP-14. In some embodiments, the BMPs used in the present invention expressly exclude BMP-2, BMP-4 and BMP-7.

In one specific embodiment, the composition of the present invention comprises at least one protease and a growth factor, wherein the growth factor is a bone morphogenic protein (BMP), wherein the BMP is not BMP-2, BMP-4, BMP-5, BMP-7, BMP-13, or BMP-14. In further embodiments, the method of the present invention comprise treating a cell with the composition comprising at least one protease and a growth factor, wherein the growth factor is a bone morphogenic protein (BMP), wherein the BMP is not BMP-2, BMP-4, BMP-5, BMP-7, BMP-13, or BMP-14. In the embodiments where the BMP is not BMP-2, BMP-4, BMP-5, BMP-7, BMP-13, or BMP-14, the composition optionally comprises two or more proteases, the protease is optionally selected from the group consisting of collagenase, clostripain, dispase, trypsin, cathepsin, BMP-1 (bone morphogenetic protein-1), MMP-13 (matrix metalloproteinase-13), and a mixture thereof, the protease is optionally collagenase or dispase.

In another specific embodiment, the composition of the present invention comprises at least one protease and a growth factor, wherein the growth factor is a bone morphogenic protein (BMP), wherein the BMP is not BMP-2, BMP-4 or BMP-7. In further embodiments, the method of the present invention comprise treating a cell with the composition comprising at least one protease and a growth factor, wherein the growth factor is a bone morphogenic protein (BMP), wherein the BMP is not BMP-2, BMP-4 or BMP-7. In the embodiments where the BMP is not BMP-2, BMP-4 or BMP-7, the composition optionally comprises two or more proteases, the protease is optionally selected from the group consisting of collagenase, clostripain, dispase, trypsin, cathepsin, BMP-1 (bone morphogenetic protein-1), MMP-13 (matrix metalloproteinase-13), and a mixture thereof, the protease is optionally collagenase or dispase.

In another specific embodiment, the composition of the present invention comprises at least one protease and a growth factor, wherein the growth factor is a bone morphogenic protein (BMP), wherein the BMP does not have any amino acid sequence of residue 283-396 of SEQ ID NO: 1, residue 293-408 of SEQ ID NO: 3, residue 317-454 of SEQ ID NO: 4, residue 293-431 of SEQ ID NO: 6, and residue 336-455 of SEQ ID NO: 12, and residue 382-501 of SEQ ID NO: 13. In further embodiments, the method of the present invention comprise treating a cell with the composition comprising at least one protease and a growth factor, wherein the growth factor is a bone morphogenic protein (BMP), wherein the BMP does not have any amino acid sequence of residue 283-396 of SEQ ID NO: 1, residue 293-408 of SEQ ID NO: 3, residue 317-454 of SEQ ID NO: 4, residue 293-431 of SEQ ID NO: 6, residue 336-455 of SEQ ID NO: 12, and residue 382-501 of SEQ ID NO: 13. In the embodiments where the BMP does not have any amino acid sequence of 283-396 of SEQ ID NO: 1, residue 293-408 of SEQ ID NO: 3, residue 317-454 of SEQ ID NO: 4, residue 293-431 of SEQ ID NO: 6, residue 336-455 of SEQ ID NO: 12, and residue 382-501 of SEQ ID NO: 13, the composition optionally comprises two or more proteases, the protease is optionally selected from the group consisting of collagenase, clostripain, dispase, trypsin, cathepsin, BMP-1 (bone morphogenetic protein-1), MMP-13 (matrix metalloproteinase-13), and a mixture thereof, the protease is optionally collagenase or dispase.

In another specific embodiment, the composition of the present invention comprises at least one protease and a growth factor, wherein the growth factor is a bone morphogenic protein (BMP), wherein the BMP does not have any amino acid sequence of residue 283-396 of SEQ ID NO: 1, residue 293-408 of SEQ ID NO: 3, and residue 293-431 of SEQ ID NO: 6. In further embodiments, the method of the present invention comprise treating a cell with the composition comprising at least one protease and a growth factor, wherein the growth factor is a bone morphogenic protein (BMP), wherein the BMP does not have any amino acid sequence of residue 283-396 of SEQ ID NO: 1, residue 293-408 of SEQ ID NO: 3, and residue 293-431 of SEQ ID NO: 6. In the embodiments where the BMP does not have any amino acid sequence of residue 283-396 of SEQ ID NO: 1, residue 293-408 of SEQ ID NO: 3, and residue 293-431 of SEQ ID NO: 6, the composition optionally comprises two or more proteases, the protease is optionally selected from the group consisting of collagenase, clostripain, dispase, trypsin, cathepsin, BMP-1 (bone morphogenetic protein-1), MMP-13 (matrix metalloproteinase-13), and a mixture thereof, the protease is optionally collagenase or dispase.

In another specific embodiment, the composition of the present invention comprises at least one protease and a growth factor, wherein the growth factor is a bone morphogenic protein (BMP), wherein the BMP does not have any amino acid sequence of SEQ ID NO: 1, 3, 4, 6, 12, and 13. In further embodiments, the method of the present invention comprise treating a cell with the composition comprising at least one protease and a growth factor, wherein the growth factor is a bone morphogenic protein (BMP), wherein the BMP does not have any amino acid sequence of SEQ ID NO: 1, 3, 4, 6, 12, and 13. In the embodiments where the BMP does not have any amino acid sequence of SEQ ID NO: 1, 3, 4, 6, 12, and 13, the composition optionally comprises two or more proteases, the protease is optionally selected from the group consisting of collagenase, clostripain, dispase, trypsin, cathepsin, BMP-1 (bone morphogenetic protein-1), MMP-13 (matrix metalloproteinase-13), and a mixture thereof, the protease is optionally collagenase or dispase.

In another specific embodiment, the composition of the present invention comprises at least one protease and a growth factor, wherein the growth factor is a bone morphogenic protein (BMP), wherein the BMP does not have any amino acid sequence of SEQ ID NO: 1, 3 and 6. In further embodiments, the method of the present invention comprise treating a cell with the composition comprising at least one protease and a growth factor, wherein the growth factor is a bone morphogenic protein (BMP), wherein the BMP does not have any amino acid sequence of SEQ ID NO: 1, 3 and 6. In the embodiments where the BMP does not have any amino acid sequence of SEQ ID NO: 1, 3 and 6, the composition optionally comprises two or more proteases, the protease is optionally selected from the group consisting of collagenase, clostripain, dispase, trypsin, cathepsin, BMP-1 (bone morphogenetic protein-1), MMP-13 (matrix metalloproteinase-13), and a mixture thereof, the protease is optionally collagenase or dispase.

In another specific embodiment, the composition of the present invention comprises at least one protease and a growth factor, wherein the growth factor is a bone morphogenic protein (BMP), wherein the BMP does not have any amino acid sequence of SEQ ID NO: 16-28 and 30-35. In further embodiments, the method of the present invention comprise treating a cell with the composition comprising at least one protease and a growth factor, wherein the growth factor is a bone morphogenic protein (BMP), wherein the BMP does not have any amino acid sequence of SEQ ID NO: 16-28 and 30-35. In the embodiments where the BMP does not have any amino acid sequence of SEQ ID NO: 16-28 and 30-35, the composition optionally comprises two or more proteases, the protease is optionally selected from the group consisting of collagenase, clostripain, dispase, trypsin, cathepsin, BMP-1 (bone morphogenetic protein-1), MMP-13 (matrix metalloproteinase-13), and a mixture thereof, the protease is optionally collagenase or dispase.

In another specific embodiment, the composition of the present invention comprises at least one protease and a growth factor, wherein the growth factor is a bone morphogenic protein (BMP), wherein the BMP does not have any amino acid sequence of SEQ ID NO: 16-19 and 30-33. In further embodiments, the method of the present invention comprise treating a cell with the composition comprising at least one protease and a growth factor, wherein the growth factor is a bone morphogenic protein (BMP), wherein the BMP does not have any amino acid sequence of SEQ ID NO: 16-19 and 30-33. In the embodiments where the BMP does not have any amino acid sequence of SEQ ID NO: 16-19 and 30-33, the composition optionally comprises two or more proteases, the protease is optionally selected from the group consisting of collagenase, clostripain, dispase, trypsin, cathepsin, BMP-1 (bone morphogenetic protein-1), MMP-13 (matrix metalloproteinase-13), and a mixture thereof, the protease is optionally collagenase or dispase.

The terms "peptide," "polypeptide" and "protein" are used interchangeably herein. As used herein, an "isolated polypeptide" is intended to mean a polypeptide that has been completely or partially removed from its native environment. For example, polypeptides that have been removed or purified from cells are considered isolated. In addition, recombinantly produced polypeptides molecules contained in host cells are considered isolated for the purposes of the present invention. Moreover, a peptide that is found in a cell, tissue or matrix in which it is not normally expressed or found is also considered as "isolated" for the purposes of the present invention. Similarly, polypeptides that have been synthesized are considered to be isolated polypeptides. "Purified," on the other hand is well understood in the art and generally means that the peptides are substantially free of cellular material, cellular components, chemical precursors or other chemicals beyond, perhaps, buffer or solvent. "Substantially free" is not intended to mean that other components beyond the novel peptides are undetectable. The peptides of the present invention may be isolated or purified.

The amino acid sequences of SEQ ID NO:1-15 represent the full length "prepropeptide" of some exemplary BMPs, BMP-2-16, respectively. In some embodiments, the BMP is formed as a full length prepropeptide, which usually contains, from N-terminus to C-terminus, a signal sequence, a propeptide domain and the "mature" peptide. Table 1 shows exemplary BMP sequences and the "mature" peptide sequences in the sequences.

TABLE 1

Mature peptide sequences in various types of BMPs.

| Type of BMP | Genbank Accession No. or UniProt Accession No. | Mature Peptide |
|---|---|---|
| BMP-2 | NP_001191 | residue 283-396 of SEQ ID NO: 1 |
| BMP-3 | P12645 | residue 363-472 of SEQ ID NO: 2 |
| BMP-4 | P12644 | residue 293-408 of SEQ ID NO: 3 |
| BMP-5 | NP_066551 | residue 317-454 of SEQ ID NO: 4 |
| BMP-6 | P22004 | residue 375-513 of SEQ ID NO: 5 |
| BMP-7 | P18075 | residue 293-431 of SEQ ID NO: 6 |
| BMP-8 | P34820 | residue 243-402 of SEQ ID NO: 7 |
| BMP-9 | Q9UK05 | residue 319-429 of SEQ ID NO: 8 |
| BMP-10 | O95393 | residue 316-424 of SEQ ID NO: 9 |
| BMP-11 | O95390 | residue 298-407 of SEQ ID NO: 10 |
| BMP-12 | P43029 | residue 316-461 of SEQ ID NO: 11 |
| BMP-13 | NP_001001557 | residue 336-455 of SEQ ID NO: 12 |
| BMP-14 | NP_000548 | residue 382-501 of SEQ ID NO: 13 |
| BMP-15 | O95972 | residue 267-392 of SEQ ID NO: 14 |
| BMP-16 | AAO31471 | residue 171-280 of SEQ ID NO: 15 |

Normally, the BMP family of growth factors is translated into the full length prepropeptide. Through subsequent post-translational processing, the signal peptide and the propeptide domains are cleaved with the remaining portion of the peptide recognized as the "mature" form of the growth factor. After processing, the "mature" form of the protein normally dimerizes and active homodimeric or even heterodimeric bone morphogenetic proteins are secreted from cells and this dimer, in general, binds to its heteromeric receptor complex composed of BMP receptor type I and BMP receptor type II, to initiate the cell signaling cascade typically associated with the specific BMP activity.

As used herein, "modified growth factor," "modified BMP," "truncated growth factor," or "truncated. BMP" refers to truncations of any form of a wild type BMP disclosed herein, i.e. BMP 2-16, including the full length prepropeptide, the propeptide (the full length peptide without the signaling sequence) and the mature form of the disclosed BMP. The invention therefore provides the composition comprising a protease and an isolated peptide, with the peptide comprising an amino acid sequence at least about 75%, 80%, 85%, 86%, 87%, 88%, 89%, 90%, 91%, 92%, 93%, 94%, 95%, 96%, 97%, 98%, 99% or 100% identical to any of the amino acid sequences of these modified growth factors. In one specific embodiment, the isolated peptide comprises an amino acid sequence at least 92% identical to any of the amino acid sequences of the modified growth factors. In further embodiments, the peptide according to some embodiments of the present invention comprise an amino acid sequence 100% identical to any of the amino acid sequences of the modified growth factors. In still even more embodiments, the peptides consist of any of the amino acid sequences of the modified growth factors.

The modified growth factors in accordance with some embodiments of the present invention include, but are not limited to, truncations of the mature BMPs. Specifically, Table 2 below shows exemplary truncations of various mature BMPs.

TABLE 2

Exemplary truncations of various mature BMPs

| Type of BMP | Truncated Sequence |
|---|---|
| BMP-2 | SEQ ID NO: 16-18 |
| BMP-4 | SEQ ID NO: 19 |
| BMP-5 | SEQ ID NO: 20-28 |
| BMP-6 | SEQ ID NO: 29 |
| BMP-7 | SEQ ID NO: 30-33 |
| BMP-13 | SEQ ID NO: 34 |
| BMP-14 | SEQ ID NO: 35 |

In one embodiment, the isolated peptide is 113, 112, 111, 110, 109, 108, 107, 106, 105, 104 or 103 residues or less with each peptide independently comprising an amino acid sequence at least 75%, 80%, 85%, 86%, 87%, 88%, 89%, 90%, 91%, 92%, 93%, 94%, 95%, 96%, 97%, 98%, 99% or 100% identical to the amino acid sequences of SEQ ID NO:16, 17, or 18.

In another embodiment, the isolated peptide is 115, 114, 113, 112, 111, 110, 109, 108, 107 or 106 residues or less with each peptide independently comprising an amino acid sequence at least 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:19.

In another embodiment, the isolated peptide is 137, 136, 135, 134, 133, 132, 131, 130, 129, 128, 127, 126, 125, 124, 123, 122, 121, 120, 119, 118, 117, 116, 115, 114, 113, 112, 111, 110, 109 residues or less with each peptide independently comprising an amino acid sequence at least 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:20, 21, 22, 23, 24, 25, 26, 27 or 28.

In another embodiment, the isolated peptide is 138, 137, 136, 135, 134, 133, 132, 131, 130, 129, 128, 127, 126, 125, 124, 123, 122, 121, 120, 119, 118, or 117 residues or less with each peptide independently comprising an amino acid sequence at least 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:29.

In another embodiment, the isolated peptide is 138, 137, 136, 135, 134, 133, 132, 131, 130, 129, 128, 127, 126, 125, 124, 123, 122, 121, 120, 119, 118, 117, 116, 115, 114, 113 or 112 residues or less with each peptide independently comprising an amino acid sequence at least 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:30, 31, 32 or 33.

In another embodiment, the isolated peptide is 119, 118, 117, 116, 115, 114, 113, 112, 111, 110, 109 residues or less with each peptide independently comprising an amino acid sequence at least 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:34.

In another embodiment, the isolated peptide is 119, 118, 117, 116, 115, 114, 113, 112, 111, 110, 109, 108, 107, 106 residues or less with each peptide independently comprising an amino acid sequence at least 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:35.

In some embodiments, the peptide variants described herein still retain their ability to specifically interact, at least partially, with its corresponding bone morphogenic protein receptor (BMPR). In additional embodiments, the peptide variants described herein are functional and capable of promoting osteoinductivity, stimulating proliferation of osteoblasts and/or promoting osteogenesis. In further embodiments, the peptide variants described herein are functional and capable of promoting chondroinductivity, stimulating proliferation of chondrocytes and/or promoting chondrogenesis. In even more embodiments, the modified growth factors of the present invention have enhanced activity compared to the unmodified growth faetors. In further embodiments, the compositions comprising a protease and the growth factor described herein have enhanced activity compared to compositions comprising the growth factor without the protease.

A polypeptide having an amino acid sequence at least, for example, about 95% "identical" to a reference an amino acid sequence, SEQ ID NO:16-35, is understood to mean that the amino acid sequence of the polypeptide is identical to the reference sequence except that the amino, acid sequence may include up to about five modifications per each 100 amino acids of the reference amino acid sequence. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using well known techniques. While there are several methods to measure identity between two polynucleotide or polypeptide sequences, the term "identity" is well known to skilled artisans (Carillo (1988) J. Applied Math. 48, 1073). Examples of computer program methods to deteiunne identity and similarity between two sequences include, but are not limited to, GCG program package (Devereux (1984) Nucleic Acids Research 12, 387), BLASTP, ExPASy, BLASTN, FASTA (Atschul (1990) J. Mol. Biol. 215, 403) and FASTDB. Examples of methods to determine identity and similarity are discussed in Michaels (2011) Current Protocols in Protein Science, Vol. 1, John Wiley & Sons.

In one embodiment of the present invention, the algorithm used to determine identity between two or more polypeptides is BLASTP. In another embodiment of the present invention, the algorithm used to determine identity between two or more polypeptides is FASTDB, which is based upon the algorithm of Brutlag (1990) Comp. App. Biosci. 6, 237-245). In a FASTDB sequence alignment, the query and reference sequences are amino sequences. The result of sequence alignment is in percent identity. In one embodiment, parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size-500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent identity. For query sequences truncated at the N- or C-tellnini, relative to the reference sequence, the percent identity is corrected by calculating the number of residues of the query sequence that are N-and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the reference sequence that extend past the N- or C-termini of the query sequence may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-teiininus. The 10 unpaired residues represent 10% of the reference sequence (number of residues at the N- and C-termini not matched/total number of residues in the reference sequence) so 10% is subtracted from the percent identity score calculated by the FASTDB program. If the remaining 90 residues were perfectly matched (100% alignment) the final percent identity would be 90% (100% alignment-10% unmatched overhang). In another example, a 90 residue query sequence is compared with a 100 reference sequence, except that the deletions are internal deletions. In this case the percent identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent identity. The addition in the query occurs at the N-terminus of the query sequence and therefore, the FASTDB alignment may not show a match/alignment of the first 10 residues at the N-terminus. If the remaining 100 amino acid residues of the query sequence have 95% identity to the entire length of the reference sequence, the N-terminal addition of the query would be ignored and the percent identity of the query to the reference sequence would be 95%.

The invention further embraces other species, preferably mammalian, homologs with amino acid sequences that correspond to the modified growth factors of the present invention. Species homologs, sometimes referred to as "orthologs," in general, share at least 35%, 40%, 45%, 50%, 60%, 65%, 70%, 75%, 80%, 85%, 90%, 95%, 96%, 97%, 98%, or 99% sequence identity with the human version of the growth factors. Such corresponding sequences account for the modified growth factor from across a variety of species, such as canine, feline, mouse, rat, rabbit, monkey, etc. of BMP. In another embodiment, the invention provides novel peptides whose sequences correspond to the sequence of SEQ ID NO:16-35 and retain at least some minimal function.

Modified growth factor products with an additional methionine residue at position −1 (Met$^{-1}$-peptide) are contemplated, as are variants with additional methionine and lysine residues at positions −2 and −1 (Met$^{-2}$-Lys$^{-1}$-peptide). Variants of the modified growth factor with additional Met, Met-Lys, or Lys residues (or one or more basic residues in general) are particularly useful for enhanced recombinant protein production in bacterial host cells.

Variants resulting from insertion of the polynucleotide encoding the modified growth factor into an expression vector system are also contemplated. For example, variants (usually insertions) may arise from when the amino terminus and/or the carboxy terminus of modified growth factor is/are fused to another polypeptide.

In another aspect, the invention provides deletion variants wherein one or more amino acid residues in the modified growth factor peptide are removed. Deletions can be effected at one or both termini of the modified growth factor peptide, or with removal of one or more non-terminal amino acid residues of the modified growth factor peptide. Deletion variants, therefore, include all fragments of the modified growth factor peptide.

Within the confines of the disclosed percent identity, the invention also relates to substitution variants of disclosed polypeptides of the invention. Substitution variants include those polypeptides wherein one or more amino acid residues of truncated growth factor are removed and replaced with alternative residues. In one aspect, the substitutions are conservative in nature; however, the invention embraces substitutions that are also non-conservative. Conservative substitutions for this purpose may be defined as set out in the tables below. Amino acids can be classified according to physical properties and contribution to secondary and tertiary protein structure. A conservative substitution is recognized in the art as a substitution of one amino acid for another amino acid that has similar properties. Exemplary conservative substitutions are set out in below.

TABLE 3

Conservative Substitutions

| Side Chain Characteristic | Amino Acid |
|---|---|
| Aliphatic | |
| Non-polar | Gly, Ala, Pro, Iso, Leu, Val |
| Polar-uncharged | Cys, Ser, Thr, Met, Asn, Gln |
| Polar-charged | Asp, Glu, Lys, Arg |
| Aromatic | His, Phe, Trp, Tyr |
| Other | Asn, Gln, Asp, Glu |

Alternatively, conservative amino acids can be grouped as described in Lehninger (1975) Biochemistry, Second Edition; Worth Publishers, pp. 71-77, as set forth below.

TABLE 4

Conservative Substitutions

| Side Chain Characteristic | Amino Acid |
|---|---|
| Non-polar (hydrophobic) | |
| Aliphatic: | Ala, Leu, Iso, Val, Pro |
| Aromatic: | Phe, Trp |

TABLE 4-continued

Conservative Substitutions

| Side Chain Characteristic | Amino Acid |
|---|---|
| Sulfur-containing: | Met |
| Borderline: | Gly |
| Uncharged-polar | |
| Hydroxyl: | Ser, Thr, Tyr |
| Amides: | Asn, Gln |
| Sulfhydyl: | Cys |
| Borderline: | Gly |
| Positively Charged (Basic): | Lys, Arg, His |
| Negatively Charged (Acidic): | Asp, Glu |

And still other alternative, exemplary conservative substitutions are set out below.

TABLE 5

Conservative Substitutions

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Len, Met, Phe, Ala |

The polypeptides according to the present invention may or may not be involved in a dimer. In one embodiment, the invention provides dimers, wherein the dimers comprise at least one of the novel, modified growth factors described herein. In one specific embodiment, the dimers are homodimers of the novel modified growth factors. In another embodiment, the dimers are heterodimers comprising at least one of the novel modified growth factors. As used herein, a "heterodimer" means a dimer of two peptides, wherein the amino acid sequences of the peptides are not 100% identical to each other. Thus, a heterodimer may include a modified growth factor peptide of the present invention dimerized with a normal, "mature" version of the same growth factor.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. In some embodiments, at least one refers, for example, to 1, 2, 3, 4, 5, 6, 7, 8, 9, or 10.

It should be understood that the definition of peptides or polypeptides of the invention is intended to include polypeptides bearing modifications other than insertion, deletion, or substitution of amino acid residues. By way of example, the modifications may be covalent in nature, and include for example, chemical bonding with polymers, lipids, other organic and inorganic moieties. Such derivatives may be prepared to increase circulating half-life of a polypeptide, or may be designed to improve the targeting capacity of the polypeptide for desired cells, tissues or organs. Similarly, the invention further embraces modified growth factor peptides that have been covalently modified to include one or more water-soluble polymer attachments such as polyethylene glycol, polyoxyethylene glycol or polypropylene glycol.

Modified growth factor compositions in which the modified growth factor is linked to a polymer are included within the scope of the present invention. The polymer may be water soluble to prevent precipitation of the protein in an aqueous environment, such as a physiological environment. Suitable water-soluble polymers may be selected from the group consisting of, for example, polyethylene glycol (PEG), monomethoxypolyethylene glycol, dextran, cellulose, or other carbohydrate based polymers, poly-(N-vinyl pyrrolidone) polyethylene glycol, polypropylene glycol homopolymers, a polypropylene oxide/ethylene oxide copolymer polyoxyethylated polyols (e.g., glycerol) and polyvinyl alcohol. The selected polymer is usually modified to have a single reactive group, such as an active ester for acylation or an aldehyde for alkylation, so that the degree of polymerization may be controlled. Polymers may be of any molecular weight, and may be branched or unbranched, and mixtures of such polymers may also be used. When the chemically modified NgR polymer is destined for therapeutic use, pharmaceutically acceptable polymers will be selected for use.

Pegylation of modified growth factor peptides may be carried out by any of the pegylation reactions known in the art. For example, the pegylation is carried out via an acylation reaction or an alkylation reaction with a reactive polyethylene glycol molecule (or an analogous reactive water-soluble polymer). One water-soluble polymer for pegylation of polypeptides is polyethylene glycol (PEG), including, but not limited to bi-functional PEGs. As used herein, "polyethylene glycol" is meant to encompass any of the forms of PEG that have been used to derivatize other proteins, such as mono (C1-C10) alkoxy- or aryloxy-polyethylene Chemical derivatization of modified growth factor may be performed under any suitable conditions used to react with a biologically active substance with an activated polymer molecule. Methods for preparing pegylated modified growth factor will generally comprise the steps of (a) reacting the polypeptide with polyethylene glycol, such as a reactive ester or aldehyde derivative of PEG, under conditions whereby modified growth factor polypeptide becomes attached to one or more PEG groups, and (b) obtaining the reaction products. It will be apparent to one of ordinary skill in the art to select the optimal reaction conditions or the acylation reactions based on known parameters and the desired result.

Pegylated and other polymer modified growth factor polypeptides may generally be used to treat conditions that may be alleviated or modulated by administration of the modified growth factor polypeptides described herein. However, the chemically-derivatized polymer: modified growth factor polypeptide molecules disclosed herein may have additional activities, enhanced or reduced biological activity, or other characteristics, such as increased or decreased half-life, as compared to the nonderivatized molecules. The modified growth factor polypeptides, fragments thereof, variants and derivatives, may be employed alone, together, or in combination with other pharmaceutical compositions. For example, cytokines, growth factors, antibiotics, anti-inflammatories and/or chemotherapeutic agents may be co-administered as is appropriate for the indication being treated.

The present invention provides compositions comprising purified polypeptides of the invention. Preferred compositions comprise, in addition to the polypeptide of the invention, a pharmaceutically acceptable (i.e., sterile and non-toxic) liquid, semisolid, or solid diluent that serves as a pharmaceutical vehicle, excipient or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil and cocoa butter.

In one embodiment, the growth factors according to the present invention are fusion proteins that comprise at least a first and a second fusion peptides. The fusion partners are, generally speaking, covalently bonded to one another via a typical amine bond between the fusion peptides, thus creating one contiguous amino acid chain. In some embodiments, the first peptide of the fusion protein comprises the modified growth factor described herein. In further embodiments, the second fusion peptide comprises an amino acid sequence that does not include the amino acid sequence of SEQ ID NO:36-55.

In one embodiment, the first fusion peptide comprises a modified growth factor from BMP-2, and the second fusion peptide comprises an amino acid sequence that does not include the amino acid sequence of SEQ ID NO:36, 37 or 38. In more specific embodiments, the second fusion of the present invention comprises an amino acid sequence that is less than 10%, 20%, 30%, 40%, 50%, 60%, 70%, 80%, 90% or 100% identical to SEQ ID NO:36, 37 or 38.

In another embodiment, the first fusion peptide comprises a modified growth factor from BMP-4, and the second fusion peptide comprises an amino acid sequence that does not include the amino acid sequence of SEQ ID NO:39. In more specific embodiments, the second fusion of the present invention comprises an amino acid sequence that is less than 10%, 20%, 30%, 40%, 50%, 60%, 70%, 80%, 90% or 100% identical to SEQ ID NO:39.

In another embodiment, the first fusion peptide comprises a modified growth factor from BMP-5, and the second fusion peptide comprises an amino acid sequence that does not include the amino acid sequence of SEQ ID NO:40, 41, 42, 43, 44, 45, 46, 47 or 48. In more specific embodiments, the second fusion of the present invention comprises an amino acid sequence that is less than 10%, 20%, 30%, 40%, 50%, 60%, 70%, 80%, 90% or 100% identical to SEQ ID NO:40, 41, 42, 43, 44, 45, 46, 47 or 48.

In another embodiment, the first fusion peptide comprises a modified growth factor from BMP-6, and the second fusion peptide comprises an amino acid sequence that does not include the amino acid sequence of SEQ ID NO:49. In more specific embodiments, the second fusion of the present invention comprises an amino acid sequence that is less than 10%, 20%, 30%, 40%, 50%, 60%, 70%, 80%, 90% or 100% identical to SEQ ID NO:49.

In another embodiment, the first fusion peptide comprises a modified growth factor from BMP-7, and the second fusion peptide comprises an amino acid sequence that does not include the amino acid sequence of SEQ ID NO:50, 51, 52 or 53. In more specific embodiments, the second fusion of the present invention comprises an amino acid sequence that is less than 10%, 20%, 30%, 40%, 50%, 60%, 70%, 80%, 90% or 100% identical to SEQ ID NO:50, 51, 52 or 53.

In another embodiment, the first fusion peptide comprises a modified growth factor from BMP-13, and the second fusion peptide comprises an amino acid sequence that does not include the amino acid sequence of SEQ ID NO:54. In more specific embodiments, the second fusion of the present invention comprises an amino acid sequence that is less than 10%, 20%, 30%, 40%, 50%, 60%, 70%, 80%, 90% or 100% identical to SEQ ID NO:54.

In another embodiment, the first fusion peptide comprises a modified growth factor from BMP-14, and the second fusion peptide comprises an amino acid sequence that does not include the amino acid sequence of SEQ ID NO:55. In more specific embodiments, the second fusion of the present invention comprises an amino acid sequence that is less than 10%, 20%, 30%, 40%, 50%, 60%, 70%, 80%, 90% or 100% identical to SEQ ID NO:55.

Other types of fusion proteins provided by the present invention include but are not limited to, fusions with secretion signals and other heterologous functional regions. Thus, for instance, a region of additional amino acids, particularly charged amino acids, may be added to the N-terminus of the protein to improve stability and persistence in the host cell, during purification or during subsequent handling and storage.

Additional fusion proteins include fusions for enhancing translocation of the protein across cell membranes. For example, Tat is an 86-amino acid protein involved in the replication of human immunodeficiency virus type 1 (HIV-1). The HIV-1 Tat transactivation protein is efficiently taken up by cells, and it has been demonstrated that low concentrations (nM) are sufficient to transactivate a reporter gene expressed from the HIV-1 promoter. Exogenous Tat protein is able to translocate through the plasma membrane and reach the nucleus to transactivate the viral genome. Tat peptide-mediated cellular uptake and nuclear translocation have been demonstrated in several systems. Chemically coupling a Tat-derived peptide (residues 37-72 of Tat) to several proteins results in their internalization in several cell lines or tissues (Fawell (1994) Proc. Natl. Acad. Sci. USA 91, 664-668).

It is well-known that a region of the Tat protein centered on a cluster of basic amino acids is responsible for this translocation activity. A synthetic peptide consisting of the Tat basic amino acids 48-60 with a cysteine residue at the C-terminus coupled to fluorescein maleimide translocates to the cell nucleus as determined by fluorescence microscopy. In addition, a fusion protein (Tat-NLS-β-Gal) consisting of Tat amino acids 48-59 fused by their amino-terminus to β-galactosidase amino acids 9-1023 translocates to the cell nucleus in an ATP-dependent, cytosolic factor-independent manner. Accordingly, the fusion proteins of the present invention may comprise all or a portion of HIV-Tat, such as any sequential residues of the Tat protein basic peptide motif 37-72 (37-CFITKALGISYGRKKRRQRRRPPQG-SQTHQVSLSKQ-72 (SEQ ID NO:56). The minimum number of amino acid residues can be in the range of from about three to about six. In one embodiment, the Tat portion of the fusion protein is from about three to about five contiguous amino acids in length. In another embodiment, the Tat portion of the fusion protein is about four amino acids in length, i.e., the minimal requirement for one alpha helical turn. In another embodiment, the Tat portion of the fusion protein comprises Tat protein residues 48-57 (GRK-KRRQRRR) (SEQ ID NO:57).

In additional embodiments of fusion proteins, a region may be added to facilitate purification. For example, "histidine tags" ("his tags") or "lysine tags" (the second fusion peptide) may be appended to the first fusion peptide. Examples of histidine tags include, but are not limited to, hexaH, heptaH and hexaHN. Examples of lysine tags include, but are not limited to pentaL, heptaL and FLAG. Such regions may be removed prior to final preparation of the protein. Other examples of a second fusion peptide include, but are not limited to, glutathione S-transferase (GST) and alkaline phosphatase (AP).

The addition of peptide moieties to proteins, whether to engender secretion or excretion, to improve stability and to facilitate purification or translocation, among others, is a familiar and routine technique in the art and may include modifying amino acids at the terminus to accommodate the tags. For example in any of SEQ ID NO: 16-35, the N-tenninus amino acid may be modified to, for example, arginine and/or serine to accommodate a tag. Of course, the amino acid residues of the C-terminus may also be modified to accommodate tags. One particularly useful fusion protein comprises a heterologous region from immunoglobulin that can be used solubilize proteins. For example, EP A0464 533 discloses fusion proteins comprising various portions of constant region of immunoglobin molecules together with another human protein or part thereof. In many cases, the Fc part in a fusion protein is thoroughly advantageous for use in therapy and diagnosis and thereby results, for example, in improved pharmacokinetic properties (EP A0232 262). On the other hand, for some uses, it would be desirable to be able to delete the Fe part after the fusion protein has been expressed, detected and purified in the advantageous manner described.

The fusion proteins of the current invention can be recovered and purified from recombinant cell cultures by well-known methods including, but not limited to, ammonium sulfate or ethanol precipitation, acid extraction, anion or cation exchange chromatography, phosphocellulose chromatography, hydrophobic interaction chromatography, affinity chromatography, e.g., immobilized metal affinity chromatography (IMAC), hydroxylapatite chromatography and lectin chromatography. High performance liquid chromatography ("HPLC") may also be employed for purification. Well-known techniques for refolding protein may be employed to regenerate active conformation when the fusion protein is denatured during isolation and/or purification.

Fusion proteins of the present invention include, but are not limited to, products of chemical synthetic procedures and products produced by recombinant techniques from a prokaryotic or eukaryotic host, including, for example, bacterial, yeast, higher plant, insect and mammalian cells. Depending upon the host employed in a recombinant production procedure, the fusion proteins of the present invention may be glycosylated or may be non-glycosylated. In addition, fusion proteins of the invention may also include an initial modified methionine residue, in some cases as a result of host-mediated processes.

The invention also relates to isolated nucleic acids and to constructs comprising these nucleic acids. The nucleic acids of the invention can be DNA or RNA, for example, mRNA. The nucleic acid molecules can be double-stranded or single-stranded; single stranded RNA or DNA can be the coding, or sense, strand or the non-coding, or antisense, strand. In particular, the nucleic acids may encode any polypeptide of the invention, including, but not limited to, the fusion proteins of the present invention. For example, the nucleic acids of the invention include polynucleotide sequences that encode glutathione-S-transferase (GST) fusion protein, poly-histidine (e.g., His$_6$), poly-HN, poly-lysine, hemagglutinin, HSV-Tag and at least a portion of HIV-Tat. If desired, the nucleotide sequence of the isolated nucleic acid can include additional non-coding sequences such as non-coding 3' and 5' sequences (including regulatory sequences, for example).

In some embodiments, the isolated nucleic acid of the present invention further relates to the nucleic acids consisting of a nucleic acid sequence at least 95% identical to any of the nucleic acid sequences of SEQ ID NO: 58-77. In further embodiments, the invention therefore provides the nucleic acids consisting of a nucleic acid sequence at least about 75%, 80%, 85%, 86%, 87%, 88%, 89%, 90%, 91%, 92%, 93%, 94%, 95%, 96%, 97%, 98%, 99% or 100% identical to any of the nucleic acid sequences of SEQ ID NO: 58-77.

The nucleic acid molecules of the invention can be "isolated." As used herein, an "isolated" nucleic acid molecule or nucleotide sequence is intended to mean a nucleic acid molecule or nucleotide sequence that is not flanked by nucleotide sequences normally flanking the gene or nucleotide sequence (as in genomic sequences) and/or has been completely or partially removed from its native environment (e.g., a cell, tissue). For example, nucleic acid molecules that have been removed or purified from cells are considered isolated. In some instances, the isolated material will form part of a composition (for example, a crude extract containing other substances), buffer system or reagent mix. In other circumstances, the material may be purified to near homogeneity, for example as determined by PAGE or column chromatography such as HPLC. Thus, an isolated nucleic acid molecule or nucleotide sequence can includes a nucleic acid molecule or nucleotide sequence which is synthesized chemically, using recombinant DNA technology or using any other suitable method. To be clear, a nucleic acid contained in a vector would be included in the definition of "isolated" as used herein. Also, isolated nucleotide sequences include recombinant nucleic acid molecules (e.g., DNA, RNA) in heterologous organisms, as well as partially or substantially purified nucleic acids in solution. "Purified," on the other hand is well understood in the art and generally means that the nucleic acid molecules are substantially free of cellular material, cellular components, chemical precursors or other chemicals beyond, perhaps, buffer or solvent. "Substantially free" is not intended to mean that other components beyond the novel nucleic acid molecules are undetectable. The nucleic acid molecules of the present invention may be isolated or purified. Both in vivo and in vitro RNA transcripts of a DNA molecule of the present invention are also encompassed by "isolated" nucleotide sequences.

The invention also encompasses variations of the nucleotide sequences of the invention, such as those encoding functional fragments or variants of the polypeptides as described above. Such variants can be naturally-occurring, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions.

The invention described herein also relates to fragments of the isolated nucleic acid molecules described herein. The term "fragment" is intended to encompass a portion of a nucleotide sequence described herein which is from at least about 20 contiguous nucleotides to at least about 50 contiguous nucleotides or longer in length. Such fragments may be useful as probes and primers. In particular, primers and probes may selectively hybridize to the nucleic acid molecule encoding the polypeptides described herein. For example, fragments which encode polypeptides that retain activity, as described below, are particularly useful.

The invention also provides nucleic acid molecules that hybridize under high stringency hybridization conditions, such as for selective hybridization, to the nucleotide sequences described herein (e.g., nucleic acid molecules which specifically hybridize to a nucleotide sequence encoding polypeptides described herein and encode a modified growth factor). Hybridization probes include synthetic oligonucleotides which bind in a base-specific manner to a complementary strand of nucleic acid.

Such nucleic acid molecules can be detected and/or isolated by specific hybridization e.g., under high stringency conditions. "Stringency conditions" for hybridization is a term of art that refers to the incubation and wash conditions, e.g., conditions of temperature and buffer concentration, which permit hybridization of a particular nucleic acid to a second nucleic acid; the first nucleic acid may be perfectly complementary, 100%, to the second, or the first and second may share some degree of complementarity, which is less than perfect, e.g., 60%, 75%, 85%, 95% or more. For example, certain high stringency conditions can be used which distinguish perfectly complementary nucleic acids from those of less complementarity.

"High stringency conditions," "moderate stringency conditions" and "low stringency conditions" for nucleic acid hybridizations are explained in Current Protocols in Molecular Biology, John Wiley & Sons). The exact conditions which determine the stringency of hybridization depend not only on ionic strength, e.g., 0.2×SSC, 0.1×SSC of the wash buffers, temperature, e.g., room temperature, 42° C., 68° C., etc., and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined. Exemplary conditions are described in Krause (1991) Methods in Enzymology, 200:546-556. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in Tm. Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Example of progressively higher stringency conditions include, after hybridization, washing with 0.2 ×SSC and 0.1% SDS at about room temperature (low stringency conditions); washing with 0.2×SSC, and 0.1% SDS at about 42° C. (moderate stringency conditions); and washing with 0.1×SSC at about 68° C. (high stringency conditions). Washing can be carried out using only one of these conditions, e.g., high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example. The term "primer" is used herein as it is in the art and refers to a single-stranded oligonucleotide which acts as a point of initiation of template-directed DNA synthesis under appropriate conditions in an appropriate buffer and at a suitable temperature. The appropriate length of a primer depends on the intended use of the primer, but typically ranges from about 15 to about 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The present invention also relates to vectors that include nucleic acid molecules of the present invention, host cells that are genetically engineered with vectors of the invention and the production of proteins of the invention by recombinant techniques.

In accordance with this aspect of the invention, the vector may be, for example, a plasmid vector, a single-or double-stranded phage vector, or a single-or double-stranded RNA or DNA viral vector. Such vectors may be introduced into cells as polynucleotides, for example DNA, by well-known techniques for introducing DNA and RNA into cells. Viral vectors may be replication competent or replication defective. In the latter, case viral propagation generally will occur only in complementing host cells.

In certain respects, the vectors to be used are those for expression of polynucleotides and proteins of the present invention. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express the proteins of the invention. Such vectors include chromosomal, episomal and virus-derived vectors, e.g., vectors derived from bacterial plasmids, from bacteriophage, from yeast episomes, from yeast chromosomal elements, from viruses such as adeno-associated virus, lentivirus, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the present invention. Generally, any vector suitable to maintain, propagate or express polynucleotides or proteins in a host may be used for expression in this regard.

The DNA sequence in the expression vector is operatively linked to appropriate expression control sequence(s) including, for instance, a promoter to direct mRNA transcription. Representatives of such promoters include, but are not limited to, the phage lambda PL promoter, the *E. coli* lac, trp and tac promoters, HIV promoters, the SV40 early and late promoters and promoters of retroviral LTRs, to name just a few of the well-known promoters. In general, expression constructs will contain sites for transcription, initiation and termination and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors may contain one or more selectable marker genes to provide a phenotypic trait for selection of transformed host cells. Preferred markers include dihydrofolate reductase or neomycin resistance for eukaryotic cell culture, and tetracycline, kanamycin or ampicillin resistance genes for culturing *E. coli* and other bacteria.

The vector containing the appropriate DNA sequence, as well as an appropriate promoter, and other appropriate control sequences, may be introduced into an appropriate host using a variety of well-known techniques suitable to expression therein of a desired polypeptide. Representative examples of appropriate hosts include bacterial cells, such as, but not limited to, *E. coli*, Streptomyces, Bacillus, and Salmonella cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill in the art will be enabled by the present disclosure to select an appropriate host for expressing one of the proteins of the present invention.

Examples of vectors that may be useful for fusion proteins include, but are not limited to, pGEX (Pharmacia), pMAL (New England. Biolabs) and pRITS (Pharmacia) that fuse glutathione-S-transferase (GST), maltose E binding protein, or protein A, respectively, to the target recombinant protein. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Examples vectors for expression in yeast *S. cerevisiae* include pYepSecl (Baldari (1987) EMBO J. 6, 229-234), pMFa (Kurjan (1982) Cell 30, 933-943), pJRY88 (Schultz (1987) Gene 54, 137-123), pYES2 (Invitrogen) and picZ (Invitrogen).

Alternatively, the modified growth factors can be expressed in insect cells using baculovirus expression vectors. Baculovirus vectors available for expression of proteins in cultured insect cells (e.g., SF9 cells) include the pAc series (Smith (1983) Mol. Cell. Biol. 3, 2156 2165) and the pVL series (Lucklow (1989) Virology 170, 31-39).

In yet another embodiment, a nucleic acid of the invention is expressed in mammalian cells using a mammalian expression vector. Examples of mammalian expression vectors include pCDM8 (Seed (1987) Nature 329, 840) and pMT2PC (Kaufman (1987) EMBO J. 6, 187 195). When used in mammalian cells, the expression vector's control functions are often provided by viral regulatory elements. For example, commonly used promoters are derived from polyoma, adenovirus 2, cytomegalovirus and Simian Virus 40. For other suitable expression systems for both prokaryotic and eukaryotic cells, see Sambrook (2010) Molecular Cloning: A Laboratory Manual. Cold Spring Harbor Laboratory Press.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include liver-specific promoters (e.g., albumin promoter), lymphoid-specific promoters such as, but not limited to, T cell receptors and immunoglobulins, neuron-specific promoters (e.g., neurofilament promoter), pancreas-specific promoters, mammary gland-specific promoters (e.g., milk whey promoter), bone-specific promoters (e.g., osteocalcin, osteopontin or bone sialoprotein, promoter regions), cartilage specific promoters (e.g., WARP) and muscle specific promoters (Desmin, myglobin, etc) just to name a few. Developmentally-regulated promoters are also encompassed, e.g., the murine box promoters (Kessel and Gruss (1990) Science 249, 374 379) and the a-fetoprotein promoter (Campes and Tilghman (1989) Genes Dev. 3, 537 546).

The present invention also relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. The host cell can be stably or transiently transfected with the construct. The polynucleotides may be introduced alone or with other polynucleotides. Such other polynucleotides may be introduced independently, co-introduced or introduced joined to the polynucleotides of the invention. As used herein, a "host cell" is a cell that normally does not contain any of the nucleotides of the present invention and contains at least one copy of the nucleotides of the present invention. Thus, a host cell as used herein can be a cell in a culture setting or the host cell can be in an organism setting where the host cell is part of an organism, organ or tissue.

Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera Escherichia, Bacillus, Pseudomonas, Staphylococcus, and Streptomyces.

If a eukaryotic expression vector is employed, then the appropriate host cell would be any eukaryotic cell capable of expressing the cloned sequence. In one embodiment, eukaryotic cells are cells of higher eukaryotes. Suitable eukaryotic cells include, but are not limited to, non-human mammalian tissue culture cells and human tissue culture cells. Other host cells include, but are not limited to, insect cells, HeLa cells, Chinese hamster ovary cells (CHO cells), African green monkey kidney cells (COS cells), human 293 cells, and murine 3T3 fibroblasts.

In addition, a yeast cell may be employed as a host cell. Yeast cells include, but are not limited to, the genera *Saccharomyces, Pichia* and *Kluveromyces*. In one embodiment, the yeast hosts are S. cerevisiae or P. pastoris. Yeast vectors may contain an origin of replication sequence from a 2T yeast plasmid, an autonomously replication sequence (ARS), a promoter region, sequences for polyadenylation, sequences for transcription termination and a selectable marker gene. Shuttle vectors for replication in both yeast and E. coli are also included herein.

Introduction of a construct into the host cell can be affected by calcium phosphate transfection, DEAE-dextran mediated transfection, cationic lipid-mediated transfection, electroporation, transduction, infection or other methods.

For stable transfection of mammalian cells, it is known that, depending upon the expression vector and transfection technique used, only a small fraction of cells may integrate the foreign DNA into their genome. To identify and select these integrants, a gene that encodes a selectable marker (e.g., resistance to antibiotics) is generally introduced into the host cells along with the gene of interest. Various selectable markers include those that confer resistance to drugs, such as G418, hygromycin, dihydrofolate reductase (DHFR) and methotrexate. Nucleic acid encoding a selectable marker can be introduced into a host cell on the same vector as that encoding modified growth factor or can be introduced on a separate vector. Cells stably transfected with the introduced nucleic acid can be identified by drug selection (e.g., cells that have incorporated the selectable marker gene will survive, while the other cells die). In one embodiment, the polypeptides of the invention are expressed in Chinese Hamster Ovary (CHO) cells.

The modified growth factor expression vectors prepared as above are introduced into CHO cells by any known method, including, but not limited to the calcium phosphate method and electroporation.

Transformants carrying the expression vectors are selected based on the above-mentioned selectable markers. Repeated clonal selection of the transformants using the selectable markers allows selection of stable cell lines expressing the modified growth factor constructs. Increased concentrations in the selection medium allows gene amplification and greater expression of the desired modified growth factor. The host cells, for example CHO cells, containing the recombinant modified growth factor can be produced by cultivating the CHO cells containing the modified growth factor expression vectors constitutively expressing the modified growth factor constructs.

Accordingly, the current invention also relates to methods of producing a modified growth factor comprising culturing the host cells of the invention under conditions such that the modified growth factor is expressed, and recovering said protein. The culture conditions required to express the proteins of the current invention are dependent upon the host cells that are harboring the polynucleotides of the current invention. The culture conditions for each cell type are well-known in the art and can be easily optimized, if necessary. For example, a nucleic acid encoding a polypeptide of the invention, or a construct comprising such nucleic acid, can be introduced into a suitable host cell by a method appropriate to the host cell selected, e.g., transformation, transfection, electroporation, infection, such that the nucleic acid is operably linked to one or more expression control elements as described herein. Host cells can be maintained under conditions suitable for expression in vitro or in vivo, whereby the encoded polypeptide is produced. For example host cells may be maintained in the presence of an inducer, suitable media supplemented with appropriate salts, growth factors, antibiotic, nutritional supplements, etc., which may facilitate protein expression. In additional embodiments, the modified growth factors of the invention can be produced by in vitro translation of a nucleic acid that encodes the modified growth factor, by chemical synthesis or by any other suitable method. If desired, the modified growth factor can be isolated from the host cell or other environment in which the protein is produced or secreted. It should therefore be appreciated that the methods of producing the modified growth factors encompass expression of the polypeptides in a host cell of a transgenic animal or plant. See U.S. Pat. Nos. 6,013,857, 5,990,385, and 5,994,616.

In situations where the modified BMP will be found primarily intracellularly, intracellular material (including inclusion bodies for Gram-negative bacteria) can be extracted from the host cell using any standard technique known to one of ordinary skill in the art. Such methods would encompass, by way of example and not by way of limitation, lysing the host cells to release the contents of the periplasm/cytoplasm by French press, homogenization and/or sonication followed by centrifugation.

If the modified BMP has formed inclusion bodies in the cytosol, such inclusion bodies may frequently bind to the inner and/or outer cellular membranes. Upon centrifugation, the inclusion bodies will be found primarily in the pellet material. The pellet material can then be treated at pH extremes or with one or more chaotropic agents such as a detergent, guanidine, guanidine derivatives, urea, or urea derivatives in the presence of a reducing agent such as dithiothreitol at alkaline pH or tris-carboxyethyl phosphine at acid pH to release, break apart and solubilize the inclusion bodies. Once solubilized, the modified growth factor peptide can be analyzed using gel electrophoresis, immunoprecipitation or the like. Various methods of isolating the modified growth factor peptide would be apparent to one of ordinary skill in the art, for example, isolation may be accomplished using standard methods such as those set forth below and in Marston et al (1990) Meth. Enzyinol. 182, 264-275.

If the modified growth factor peptide is not biologically active following the isolation procedure employed, various methods for "refolding" or converting the polypeptide to its tertiary structure and generating disulfide linkages, can be used to restore biological activity. Methods known to one of ordinary skill in the art include adjusting the pH of the solubilized polypeptide to a certain pH, usually above 7, and in the presence of a particular concentration of a chaotrope. The selection of chaotrope is very similar to the choices used for inclusion body solubilization, but usually at a lower concentration, and is not necessarily the same chaotrope as used for the solubilization. It may be required to employ a reducing agent or the reducing agent plus its oxidized form in a specific ratio, to generate a particular redox potential allowing for disulfide shuffling during the formation of the protein's cysteine bridge(s). Some of the commonly used redox couples include cysteine/cysteine, glutathione (GSH)/dithiobis GSH, cupric chloride, dithiothreitol (DTT)/dithiane DTT, 2-mercaptoethanol (bME)/dithio-b(ME). To increase the efficiency of the refolding, it may be necessary to employ a cosolvent, such as glycerol, polyethylene glycol of various molecular weights and arginine.

Other methods of preparing the modified growth factors of the present invention include, but are not limited to, contacting a form of BMP with a protease. In one embodiment, the methods comprise contacting the mature form of BMP with a protease to produce the modified growth factors of the present invention.

As used herein, the term "protease" refers to any of various enzymes that catalyze the hydrolytic breakdown of proteins into smaller segments, including polypeptides and/or amino acids. Accordingly, included in the definition are proteinases and peptidases. The term "proteinase" refers to a protease that catalyzes the hydrolytic breakdown of proteins by splitting them into smaller peptide fractions, i.e., polypeptides or amino acids. The term "peptidase" refers to a protease that catalyzes the hydrolytic breakdown of peptides via cleavage of an individual amino acid from the peptide chain.

In one embodiment, the protease is a serine protease, a threonine protease, a metalloproteinase, a cysteine protease, an aspartate protease or a glutamic acid protease. Examples of such proteases are well known in the art and include proteases from both eukaryotic and prokaryotic sources. Examples of serine proteases include, but are not limited to, chymotrypsin, trypsin, thrombin, elastase, subtilisin and alpha/beta hydrolases. Examples of cysteine proteases include, but are not limited to, actinidain, bromelain, calpains, some cathepsins, clostripain and papain. Examples of aspartate proteases include, but are not limited to, some cathepsins, chyomsin, renin, pepsin and HIV-1 protease. Examples of metalloproteinases include, but are not limited to, the matrix metalloproteinase (MMP) family of proteases that include MMP-1, MMP-2, MMP-3, MMP-4, MMP-5, MMP-6, MMP-7, MMP-8, MMP-9, MMP-10, MMP-11, MMP-12, MMP-13, MMP-14, MMP-15, MMP-16, MMP-17, MMP-18 and membrane-type MMP (MT-MMP), to name a few. Many of these MMPs are known by other names in the art and one of skill will be informed of synonyms of the various enzymes. For example, some of the "collagenases" are MMP-1, MMP-8, MMP-13, MMP-14, MMP-18 and dispases, and some of the "gelatinases" are MMP-2, MMP-9 and MMP-12; some of the "stromelysins" are MMP-3, MMP-10 and MMP-11, and some of the membrane-type matrix metalloproteinases are MMP-14, MMP-15, MMP-16, MMP-17, MMP-24, and MMP-25. Collagenases are examples of metalloproteinases that break down native collagen or gelatin. A variety of microorganisms and many different types of animal cells produce collagenases. Bacterial collagenases are often used in the laboratory to digest tissues and isolate individual cells. Collagenase produced by *Clostridium histolyticum* (*C. histolyticum*) is a zinc metalloproteinase that degrades various types of collagen and gelatin. Additional examples of metalloproteinases are the astacin family, such as, but not limited to, astacin, tolloid, xolloid, mammalian tolloid like (mTLL), BMP-1, meprin A and B, and matrilysin and the aggrecanase (AD-AMTS) family of metalloproteinase, such as, but not limited to, ADAMTS-1, ADAMTS-2, ADAMTS-3, ADAMTS-4, ADAMTS-5.

Of course, the methods include contacting a form of BMP with more than one protease either sequentially or simultaneously. In addition, the proteases used herein can be recombinant or isolated from various sources. The proteases used herein need not be isolated from the same cellular or animal source as the mature form of the BMP. For example, many proteases are found only in prokaryotes, yet these proteases are functional against proteins from eukaryotes. Factors affecting enzyme activity include, but are not limited to, salt concentrations of buffer, pH and temperature. One of skill in the art will readily understand the conditions necessary to promote peptide cleave based upon the enzyme used.

In some embodiments, the ratio of the amount of protease(s) to the amount of growth factor(s) may be between about 1 mol protease:1000 mol growth factor and about 1000 mol:1 mol, between about 1 mol protease:1000 mol growth factor and about 100 mol:1 mol, between about 1 mol:100 mol and about 100 mol:1 mol, between about 1 mol:100 mol and about 10 mol:1 mol, between about 1 mol:10 mol and about 10 mol:1 mol, or between about 1 mol:10 mol and about 1 mol:1 mol. In further embodiments, the ratio of the amount of collagenase(s) to the amount of growth factor(s) may be between about 1 mol collagenase: 100 mol growth factor and about 1000 mol:1 mol, between about 1 mol:10 mol and about 1000 mol:1 mol, between about 1 mol:10 mol and about 100 mol:1 mol, or between about 1 mol:1 mol and about 10 mol:1 mol. The ratio of the amount of trypsin to the amount of growth factor(s) may be between about 1 mol trypsin: 1000 mol growth factor and about 1000 mol:1 mol, between about 1 mol:1000 mol and about 100 mol:1 mol, between about 1 mol:100 mol and about 10 mol:1 mol, or between about 1 mol:10 mol and about 10 mol:1 mol. The ratio of the amount of clostripain to the amount of growth factor(s) may be between about 1 mol clostripain:1000 mol growth factor and about 1000 mol:1 mol, between about 1 mol:100 mol and about 1000 mol:1 mol, between about 1 mol:10 mol and about 100 mol:1 mol, or between about 1 mol:1 mol and about 10 mol:1 mol. The ratio of the amount of dispase to the amount of growth factor(s) may be between about 1 mol dispase: 1000 mol growth factor and about 1000 mol:1 mol, between about 1 mol:1000 mol and about 100 mol:1 mol, between about 1 mol:100 mol and about 10 mol: 1 mol, or between about 1 mol:10 mol and about 10 mol:1 mol.

The treatment of growth factor(s) with proteases may be performed at a temperature between about 0° C. and about 40° C., about 4° C. and about 40° C., or at about 37° C. or lower, in some embodiments. A growth factor may be treated with collagenase for between about 30 minutes and 3 days, about 1 hour and about 48 hours, about 2 hours and about 48 hours, or about 2 hours and about 24 hours, in certain embodiments. A growth factor may be treated with trypsin or clostripain for between about 5 minutes and 3 days, about 5 minutes and about 48 hours, about 5 minutes and about 24 hours, or about 5 minutes and about 8 hours. A growth factor may be treated with dispase for between about 5 minutes and 2 days, about 5 minutes and about 24 hours, about 5 minutes and about 18 hours, or about 5 minutes and about 8 hours. All these conditions do not count the extra protein or peptide substrate in the treatment mixture. Treatment may include mixing and/or incubation. Incubation may be perfoimed under static or dynamic conditions, such as with agitation, shaking, stirring, mixing, horizontal motion, rocking, and others.

In some embodiments, the protease may be a recombinant protein or peptide fragment, a chemically synthesized protein or peptide fragment, or it may be extracted from a natural source and, optionally, modified, for example by being cleaved, inactivated, chemically-modified, or other methods. In other embodiments, certain aspects of the enzymatic activity of a protease may be inhibited or altered, and the protease having altered activity may be added to one or more growth factors to change the biological activity of the growth factor.

In additional embodiments, the activity of a protease may be modulated before, during, or after treatment of at least one growth factor with the protease. For example, the protease activity of a collagenase may be significantly reduced before it is used to treat a growth factor. In another example, the activity of a protease may be modulated before, during, or after administering to cells. In certain embodiments, the activity of a protease may be modulated by methods comprising heat inactivation, radiation inactivation, protease substrate neutralization, or chemical inhibition, among others. The chemical inhibitor used to modulate the activity of metalloproteinases may be selected from metal chelating agents, such as EDTA; cysteine and serine protease inhibitors, such as N-ethylmaleimide, phenylmethylsulfonyl fluoride (PMSF), and leupeptin; classical metalloproteinase inhibitor, such as phosphoramidon,and bestatin; general protein inhibitor, such as a2-macroglobuli, or natural or synthetic tissue inhibitors of metalloproteinases (TIMPs), such as TIMP-1, TIMP-2, TIMP-3, TIMP-4; and other inhibitors.

The form of BMP used in these methods can also be recombinant or can be isolated from a variety of cellular or animal sources. In one embodiment of the present invention, the BMP, in any form, that is contacted with the at least one protease is a recombinant BMP. In one specific embodiment, the recombinant BMP is contacted with a metalloproteinase to generate the modified BMP peptides of the present invention. In a more specific embodiment, the recombinant BMP is contacted with a collagenase to generate the novel, truncated BMP peptides of the present invention. In an even more specific embodiment, the recombinant BMP that is contacted with a collagenase is a recombinant mature form of BMP. In a still more specific embodiment; recombinant mature BMP is contacted with a collagenase and/or clostripain to generate the novel, truncated BMP peptides of the present invention. In another specific embodiment, recombinant mature BMP is contacted with a trypsin or dispase to generate the novel, truncated BMP peptides of the present invention.

Once treated with at least one protease, in some embodiments, the resulting peptides can be isolated and purified using routine methods in the art. Examples of purification methods include, but are not limited to size exclusion chromatography, high-performance liquid chromatography, ion exchange chromatography, electrophoresis, Western blotting and subsequent processing of the membrane. In one embodiment of the present invention, the resulting peptide that is purified after protease treatment comprises any of the amino acid sequence of SEQ 1D NO:16-35. In other embodiments, after being treated with a protease, the resulting peptides are not isolated or purified and are administered to a cell in the presence of the protease. In another embodiment, the resulting peptide is isolated or purified and then is administered to a cell with a protease. In again another embodiment, after being treated with a protease, without being isolated or purified, the resulting peptides are administered to a cell in the presence of the protease, then another protease is administered together.

The modified growth factor peptides of the present invention may also be prepared by synthetic methods using solid-phase synthetic techniques. The synthesized polypeptides may be re-natured into correct folding pattern under appropriate conditions and bioactive dimmers can be induced from monomers using appropriate buffers and conditions. The correctly folded dimers maybe further separated from monomers using appropriate column to increase the yield of functional bioactive factors.

Regardless of method of preparation, be it recombinantly, enzymatically or synthetically, the novel modified growth factors, as monomers or dimers, can be prepared as a composition. In one embodiment, the composition is a pharmaceutical composition. For example, one or more cofactors may be added to the truncated mature bioactive factor of the present invention to form a composition. Cofactors that may be added include, but are not limited to, heparin, hyaluronic acid, a fibronectin, an elastin, a laminin, albumin, a proteoglycan, collagen, gelatin, a divalent cation, calcium chloride, zinc sulfate, magnesium chloride, sodium bicarbonate, sodium chloride, sodium acetate, or sodium phosphate. In some embodiments, a protein or a protein fragment may be added as a cofactor to the modified growth factor peptides of the present invention.

The compositions, or pharmaceutical compositions, comprising the nucleic acid molecules or polypeptides typically comprise the nucleic acid molecule or protein and a pharmaceutically acceptable carrier. As used herein, "pharmaceutically acceptable carrier" or "pharmaceutical carrier" is intended to include any and all solvents, dispersion media, coatings, antibacterial and antifungal agents, isotonic and absorption delaying agents, and the like, compatible with pharmaceutical administration. The nature of the pharmaceutical carrier or other ingredients will depend on the specific route of administration and particular embodiment of the invention to be administered. Examples of techniques and protocols that are useful in this context are, inter alia, found in Remington: The Science and Practice of Pharmacy (2010), Lippincott, Williams & Wilkins. Examples of such pharmaceutical carriers or diluents include, but are not limited to, water, saline, Ringer's solution, dextrose solution and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include oral and parenteral (e.g., intravenous, intradermal, subcutaneous, inhalation, transdermal (topical), transmucosal and rectal administration). Solutions or suspensions used for parenteral, intradermal or subcutaneous application can include, but are not limited to, a sterile diluent such as water for injection, saline solution, fixed oils, polyethylene glycols, glycerine, propylene glycol or other synthetic solvents, antibacterial agents such as benzyl alcohol or methyl parabens, antioxidants such as ascorbic acid or sodium bisulfite, chelating agents such as ethylenediaminetetraacetic acid, buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable pharmaceutical carriers include physiological saline, bacteriostatic water, Cremophor EL™ (BASF) or phosphate buffered saline (PBS). In all cases, the compositions must be sterile and should be fluid to the extent that easy syringeability exists. It must be stable under the conditions of manufacture and storage and must be preserved against the contaminating action of microorganisms such as bacteria and fungi. The pharmaceutical carrier can be a solvent or dispersion medium containing, for example, water, ethanol, polyol (for example, glycerol, propylene glycol and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it may be desirable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., the modified growth factor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutical carrier. They can be enclosed in gelatin capsules or compressed into tablets. For the purpose of oral therapeutic administration, the active compound can be incorporated with excipients and used in the form of tablets, troches or capsules. Oral compositions can also be prepared using a fluid phainiaceutical carrier for use as a mouthwash, wherein the compound in the fluid pharmaceutical carrier is applied orally and swished and expectorated or swallowed. Pharmaceutically compatible binding agents, and/or adjuvant materials can be included as part of the composition. The tablets, pills, capsules, troches and the like may contain any of the following ingredients, or compounds of a similar nature, such as but not limited to a binder, such as microcrystalline cellulose, gum tragacanth or gelatin, an excipient such as starch or lactose, a disintegrating agent such as alginic acid, Primogel or corn starch, a lubricant such as magnesium stearate or Sterotes, a glidant such as colloidal silicon dioxide, a sweetening agent such as sucrose or saccharin, or a flavoring agent such as peppermint, methyl salicylate or orange flavoring.

In one embodiment, the active compounds are prepared with pharmaceutical carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These compositions can be prepared according to methods known to those skilled in the art, for example, as described in U.S. Pat. No. 4,522,811. It is especially advantageous to foimulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit fours of the invention are dictated by and directly dependent on the unique characteristics of the active compound and the particular therapeutic effect to be achieved.

The pharmaceutical compositions can be included in a container, pack or dispenser together with instructions for administration.

The dosage of BMP peptides or the composition comprising the BMP peptides and a protease will depend on the disease state or condition to be treated and other clinical factors such as weight and condition of the human or animal and the route of administration of the compound. For treating human or animals, between approximately 0.005 mg/kg of body weight to 500 mg/kg of body weight of the compound can be administered. Therapy is typically administered at lower dosages and is continued until the desired therapeutic outcome is observed.

Methods of determining the dosages of compounds to be administered to a patient and modes of administering compounds to an organism are disclosed in, for example, WO 96/22976. Those skilled in the art will appreciate that such descriptions are applicable to the present invention and can be easily adapted to it.

The proper dosage depends on various factors such as the type of disease being treated, the particular composition being used and the size and physiological condition of the patient. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

The invention also relates to methods of altering intracellular signaling of a cell, comprising contacting the cells with at least one of the modified peptides or the composition comprising the modified peptide and a protease, wherein the cell possesses a receptor that specifically binds to the modified growth factors of the present invention. The peptides utilized in the methods can be in monomeric, homodimeric or heterodimeric form. The specific binding of the modified growth factors to its receptor will, in turn, initiate the intracellular signaling cascade that is normally associated with the unmodified forms of the growth factor. For example, the "mature" form of BMP normally binds to its receptor complex including type I and type II receptors. The receptor phosphorylates cytoplasmic targets that include, but is not limited to, the Smad family of proteins. Smads are a class of proteins that function as intracellular signaling effectors for the TGF-β superfamily of secreted polypeptides. The activated BMP type I receptors will phosphorylate Smad1, Smad 5, and/or Smad 8. Phosphoiylated Smad 1, 5, and 8 proteins, in turn, form a complex with Smad 4 and then translocate into the nucleus and interact with the transcription factors that regulate the expression of target genes.

Accordingly, the present invention provides methods of stimulating phosphorylation of Smad 1, Smad 5 and/or Smad 8 in a cell comprising contacting the cell(s) with at least one modified growth factor of the invention. The peptides utilized in the methods can be in monomeric, homodimeric or heterodimeric form. The activity of the novel peptides with respect to phosphorylating the Smad proteins may or may not be altered relative to the normal, mature growth factor. For example, the novel modified growth factors may increase or decrease phosphorylation of Smad 1, 5 and/or 8 compared to receptor binding of normal, mature growth factor. As another example, the novel modified growth factors may bind tighter or looser to its receptor (lower Kd) compared to receptor binding of normal, mature growth factor. One of skill in the art can readily determine if a particular protein is more or less phosphoylated over control groups using well known techniques such as transcription of reporter genes, ELISA assays, etc. Additional methods of the present invention comprise assessing the levels of Smad phosphorylation, for example, Smad 1, Smad 5 or Smad 8, both before and after contacting the cell(s) with the novel peptides of the present invention and determining the increase or decrease of Smad phosphorylation in response to the novel peptides of the present invention.

In another embodiment, the present invention provides methods of stimulating promoter activity in a cell or population of cells, where the promoter is responsive to activated Smad complexes, with the methods comprising contacting the cell(s) with at least one modified growth factor peptide of the present invention. The peptides utilized in the methods can be in monomeric, homodimeric or heterodimeric form. One of skill in the art would be aware of promoters that respond to activated. Smad complexes. See, for example, Massague (2000) Cell, 103:295-309. The activity of the novel peptides with respect to stimulating Smad-responsive promoters may or may not be altered relative to the normal, mature growth factor. For example, the novel modified growth factors may increase or decrease activation of Smad-responsive promoters compared to receptor binding of normal, mature growth factor. One of skill in the art can readily determine if a promoter is more or less activated over control groups using well known techniques such as transcription of reporter genes, ELISA assays, etc. Additional methods of the present invention comprise assessing the activity of a Smad-responsive promoter both before and after contacting the cell(s) with the novel peptides of the present invention and determining the increase or decrease of the promoter in response to the novel peptides of the present invention.

As used herein, "contacting," when used in connection with the methods of the present invention means bringing the novel peptides, in monomeric, homodimeric or heterodimeric form, in proximity to the target cells such that a specific binding event or a biological effect is possible. Thus, contacting can include adding the novel peptides in culture medium and applying the culture medium to cells in culture. Contacting also encompasses transfecting a cell with at least one vector described herein and allowing the cell to produce the modified growth factor. Of course, contacting would also include administration of the modified growth factor peptides, or pharmaceutical compositions thereof, of the present invention to cells in an intact organism. Compositions for administering the novel peptides of the present invention have been described herein.

As used herein, "administering," and "administer" are used to mean introducing at least one compound comprising at least one novel modified growth factor peptide into a subject. The peptides utilized in the administration methods can be in monomeric, homodimeric or heterodimeric form. When administration is for the purpose of treatment, the substance is provided at, or after the onset of, a symptom or condition in need of treatment. The therapeutic administration of this substance serves to attenuate any symptom, or prevent additional symptoms from arising. When administration is for the purposes of preventing a condition from arising ("prophylactic administration"), the substance is provided in advance of any visible or detectable symptom. The prophylactic administration of the substance serves to attenuate subsequently arising symptoms or prevent symptoms from arising altogether. The route of administration of the compound includes, but is not limited to, topical, transdermal, intranasal, vaginal, rectal, oral, subcutaneous intravenous, intraarterial, intramuscular, intraosseous, intraperitoneal, epidural and intrathecal as previously disclosed herein.

Furthermore, the methods would also include coadministering one or more substances in addition to the novel peptides of the present invention. The term "coadminister" indicates that each of at least two compounds is administered during a time frame wherein the respective periods of biological activity or effects overlap. Thus the term includes sequential as well as coextensive administration of the compounds of the present invention. And similar to administering compounds, coadministration of more than one substance can be for therapeutic and/or prophylactic purposes. If more than one substance is coadministered, the routes of administration of the two or more substances need not be the same.

The invention also relates to methods of promoting osteoinductivity, with the methods comprising contacting cells with at least one modified growth factor peptide of the present invention, or compositions described herein, As used herein, "osteoinductivity" can refer to causing cells to differentiate into cells that are more osteoblast-like in phenotype, or the term can refer to increasing the proliferation of osteoblasts, or both. The cells, prior to contact with the modified growth factor peptide(s) of the present invention, may be undifferentiated or partially differentiated cells. The cells may be present in culture or in a tissue, organ or portion thereof or in an organism. The osteoinductive activity of the novel peptides may or may not be altered, including but not limited to, enhanced activity, relative to the normal, mature growth factor.

The invention also relates to methods of promoting chondroinductivity, with the methods comprising contacting cells with at least one modified growth factor peptide of the present invention, or compositions described herein. As used herein, "chondroinductivity" can refer to causing cells to differentiate into cells that are more chondrocyte-like in phenotype, or the term can refer to increasing the proliferation of chondrocytes, or both. The cells, prior to contact with the modified growth factor peptide(s) of the present invention, may be undifferentiated or partially differentiated cells. The cells may be present in culture or in a tissue, organ or portion thereof or in an organism. The chondroinductive activity of the novel peptides may or may not be altered, including but not limited to, enhanced activity, relative to the normal, mature growth factor.

The invention also relates to methods of promoting ligament/tendon differentiation, with the methods comprising contacting cells with at least one modified growth factor peptide of the present invention, or compositions described herein. As used herein, "ligament/tendon differentiation" can refer to causing cells to differentiate into cells that are more ligament and/or tendon-like in phenotype, or the term can refer to increasing the proliferation of ligament and/or tendon, or both. The cells, prior to contact with the modified growth factor peptide(s) of the present invention, may be undifferentiated or partially differentiated cells. The cells may be present in culture or in a tissue, organ or portion thereof or in an organism. The ligament/tendon differentiation activity of the novel peptides may or may not be altered, including but not limited to, enhanced activity, relative to the normal, mature growth factor.

For example, the invention provides for growing and/or culturing cells in the presence of one or more modified growth factor peptides, or compositions described herein. "Growing and/or culturing cells in the presence of" includes traditional cell culture methods as well as placing cells in the presence of the modified growth factors in any setting, such as in natural or synthetic matrices or tissues. The cells may be mammalian, such as but not limited to human, bovine, porcine, murine, ovine, equine, canine, feline and others. In some embodiments, the cells may be mesenchymal stem cells, such as adipose-derived stem cells, embryonic stem cells, progenitor cells, differentiated cells, undifferentiated cells, and/or pluripotent stein cells. Appropriate cells may also include, but are not limited to cells of the ectodermal lineage, cells of the mesodermal lineage, and cells of the endodermal lineage. Examples of cells of the ectodermal lineage include but are not limited to keratinocytes, osteoblasts, chondrocytes, neurons. Examples of cells of the mesodermal lineage include but are not limited to myoblasts, adipocytes, fibroblasts, endothelial cells, or stromal cells. Examples of cells of the endodermal lineage include but not limited to epithelial cells of the auditory tube, the respiratory tract, such as trachea, bronchi, and alveoli of the lungs, the gastrointestinal tract, the urinary bladder and epithelial cells lining all glands. The cells may also be primary cells derived from tissues or organs. Appropriate cell lines used in the present invention may include but are not limited to mesenchymal cell lines, preosteoblastic cell lines, osteoblastic cell lines, and chondroblastic cell lines. The cells to which the modified growth factor peptides have been administered may be placed directly into a tissue, organism or other setting such as a matrix, including, but not limited to, bone matrices.

In some embodiments, the cells may be derived from autologous or allogeneic sources. The cells may be differentiated cells including chondrocytes, osteoblasts, osteoclasts, endothelial cells, epithelial cells, fibroblasts, and periosteal cells. Additionally, the cells may be totipotent, pluripotent, multipotent, progenitor, or adult somatic stem cells. The stem cells may be derived from embryos, placenta, bone marrow, adipose tissue, blood vessel, amniotic fluid, synovial fluid, synovial membrane, pericardium, periosteum, dura, peripheral blood, umbilical blood, menstrual blood, teeth, nucleus pulposus, brain, skin, hair follicle, intestinal crypt, neural tissue, muscle. The stem cells may be derived from skeletal muscle, smooth muscle, and cardiac muscle. The stem cells may be derived from genetic reprogramming of mature cells, such as induced pluripotent stem cells (iPSCs).

Any cell described herewith may be cultured with one or more modified growth factorss or compositions described herein for between about 15 minutes and about 4 weeks, about 2 hours and about 2 weeks, about 2 hours and about 1 week, about 2 hours and about 72 hours, about 24 hours and about 72 hours, or about 24 hours and about 96 hours, at between about 20° C. and about 40° C. or about 30° C. and about 37° C., in an atmosphere containing between about 1% $CO_2$ and about 10% $CO_2$ or about 4% $CO_2$ and about 6% $CO_2$, in certain embodiments. In some embodiments of the present invention, cells may be cultured in the presence of one or more modified growth factors and/or (1) a tissue or an organ, (2) a matrix, or (3) a combination thereof. Cells that have been cultured in the presence of one or more modified growth factors in a cell culture medium may subsequently be applied to a matrix, a tissue, an organ or a combination thereof, in certain embodiments.

In some embodiments, treated cells are cryopreserved. Cryopreservation agents may be used to preserve treated cells, in certain embodiments. In some embodiments, treated cells are seeded onto a matrix, and the cell-seeded matrix may be preserved using at least one cryopreservation agent. At least one cofactor may be added to treated cells, in some embodiments. Cofactors that may optionally be used are heparin, hyaluronic acid, a fibronectin, an elastin, a laminin, a proteoglycan, collagen, or gelatin, among others. In certain embodiments, a divalent cation, calcium chloride, zinc sulfate, magnesium chloride, sodium bicarbonate, sodium chloride, or sodium phosphate may be added as a cofactor to treated cells. In some embodiments, a protein or a protein fragment may be a cofactor that is added to treated cells. In further embodiments, a protease described herein may be a cofactor that is added to treated cells. Alternatively, the treated cells can be kept at a low temperature (e.g. 4° C.) or room temperature for 24-48 hours without cryopreservation.

In certain embodiments, treated cells that have been cryopreserved are optionally revived at a temperature between about 10° C. and about 37° C. before being applied to a tissue or an organ defect, a tissue, an organ, a matrix, or a mixture of two or more of these. In certain embodiments, treated cells may be combined with one or more body fluid, for example blood, platelet-rich plasma, platelet-poor plasma, plasma, bone marrow, and cord blood, among others, and an isotonic, hypotonic, or hypertonic solution, for instance saline, or Lactated ringer solution, and others, before they are used to treat a tissue or an organ defect. In some embodiments, treated cells may be applied to a tissue or an organ defect by injecting or inserting the cells between tissues or organs, or placing the cells on top of the defect. Modified growth factors may be administered to cells in vitro, in vivo, or in situ, in some embodiments. The modified growth factors may be administered to cells that are in tissue or organ or that have been isolated from tissues or organs, in some embodiments. In certain embodiments, at least one modified growth factor or compositions described herein may be administered to cells in (1) a cell culture medium, (2) a tissue or an organ, (3) a matrix, or (4) a combination of two or more of these.

There are a variety of osteoblast, chondrocyte, ligament/tendon differentiation markers that can be measured to assess osteoinductivity, chondroinductivity, or ligament/tendon differentiation, respectively. For example, cells express alkaline phosphatases during the early stages of differentiation toward osteoblast lineages. Therefore, in vitro alkaline phosphatase assays may be used to evaluate osteoinductivity in cells contacted with the modified growth factor peptide(s) of the present invention. The ability of the modified growth factor peptide(s) of the present invention to stimulate or induce the alkaline phosphatase expression in an otherwise non-bone forming cells, such as myoblast (C2C12 cells), would indicate that the modified growth factor peptide(s) of the present invention has osteoinductive activity. In these assays, cells cultured without added growth factors of any kind and without added modified growth factor peptide(s) of the present invention are used as negative controls to show that the baseline alkaline phosphatase expression on non-bone forming cells. The baseline of the osteoblastic markers in the negative control need not be zero, meaning that the cells in the negative control group may have at least some level of phenotypic marker(s). Accordingly, an "osteoinductive" peptide of the present invention would simply cause an increase in the osteoblastic markers in experimental cells over control. Similarly, chondrocyte markers, including but not limited to type X collagen, type II collagen, Sox 9, Aggrecan. Matrilin-1 and CEP-68, to name a few, can be used to assess chondroinductive potential. Moreover, ligament/tendon markers, including but not limited to scleraxis, can be used to assess ligament/tendon differentiation potential.

Moreover, osteoinductivity, chondroinductivity, and ligament/tendon differentiation may be determined in tissue culture by investigating the ability of the modified growth factor peptide(s) of the present invention to differentiate or induce osteoblast phenotype, chondrocyte phenotype, ligament/tendon cell phenotype in cultured cells, such as primary cells, cell lines, or explants. For example, the cells may display increased production of a marker characteristic of osteoblasts and/or chondrocytes, such as alkaline phosphatase, etc. For example, the osteoinductive, chondroinductive, ligament/tendon differentiation potentials of the modified growth factors may be more than 0.2, 0.4, 0.6, 0.8, 1, 2, 3, 4, 5, 6, 7, 8, 9 or 10 times greater than those of the unmodified growth factors. In another example, the osteoinductive, chondroinductive, ligament/tendon differentiation potentials of the modified growth factors may be more than 10, 20, 30, 40, 50, 60, 70, 80, 90, 100, 500 or even 1000 times greater compared to those of the unmodified growth factors. Of course, this indicates that lower concentrations of modified growth factor, compared to unmodified growth factor are required to achieve the same effects.

Osteoinductivity, chondroinductivity, ligament/tendon differentiation, for assessing the bone, cartilage, ligament or tendon forming potential induced by the modified growth factor peptide(s) of the present invention in a location such as muscle, may also be evaluated using a suitable animal model. For example, intramuscular implantation into a rodent has been used as a model to assess osteoinductive activity of bioactive factors.

The invention also relates to methods of promoting proliferation or maintaining the differentiated state or preventing de-differentiation of osteoblasts, chondrocytes, ligament cells, tendon cells and/or any cell type disclosed herein comprising administering to the osteoblasts, chondrocytes, ligament cells, or tendon cells the modified growth factor peptides or compositions described herein. The proliferative activity of the novel peptides may or may not be altered, including but not limited to, enhanced activity, relative to the normal, mature growth factor.

Mitogenicity may be assessed by investigating cell proliferation induced by the modified growth factor peptides using various in vitro assays that measure metabolic activity, such as MTT [3-(4,5-dimethylthiazol-2-yl)-2,5-diphenyltetrazolium bromide] assay, alamarBlue® assay, and others. The alamarBlue® assay uses a non-cytotoxic reduction-oxidation indicator to measure cell metabolic activity, making it a nondestructive assay for assessing the mitogenic activity of the modified growth factors. Proliferation can also be assessed by measuring DNA quantification, such as by using a PicoGreen™ DNA assay, radioactive labeling of DNA synthesis, such as [$^{3H}$]thymidine labeling or BrdU incorporation. Proliferation can also be assessed via manual cell counting, such as using a trypan blue hemacytometer.

The invention also relates to methods of increasing a cellular growth factor activity comprising administering to the cell at least one protease and the growth factor described herein. The protease is a protease described herein, including, but not limited to, collagenase, clostripain, dispase, trypsin, cathepsin, MMP-1, MMP-13, and a mixture thereof. In some embodiments, the growth factor comprises the mature growth factor and/or the modified growth factor described herein. The cell is a cell described herein, including, but not limited to, differentiated cells, adult stem cells, progenitor cells, and pluripotent stein cells. As explained previously, the modification of the growth factors as disclosed herein also enhances the activity of BMP. In certain embodiments, administering the protease along with the modified growth factor described herein further enhances the activity of the modified growth factor, such as an osteoinductive, chondroinductive activity, ligament/tendon differentiation potential.

In some embodiments, the addition of the protease described herein into the composition enhances stability of the growth factor in the same composition. As described previously, the modification of the growth factors as disclosed herein also enhances the stability of the growth factor. In certain embodiments, the addition of the protease into the composition comprising the modified growth factor further enhances the stability of the modified growth factor.

In additional embodiments, the composition administered to a cell in increasing a cellular growth factor activity comprises two or more protease. In some embodiments, a second protease can be mixed into the composition comprising the protease and the growth factor or can be administered separately from the composition comprising the protease and the growth factor.

The invention further relates to tissue or organ repair or regeneration compositions comprising (i) at least one modified growth factor peptide or the compositions of the present invention and (ii) a tissue, an organ, a matrix and/or a mixture of two or more thereof. The tissue or organ repair composition may comprise—bone, cartilage, and/or connective tissue.

An implantable biocompatible matrix for use with the compositions described herein can function as a suitable delivery or support system for the modified growth factor peptides. A biocompatible matrix should be non-toxic, non-eliciting or stimulating severe inflammatory response or immunological rejections, and devoid of other undesired reactions at the implantation site. Suitable matrices may also provide for release of the modified growth factor peptides, for example, to promote a slow, sustained release over time at the implantation site. In one embodiment, the matrix is a bone matrix or cartilage or connective tissue. In addition to its common, ordinary meaning, "administering to the matrix" includes embedding into the matrix or matrices host cells capable of producing at least one modified growth factors peptide. In another embodiment, the invention provides for methods of treating cells with at least one modified growth factor peptide or compositions described herein and implanting these treated cells into a matrix, such as, but not limited to a bone matrix or cartilage.

Suitable matrices include, but are not limited to, porous scaffolds into which bone cells or progenitor cells may migrate. Osteogenic or chondrogenic cells, i.e., cells involved in the process of deposition of new bone material or cartilagenous material, respectively, can often attach to such porous matrices, which can then serve as scaffolding for bone and cartilage tissue growth. Cells involved in the process of deposition of new ligament or tendon material can also attach to such porous matrices. For certain applications, the matrix should have sufficient mechanical strength to maintain its three dimensional structure and help support the immobilization of the bone segments being united or grafted together. Porous matrices which provide scaffolding for tissue growth can accelerate the deposition of new bone or the rate of bone growth and are said to be "osteoconductive." Osteoconductive matrices are especially useful in the pharmaceutical compositions described herein. Porous matrices which provide scaffolding for tissue growth can accelerate the deposition of new cartilage or the rate of cartilage growth and are said to be "chondroconductive." Osteoconductive matrices are especially useful in the phaii-naceutical compositions described herein. Chondroconductive matrices are especially useful in the pharmaceutical compositions described herein. The osteoinductive or chondroinductive activity of the novel peptides may or may not be altered, including but not limited to, enhanced activity, relative to the normal, mature growth factor. Thus, the osteoconductive or chondroconductive activity of the treated matrices of the present invention may be enhanced compared to matrices not treated with modified growth factor. Of course, the matrices are considered to be osteoconductive or chondroconductive if cells within the matrix begin to differentiate into more osteoblast-like or chondrocyte-like appearing or functional cells, respectively.

Matrices can be derived from natural sources or they can be synthetic or a mixture of both. Matrices from natural sources may also comprise natural polymers, including, but not limited to, collagen, hyaluronic acid, alginate, albumin, fibrinogen-fibrin, chitosan, elasin, laminin, connective tissues, intervertebral disc, cortical or cancellous bone, demineralized or mineralized bone, fascia lata, dermis, muscle, ligament, tendon, cartilage including articular/hyaline cartilage, elastic cartilage, and fibrocartilage, a mixture thereof, and mixture of reconstituted tissue. Matrices from synthetic sources refer to any material not produced by living organisms, which may include, not limited to, the synthetic material made up of organic components, inorganic components, or a mixture thereof. In some embodiments, a synthetic matrix may comprise an organic synthetic polymer, such as poly(lactic-co-glycolic acid), polycaprolactone (PCL), polyglycolic acid (PGA), polylactic acid (PLA), polyhydroxybutyrate (PHB), Poly(ethylene glycol) (PEG), poly(ethylene oxide) (PEO)), and others. In some embodiments, a tissue, an organ, or matrix comprising at least one of alginate, chitosan, collagen, gelatin, hyaluronic acid, a fibronectin, an elastin, a laminin, and a proteoglycan may be employed. In certain embodiments, a matrix comprising inorganic components, such as hydroxyapatite, calcium sulfate, octacalcium phosphate, calcium phosphate, macroporous calcium metaphosphate ceramic, β-tricalcium phosphate, metal, metal alloy, and others, may be used. A matrix used in certain embodiments of the present invention may be prepared by demineralizing, decellularizing or devitalizing a tissue or an organ and cells may be seeded onto the matrix.

In some embodiments, at least one modified growth factor compositions described herein may be applied to the matrix and may be incubated at conditions permitting the generation of a treated matrix. In some embodiments, incubation may be carried out at about 40° C. or lower, or between about 10° C. and about 37° C., or about 20° C. and about 37° C. Incubation may be carried out for between at least about 2 minutes and about 120 minutes, about 3 minutes and about 100 minutes, about 4 minutes and about 80 minutes, about 5 minutes and about 60 minutes, and about 5 minutes and about 30 minutes in certain embodiments. Incubation may be performed under static or dynamic conditions, such as with agitation, shaking, stirring, mixing, horizontal motion, rocking, and others.

In some embodiments of the present invention, a matrix may be lyophilized before at least one modified growth factor or compositions described herein are administered to it. In certain embodiments, one or more modified growth factors may be administered to a matrix, and the treated matrix may be subsequently lyophilized. The lyophilized, treated matrix can then be rehydrated before it is used. Further, the cells can be seeded onto the matrix before implantation.

Examples of suitable osteoconductive, chondroconductive matrices include but are not limited to, collagen (e.g., bovine dermal collagen), fibrin, calcium phosphate ceramics (e.g., hydroxyapatite and tricalcium phosphate), calcium sulfate, guanidine-extracted allogenic bone and combinations thereof. A number of suitable matrices are commercially available, such as Collograft™ (Collagen Corporation), which is a mixture of hydroxyapatite, tricalcium phosphate and fibrillar collagen, and Interpore™ (Interpore International), which is a hydroxyapatite biomatrix formed by the conversion of marine coral calcium carbonate to crystalline hydroxyapatite.

A number of synthetic biodegradable polymers can serve as osteoconductive or chondroconductive matrices with sustained release characteristics. Descriptions of these polymers can be found in Behravesh (1999) Clinical Orthopaedics 367, S118 and Lu (2000) Polymeric Delivery Vehicles for Bone Growth Factors in Controlled Drug Delivery: Designing Technologies for the Future, Park and Mrsny eds., American Chemical Society. Examples of these polymers include polya-hydroxy esters such as polylactic acid/polyglycolic acid homopolymers and copolymers, polyphosphazenes (PPHOS), polyanhydrides and polypropylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson (1997) Adv. Drug Deliv. Rev. 28:5. The incorporation of PEG into the polymer as a blend to form microparticle matrices allows further alteration of the release profile of the active ingredient (see Cleek (1997) J. Control Release 48, 259). Ceramics such as calcium phosphate and hydroxyapatite can also be incorporated into the formulation to improve mechanical qualities.

In one embodiment, the matrices used in the compositions and methods of the present invention are bone matrices. As used herein, a bone matrix is a matrix derived from or including elements of natural bone. In some embodiments, the natural bone is mineralized, partially demineralized, demineralized, cancellous, cortical, or cortical cancellous bone. The bone matrices used herein may or may not include additional synthetic components not typically found in bone tissue. Other embodiments include compositions and methods utilizing a matrix derived from cartilage, other soft tissues such as the dermis, connective tissue, fascia, small intestine submucosa, serous membrane, pericardium, tendon, ligament, muscle, adipose tissue, myelin, blood vessels, base membrane, amniotic membrane and others. A matrix prepared from hyaline cartilage, fibrocartilage or elastic cartilage, may be employed in some embodiments. A matrix may be prepared from hyaline cartilage found in the condyle, tibial plateau, femoral head, humeral head, costal cartilage, or fibrocartilage found in intervertebral discs, or elastic cartilage found in the epiglottis or ear. In certain embodiments, a matrix derived from natural sources that has been optionally cleaned, disinfected, chemically modified, decellularized, particulated, homogenized, lyophilized, gamma irradiated, and/or plasticized may be used. Any of the matrices used herein may or may not include additional synthetic components not typically found in such tissue.

In one specific embodiment, the bone matrices or cartilage matrices may be demineralized or decellularized, respectively. Examples of demineralized matrices and methods of making are described in U.S. Pat. No. 6,189,537 and 6,305,379.

The matrix, tissue, or organ used in certain embodiments of the present invention may be in the form of a powder, particulates, sheets, fibers, gels, putties, paste, blocks, cylinders, sponges, meshes, films, slices, curls, flakes, or wedges, among others. In certain embodiments of the present invention the matrix, tissue, or organ comprising the modified growth factor peptide(s) may be in the form of a powder, fibers, putty, or a sponge. In further embodiments, the sponge can include, for example, the implant having sponge-like structures disclosed in the co-pending, commonly-assigned patent application PCT/US09/04556 entitled "Composition for a Tissue Repair Implant and Methods of Making the Same" filed on Aug. 7, 2009. The treated matrices can be used in any of the methods of the present invention.

The invention also relates to methods of increasing or promoting osteogenesis, chondrogenesis, or ligament/tendon genesis in cells. The methods may comprise treating the cells in matrices with at least one of the modified growth factor peptides, or compositions described herein. As used herein, "osteogenesis" is the deposition new bone material or formation of new bone, including, but not limited to, intramembranous osteogenesis and endochondral osteogenesis. As used herein, "chondrogenesis" is the deposition new cartilage material or formation of new cartilage. As used herein, "ligament/tendon genesis" is the deposition new ligament and/or tendon material or formation of new ligament and/or tendon. The osteogenic, chondrogenic, ligament, or tendon inducing activity of the novel peptides may or may not be altered, including but not limited to, enhanced activity, relative to the normal, mature growth factor. The cells to which the modified growth factors may be administered include cells in any tissue in which bone, cartilage, ligament, or tendon formation is desired, such as, but not limited to, bone, cartilage, ligament, muscle, tendon, etc.

The invention also relates to methods of treating a tissue or organ defect or injury, for example, a musculoskeletal, dental or soft-tissue defect or injury, in an animal comprising administering (1) cells cultured in the presence of one or more modified growth factors, or compositions described herein and/or (2) one or more modified growth factors, or compositions described herein to the tissue or organ defect (e.g. osseous defects, defects in cartilage, ligament, tendon, spine disk, and tendon insertion site to bone).

The invention further relates to methods of treating a tissue or an organ defect or injury, for example a musculoskeletal, dental or soft-tissue defect, in an animal by applying a treated matrix to the defect, and application to the defect may be accomplished by injecting the treated matrix into the defect, inserting the treated matrix between tissue or organ, or placing the treated matrix on top of the defect. The present invention is also directed to treating a defect or injury in an organ in a similar manner. At least one cofactor may be added to a treated matrix, such as a matrix comprising a modified growth factor, in some embodiments.

In yet another embodiment, cells may be seeded onto a treated matrix. The cells seeded on the treated matrix can be any cell, such as but not limited to, osteoblasts, chondrocytes, ligament cells, tendon cells, progenitor cells, and stem cells disclosed herein or otherwise known in the art. The seeded cells may be allowed to proliferate and possibly attach to the matrix. Methods of seeding cells onto matrices, such as collagen, are well known in the art. Alternatively, cells may first be treated with at least one modified growth factor or compositions described herein and the treated cells may then be seeded onto a treated or untreated matrix.

Any of the methods of the present invention can be perfouued in virtually any setting, such as an in vivo, ex vivo, in situ or in vitro setting. For example, methods of promoting osteogenesis, chondrogenesis, or tendon/ligament inducing activities in cells may be performed in cell culture, may be performed in seeded cells on matrix, or may be performed in an intact organism. Moreover, any combination of any two or more of any of the embodiments described herein are contemplated.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety.

The following examples are illustrative and are not intended to limit the scope of the invention described herein.

Example 1

Preparation and Sequencing of Modified BMP-2

Collagenase (Sigma Aldrich) was linked to sepharose beads and the un-bound collagenase was removed by extensive washing. Collagenase linked-sepharose beads were used to treat recombinant human BMP-2 (rhBMP-2) with incubation at 37° C. overnight with gentle mixing. The rhBMP-2 had the amino acid sequence of amino acids 283-396 of SEQ ID NO: 1 prior to treatment. The modified mature rhBMP-2 and unmodified mature rhBMP-2 control were separated by SDS-PAGE gel electrophoresis and stained by silver staining. The related bands were cut and sequenced using MALDI-TOF mass spectrometry.

The results of MALDI-TOF mass spectrometry of the collagenase-treated rhBMP-2 sequencing revealed the same 13 amino acids on the C-terminus as the last 13 amino acids of carboxyl-terminus of untreated mature rhBMP-2. The MALDI-TOF sequencing confirms that the collagenase treatment did not truncate the C-terminus of the rhBMP-2.

Example 2

Preparation and Sequencing of Modified BMP-2

The mature rhBMP-2 was treated with trypsin or collagenase in a microcentrifuge tube at a molarity ratio of between about 1:10 and about 100:1 and incubated overnight at 37° C. The treated mature rhBMP-2 was further purified by reverse phase HPLC using a C-18 column. The collected fractions from HPLC were tested for osteoinductive potential using an in vitro alkaline phosphatase assay. The fractions that showed significantly high alkaline phosphatase activities were further separated by SDS-PAGE gel electrophoresis and blotted onto PVDF membrane. Proteins on the PVDF membrane were stained by coomassie blue and the related bands were cut and sent for N-terminal sequencing.

In the Coomassie blue stained PVDF membrane, the fraction B43-44 sample from the trypsin-treated rhBMP-2 and the fraction A42-44 sample from the collagenase-treated rhBMP-2 showed clean bands at around 14-15 kDa.

Nine out of ten amino acids of the N-terminus of the trypsin-treated mature rhBMP-2 and eight out of the ten amino acids of the N-terminus of the collagenase-treated mature rhBMP-2 were detected using Edman degradation chemistry with an ABI Procise® 494 sequencer. The deduced amino acid sequence of the N-terminus of the trypsin-treated rhBMP-2 was SSCKRHPLYV, which is the first 10 amino acids of SEQ ID NO:16 herein, and the deduced amino acid sequence of the N-terminus of the collagenase-treated rhBMP-2 was LKSSCKRHPL, which is the first 10 amino acids of SEQ ID NO:18 herein. The N-tenninus of the trypsin-treated rhBMP-2 matches the untreated mature rhBMP-2 sequence after the 11$^{th}$ amino acid of the N-terminus, indicating that the trypsin cleaved the mature BMP-2 after the first 11 amino acids. Similarly, the N-terminus of the collagenase-treated rhBMP-2 matches the untreated mature rhBMP-2 sequence after the 9$^{th}$ amino acid of the N-terminus, indicating that the collagenase cleaved the mature BMP-2 after the first 9 amino acids. Western blot detected untreated and trypsin or collagenase-treated mature rhBMP-2, and the treated rhBMP-2 was about 1-2 kDa smaller than the untreated rhBMP-2.

Example 3

Osteoinductive Potential of Modified rhBMP-2

Figure 2:
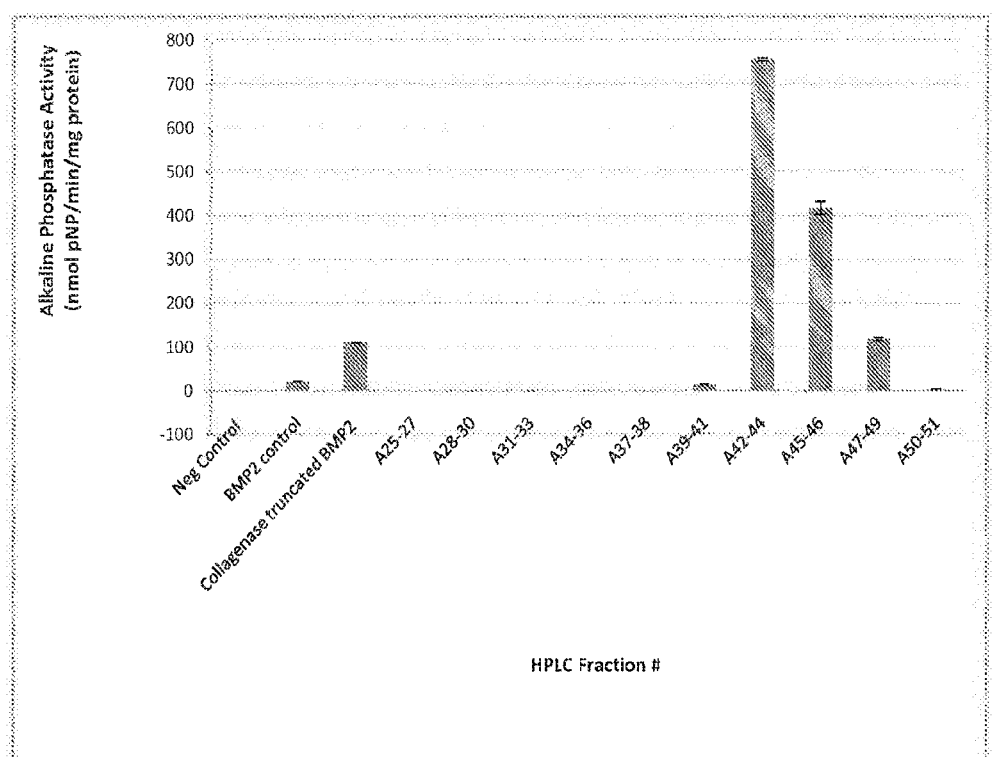
FIG. 2 depicts myoblast expression of alkaline phosphatase after being cultured with rhBMP-2 modified with collagenase. Myoblasts treated with rhBMP-2 modified with collagenase showed significantly greater alkaline phosphatase activity over myoblasts treated with unmodified rhBMP-2. When fractionated via HPLC, fractions A42-44, A45-46 and A47-49 induced the highest levels of alkaline phosphatase in myoblasts.

Alkaline phosphatase is one of the distinctive biological or biologically-derived indicators of osteoinductivity. The AP assay measures the product para-nitrophenol (pNP) at a wavelength of 405 nm after 60 minutes of incubation of the substrate para-nitrophenyl phosphate (pNPP) with a cell lysate at 37° C. The alkaline phosphatase activities of the HPLC fractions from Example 2 are shown in FIGS. 1 and 2. The fraction B43-44 from the trypsin-treated rhBMP-2 and the fraction A42-44 from the collagenase treated rhBMP-2 showed significantly higher alkaline phosphatase activity compared to other HPLC fractions. These results along with FIG. 3 described below demonstrate that trypsin or collagenase-treated mature rhBMP-2, having an N-terminal truncation, facilitates an increase in alkaline phosphatase activity in vitro.

Example 4

Osteoinductive Potential of Modified rhBMP-2 with or without a Protease

C2C12 cells (ATCC CRL-1772), which are from a mouse myoblast cell line, were seeded at a density of 25,000 cells/cm$^2$ in 24-well plates on day one. Collagenase and rhBMP-2 were mixed in microcentrifuge tubes at a molarity ratio of between about 1:10 and about 100:1 and incubated overnight at 37° C. The treated mature rhBMP-2 was aliquoted with or without further HPLC purification described above. The aliquot with further HPLC purification (purified modified BMP2) was quantified by ELISA. The aliquot without further HPLC purification (non-purified modified BMP2) retained the collagenase in the aliquot. The aliquots were used to test the effect of treated mature rhBMP-2 on osteoinductive potential of C2C12 myoblasts.

Each of the rhBMP-2 control, and the purified modified rhBMP-2, and the non-purified modified rhBMP-2 at the same concentration was introduced into wells of the C2C12 cell seeded 24-well plate. C2C12 cells cultured in media alone (without addition of rhBMP-2 or modified rhBMP-2) were used as a negative control.

Figure 3:
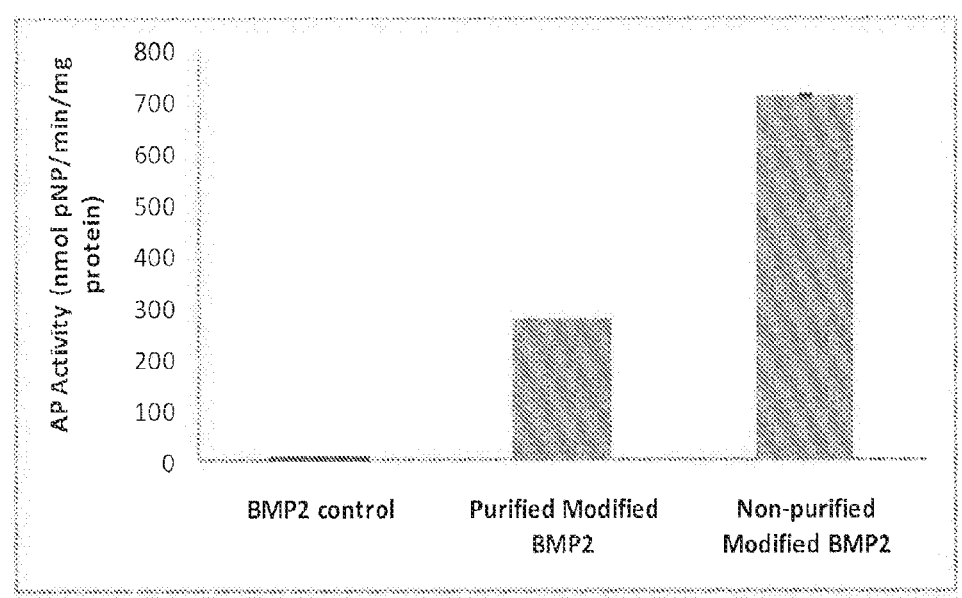
FIG. 3 depicts myoblast expression of alkaline phosphatase after being cultured with rhBMP-2 control, purified modified rhBMP-2 and non-purified modified rhBMP-2.

After 3 days incubation at 37° C., 5% $CO_2$, the AP assay as described above was performed, and the results are shown in FIG. 3. The alkaline phosphatase activity of cells cultured with the purified modified rhBMP-2 or the non-purified modified rhBMP-2 were about 39 times and 103 times higher than that of cells cultured with non-treated rhBMP-2 control, respectively. The alkaline phosphatase activity of cells cultured with non-purified modified rhBMP-2 was about 1.6 times higher than that of cells cultured with purified modified rhBMP-2. Thus, the results demonstrate a significant increase in the alkaline phosphatase activity by administering the non-purified modified rhBMP-2 compared to administering the purified modified rhBMP-2.

Figure 4:
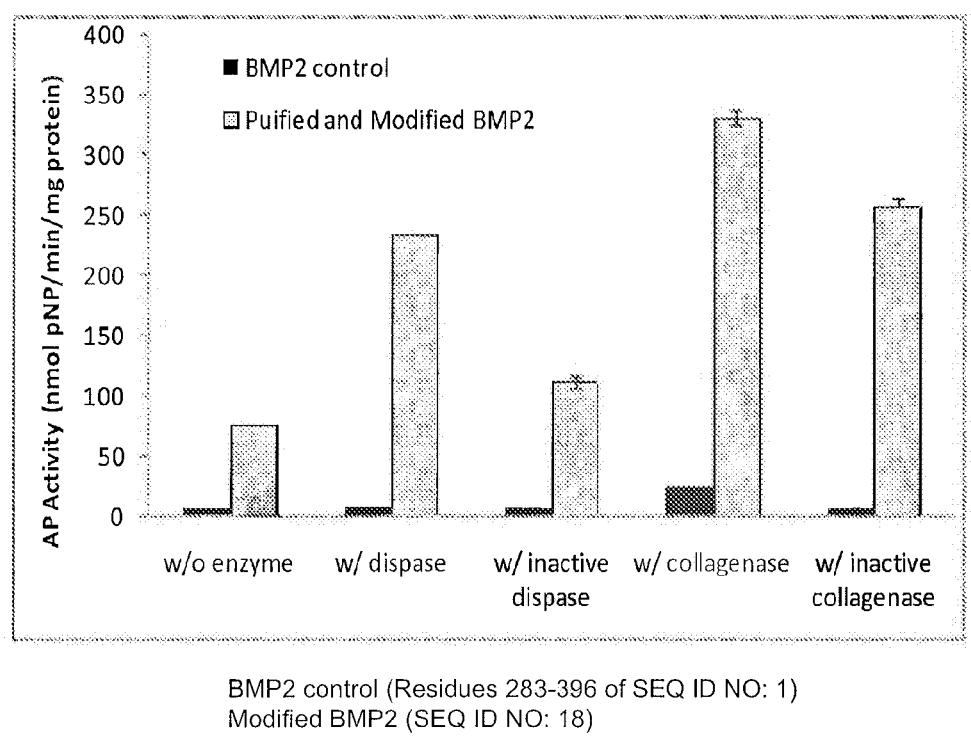
FIG. 4 depicts myoblast expression of alkaline phosphatase after being cultured with rhBMP-2 control and purified modified rhBMP-2 in the presence of no additional protease, dispase, inactive dispase, collagenase, or inactive collagenase.

Further, with another set of C2C12 cells cultured as described above, the purified modified rhBMP-2 was introduced into wells of the C2C12 cell along with 138 ng/mL of active dispase or inactive dispase, or 100 ug/mL collagenase or inactive collagenase. The AP assay as described above was performed, and the results are demonstrated in FIG. 4. The results showed that adding active or inactive dispase or collagenase to the purified modified rhBMP-2 samples also increased the alkaline phosphatase activity.

In addition, rhBMP-2 treated by clostripain, dispase, and the mixture thereof, without further purification, also increased the alkaline phosphatase activity compared to non-modified rhBMP-2 control. In addition, rhBMP-2 treated by BMP1 or MMP13, without further purification, also increased the alkaline phosphatase activity compared to non-modified rhBMP-2 control.

Example 5

Osteoinductive Potential of Modified rhBMP-2 with a Protease

C2C12 cells (ATCC CRL-1772) were cultured as described above. Collagenase and rhBMP-2 were mixed in microcentrifuge tubes at a molarity ratio of between about 1:10 and about 100:1 and incubated overnight at 37° C. with agitation. The treated mature rhBMP-2 was aliquoted, and the aliquots were used to test the effect of treated mature rhBMP-2 on osteogenic potential of C2C12 myoblasts as follows.

For the osteoinductive potential assessment, base media of DMEM containing 1% FBS, 50 µg/mL of ascorbic acid and 10 mM of β-glycerolphosphate was used as a control group. The base media control with the addition of 50 ng/mL of rhBMP-2 was used as the BMP-2 positive control group. The base media control with the addition of 50 ng/mL of modified rhBMP-2 without the purification was used as the test group. The media were added into C2C12 cells seeded on chamber slides and changed every 3-4 days.

After 4 days incubation at 37° C., 5% $CO_2$, photographs were also taken for cell cultures in each group. The nodule formation of C2C12 cells appeared only in modified rhBMP-2 group, but not in the other two control groups.

After 6 or 12 days of incubation, the media was removed from chamber slides and the slides were stained with Alizarin Red S. Alizarin red S has been used to identify calcium-rich deposits by cells in culture or tissue sections, which indicates the effect of osteoinductive material on osteogenic potential of cells.

For the base media control group, no positive Alizarin red S staining was found at any tested time points. For the rhBMP-2 control group, some Alizarin red S staining was detected after 6 or 12 days of incubation. For the modified rhBMP-2 group, after 6 days of incubation, significant amount of nodules stained positive by Alizarin red S. After 12 days of incubation, more Alizarin red S positively stained nodules of larger size were observed in C2C12 cells cultured with modified rhBMP-2 than that in C2C12 cells cultured with unmodified rhBMP-2. This data suggests that modified rhBMP-2 has a significantly greater effect on osteogenic potential of C2C12 myoblasts as compared to the unmodified mature rhBMP-2 control.

Example 6

Alkaline Phosphatase Assay for Cells Cultured with Modified rhBMP-2

Alkaline phosphatase is one of the distinctive indicators of osteoinductivity. C2C12 cells (ATCC CRL-1772), which are from a mouse myoblast cell line, were seeded at a density of 25,000 cells/$cm^2$ in 24-well plates on day one. Collagenase and rhBMP-2 were mixed in microcentrifuge tubes at a molarity ratio of between about 1:10 and about 100:1 and incubated overnight at 37° C. with agitation. On day two, the collagenase-treated rhBMP-2, untreated rhBMP-2 at the same concentration as treated rhBMP-2, or collagenase alone at the same concentration of collagenase used to treat rhBMP-2 was introduced into each well of the C2C12 cell seeded 24-well plate. C2C12 cells cultured without the addition of rhBMP-2 or collagenase were used as a negative control. After 3 days of incubation at 37° C., 5% $CO_2$, cells were collected from the culture plates, and cell lysates were prepared for AP assays and bicinchoninic acid (BCA) total protein assays (BCA reagent available from Pierce Biotechnology). The AP assay was performed as described above. The BCA assay is a detergent-compatible protein assay used for colorimetric detection and quantitation of total protein. The results of the in vitro AP assay are shown in Table IV. The alkaline phosphatase activity of cells cultured with collagenase-treated rhBMP-2 was about 87 times higher than that of cells cultured with untreated rhBMP-2.

TABLE 6

| | Alkaline phosphatase activity of cells | | | |
|---|---|---|---|---|
| Groups | Negative Control | Unmodified rhBMP-2 | Collagenase Control | Modified rhBMP-2 |
| Mean AP activity (nmol pNP/min/mg protein) | 0.86 ± 0.08 | 9.93 ± 0.08 | 1.02 ± 0.29 | 862.31 ± 40.71 |

Example 7

Osteoinductive Potential of Mature rhBMP-2 with the Addition of Protease

C2C12 mouse myoblast cell line (ATCC CRL-1772), were cultured as described above. The mature rhBMP-2 (50 ng/mL, R&D Systems, Inc.), or the same concentration of mature rhBMP-2 with the addition of dispase or collagenase (molarity ratio between about 1:100 and about 100:1) was introduced into wells of the C2C12 cells. C2C12 cells cultured in media alone (without addition of rhBMP-2) were used as a negative control.

After 3 days incubation at 37° C., 5% $CO_2$, an AP assay was performed as described above. The alkaline phosphatase activities in cells induced by the mature rhBMP-2 in combination with either dispase or collagenase were about 24% and 293% higher than that induced by the mature rhBMP-2 without addition of protease, respectively.

Example 8

Preparation and Sequencing of Modified BMP-4

Collagenase (Sigma Aldrich) was linked to sepharose beads and the un-bound collagenase was removed by extensive washing. Collagenase linked-sepharose beads were used to treat mature rhBMP-4 by incubation at 37° C. overnight with gentle mixing. The treated mature rhBMP-4 was separated by SDS-PAGE gel electrophoresis followed by protein transferring onto PVDF membrane. The proteins on PVDF membrane were stained by Coomassie blue and the related bands were cut for N-terminal sequencing using Edman degradation chemistry with an ABI Procise 494 sequencer. Proteins on PVDF membrane were also detected by Western Blot using antibody against C-terminus of rhBMP-4.

By comparing the collagenase treated mature rhBMP-4 bands with the untreated mature rhBMP-4 control bands, extra bands at around 17-22 kDa were cut for N-terminal sequencing. Ten amino acids of the N-terminus of the collagenase treated mature rhBMP-4 were detected using Edman degradation chemistry with an ABI Procise® 494 sequencer. The deduced amino acid sequence of the N-terminus of the treated rhBMP-4 was KKNKNCRRHS, which is the first 10 amino acids of SEQ ID NO:19 herein. The N-terminus of the treated rhBMP-4 matched the untreated mature rhBMP-4 sequence, indicating that the collagenase cleaved the mature BMP-4 after the first 10 amino acids. The Western blot detected a band for collagenase treated rhBMP-4 group, which is about 1-2 kDa smaller than the band for untreated mature rhBMP-4.

Example 9

Osteoinductive Potential of Modified rhBMP-4

Alkaline phosphatase is one of the distinctive biological or biologically-derived indicators of osteoinductivity. The AP assay measures the product para-nitrophenol (pNP) at a wavelength of 405 nm after 60 minutes of incubation of the substrate para-nitrophenyl phosphate (pNPP) with a cell lysate at 37° C. C2C12 cells (ATCC CRL-1772) were seeded at a density of about 25,000 cells/$cm^2$ in 24-well plates on day one. Collagenase and various concentrations of mature rhBMP4 were mixed in microcentrifuge tubes at molarity ratios between about 1:10 and about 1000:1 and incubated at 37° C. overnight. The collagenase-treated rhBMP-4 or untreated rhBMP4 was introduced into each well of the C2C12 cell seeded 24-well plate on day two. The final concentrations of rhBMP4 were 1, 5, 10, and 30 ng/mL. After 3 days of incubation at 37° C. and 5% $CO_2$, cells were collected from culture plates and cell lysates were prepared for AP assays and BCA total protein assays.

Figure 5:
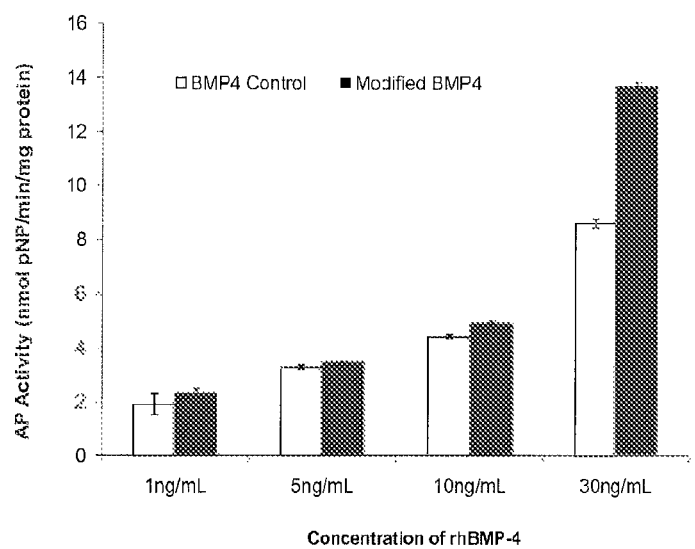
FIG. 5 depicts myoblast expression of alkaline phosphatase after being cultured with modified rhBMP-4. At a concentration of 30 ng/mL, cells treated with modified rhBMP4 expressed significantly higher AP activities than those treated with unmodified mature rhBMP-4.

The results of the in vitro AP assay are shown in FIG. 5. When cells were cultured with treated or untreated mature rhBMP-4 at a concentration of 10 ng/mL or less, the differences in alkaline phosphatase activity were negligible. At a concentration of 30 ng/mL, cells treated with collagenase-treated rhBMP-4 expressed significantly higher AP activities than those treated with untreated mature rhBMP-4.

Example 10

Osteoinductive Potential of Modified rhBMP-4 with or without a Protease

C2C12 cells (ATCC CRL-1772), which are from a mouse myoblast cell line, are seeded at a density of 25,000 cells/$cm^2$ in 24-well plates on day one. Collagenase and rhBMP-4 are mixed in microcentrifuge tubes at a molarity ratio of between about 1:10 and about 100:1 and are incubated overnight at 37° C. The treated mature rhBMP-4 is aliquoted with or without further HPLC purification described above. The aliquot with further HPLC purification (purified modified BMP-4) is quantified by ELISA. The aliquot without further HPLC purification (non-purified modified BMP-4) retained the collagenase in the aliquot. The aliquots are used to test the effect of treated mature rhBMP-4 on osteogenic potential of C2C12 myoblasts.

Each of the rhBMP-4 control, and the purified modified rhBMP-4, and the non-purified modified rhBMP-4 at the same concentration is introduced into wells of the C2C12 cell seeded 24-well plate. C2C12 cells cultured in media alone (without addition of rhBMP-4 or modified rhBMP-4) are used as a negative control.

After 3 days incubation at 37° C., 5% $CO_2$, the AP assay as described above is performed. The alkaline phosphatase activity of cells cultured with the purified modified rhBMP-4 or the non-purified modified rhBMP-4 are significantly higher than that of cells cultured with non-treated rhBMP-4 control. The alkaline phosphatase activity of cells cultured with non-purified modified rhBMP-4 is also significantly higher than that of cells cultured with purified modified rhBMP-4. The results demonstrate a significant increase in the alkaline phosphatase activity by administering the non-purified modified rhBMP-4 compared to administering the purified modified rhBMP-4.

Example 11

Preparation and Sequencing of Modified BMP-5

Modified recombinant human BMP-5 (rhBMP-5) was obtained by treating mature rhBMP-5 with dispase (Worthington), collagenase (Sigma-Aldrich), or cathepsin K. The mature rhBMP-5 had the sequence of amino acids 317-454 of SEQ ID NO:4 prior to modification. Aliquots of the modified mature rhBMP-5 and mature rhBMP-5 control were separated by SDS-PAGE gel electrophoresis and the peptides were transferred onto PVDF membrane. The proteins on PVDF membrane were stained by Coomassie blue or detected with Western blot using antibody against amino acids 407-450 of rhBMP-5.

The related bands from Coomassie blue stained PVDF membrane were cut and used for N-terminal sequencing. Ten amino acids of the N-terminus of the dispase-modified or collagenase-modified mature rhBMP-5 were detected using Edman degradation chemistry with an ABI Procise® 494 sequencer. The deduced amino acid sequence of the N-terminus of the modified rhBMP-5 was taken to be YNTSEQKQAC, which is the first 10 amino acids of SEQ ID NO:21 herein. Another deduced amino acid sequence of the N-terminus of the modified rhBMP-5 was taken to be SVGDYNTSEQ, which is the first 10 amino acids of SEQ ID NO:20 herein. Another deduced amino acid sequence of the N-terminus of the treated rhBMP-5 was taken to be TSEQKQACKK, which is the first 10 amino acids of SEQ ID NO:22 herein. Another deduced amino acid sequence of the N-terminus of the treated rhBMP-5 was taken to be DYNTSEQKQA, which is the first 10 amino acids of SEQ ID NO:23 herein. Another deduced amino acid sequence of the N-terminus of the treated rhBMP-5 was taken to be MSSVGDYNTS, which is the first 10 amino acids of SEQ ID NO:24 herein. Another deduced amino acid sequence of the N-terminus of the treated rhBMP-5 was taken to be VGDYNTSEQK, which is the first 10 amino acids of SEQ ID NO:25 herein. Another deduced amino acid sequence of the N-terminus of the treated rhBMP-5 was taken to be QA(C)KKHELYV, which is the first 10 amino acids of SEQ ID NO:26 herein. One more deduced amino acid sequence of the N-terminus of the treated rhBMP-5 was taken to be EQKQA(C)KKHE, which is the first 10 amino acids of SEQ ID NO:27 herein. One more deduced amino acid sequence of the N-terminus of the treated rhBMP-5 was taken to be SEQKQACKKH, which is the first 10 amino acids of SEQ ID NO:28 herein.

Example 12

Osteoinductive Potential of Modified rhBMP-5

C2C12 cells (ATCC CRL-1772) were seeded at a density of 25,000 cells/cm$^2$ in 24-well plates on day one. Dispase or collagenase and rhBMP-5 were mixed in microcentrifuge tubes at molarity ratios between about 1:100 and about 1000 :1 and incubated at 37° C. for 10-60 minutes or 18-20hours. The modified rhBMP5 or unmodified rhBMP5 was introduced into each well of the C2C12 cell seeded 24-well plate on day two. The final concentrations of rhBMP5 were 0.25 ug/mL, 0.5 ug/mL, and 1 ug/mL in each well of control and modified groups. After 3 days of incubation at 37° C. and 5% $CO_2$, cells were collected from culture plates and cell lysates were prepared for AP assays and BCA total protein assays. Alkaline phosphatase is one of the distinctive biological or biologically-derived indicators of osteoinductivity. The AP assay measures the product para-nitrophenol (pNP) at a wavelength of 405 nm after 60 minutes of incubation of the substrate para-nitrophenyl phosphate (pNPP) with a cell lysate at 37° C.

Figure 6:
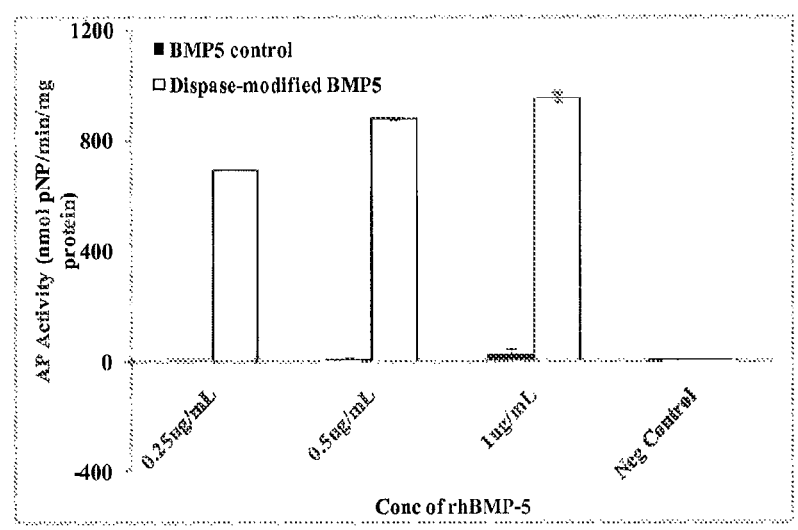
FIG. 6 depicts myoblast expression of alkaline phosphatase after being cultured with different concentrations of unmodified or dispase-modified rhBMP-5. Myoblasts treated with dispase modified rhBMP-5 showed significantly greater alkaline phosphatase activity over myoblasts treated with unmodified rhBMP-5.
Figure 7:
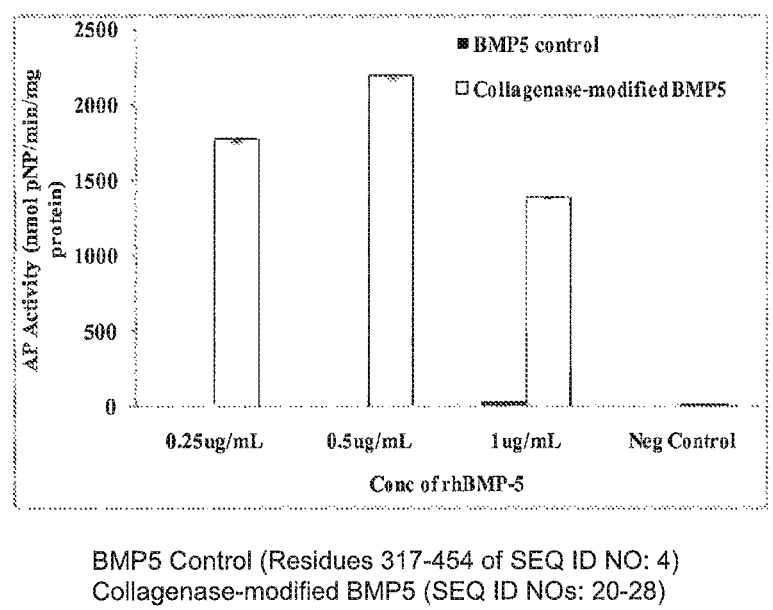
FIG. 7 depicts myoblast expression of alkaline phosphatase after being cultured with different concentrations of unmodified or collagenase-modified rhBMP-5. Myoblasts treated with collagenase modified rhBMP-5 showed significantly greater alkaline phosphatase activity over myoblasts treated with unmodified rhBMP-5.

The results of the in vitro AP assay are shown in FIGS. 6 and 7. When cells were cultured with dispase-modified or unmodified rhBMP5 at a concentration of 0.25 ug/mL, 0.5 ug/mL, or 1 ug/mL, the alkaline phosphatase activity induced by dispase-modified rhBMP5 was about 400 times, 120 times, or 35 times higher than that induced by unmodified rhBMP5, respectively (FIG. 6). When cells were cultured with collagenase-modified or unmodified rhBMP5, significant increases on alkaline phosphatase activity were found in all concentration groups (FIG. 7). At 0.25 ug/mL, 0.5 ug/mL, or 1 ug/mL in cell culture, the alkaline phosphatase activity induced by collagenase-modified rhBMP5 was about 1000 times, 300 times, or 50 times higher than that induced by unmodified rhBMP5, respectively.

Example 13

Osteoinductive Potential of Modified rhBMP-5 with or without a Protease

Dispase and rhBMP-5 were mixed in microcentrifuge tubes at a molarity ratio of between about 1:1000 and about 100:1 and incubated at 20 to37° C. for 10-60 minutes. The treated mature rhBMP-5 was further purified with reverse phase HPLC using a C-18 column. The collected fractions from HPLC were lyophilized, quantified and used to test the effect of modified rhBMP-5 on osteoinductive potential of C2C12 myoblasts.

C2C12 cells (ATCC CRL-1772) were seeded at a density of 25,000 cells/cm$^2$ in 24-well plates on day one. The purified modified rhBMP-5 alone, or the same concentration of purified modified rhBMP-5 with the addition of dispase or collagenase was introduced into wells of C2C12 cell. C2C12 cells cultured in media alone (without addition of modified rhBMP-5) were used as a negative control.

Figure 8:
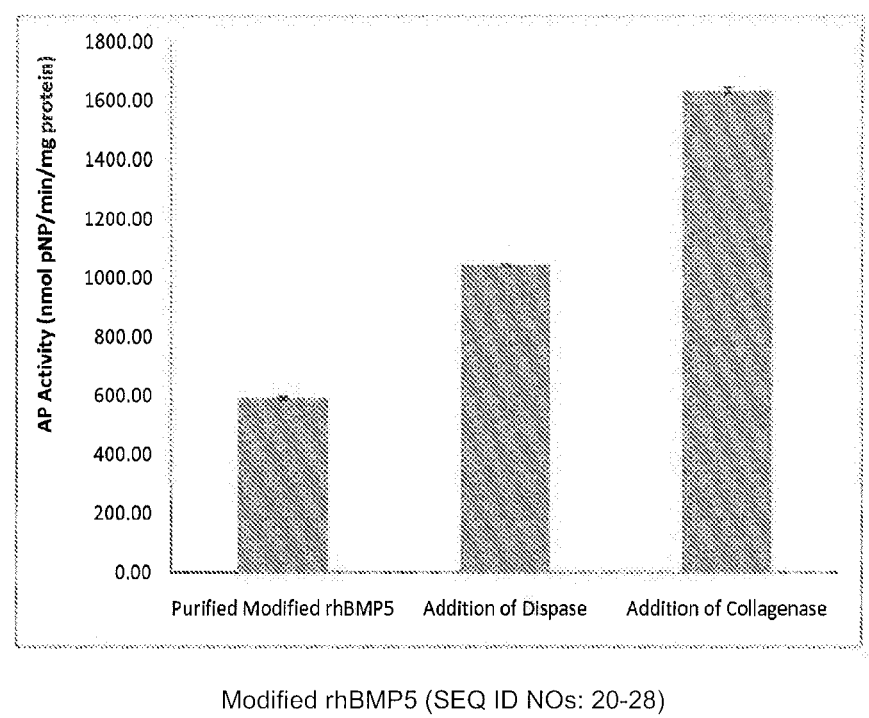
FIG. 8 depicts the expression of alkaline phosphatase in myoblast after being cultured with purified modified rhBMP-5 alone, or the same concentration of purified modified rhBMP-5 with the addition of dispase or collagenase.

After 3 days incubation at 37° C., 5% $CO_2$, an AP assay was performed as described above. As shown in FIG. 8, Alkaline phosphatase activity in the cells induced by the purified modified rhBMP-5 in combination with dispase was about 76% higher than that induced by the purified modified rhBMP-5 alone. Alkaline phosphatase activity in the cells induced by the purified modified rhBMP-5 in combination with collagenase was about 176% higher than that induced by the purified modified rhBMP-5 alone.

Example 14

Chondrogenic Potential of Modified rhBMP-5

The ATDC5 murine chondrosarcoma cell line (Riken Cell Bank) that have been widely used to study chondrocyte differentiation were seeded at 2,000 cells/cm$^2$ in 6-well plates. After 5 days of culture, the culture media was changed to the differentiation media that contains 5% fetal bovine serum, 10 ug/mL bovine insulin, and 50 ug/mL ascorbic acid (differentiation media control), or the differentiation media with the addition of rhBMP-5 or dispase-modified rhBMP-5 prepared as shown above. The cells were cultured in the differentiation media for a total of 13 days and the media was changed every 3 days. Cells were collected at different time points and total RNA was extracted and followed by reverse transcription using Applied Biosystems RNA-to-cDNA kit. The chondrogenic-specific genes, collagen type 2a (COL2a1), aggrecan (ACAN), cartilage oligomeric matrix protein (COMP) and transcription factor SOX9, were quantified using TaqMan Gene Expression Assay kit from Applied. Biosystems, Inc. The relative expression (ΔCt) of the target gene was normalized to GAPDH endogenous gene expression and the fold change ($2^{-\Delta\Delta Ct}$) was calculated relative to the differentiation media control. As shown in tables 7-10 below, the COL2a1, ACAN, COMP, SOX9 gene expressions in cells cultured with dispase-modified rhBMP-5 were all higher than that in cells cultured with rhBMP-5 control.

TABLE 7

| | Expression of COL2a1 | | |
|---|---|---|---|
| Incubation Time (days) | rhBMP-5 Control Fold change relative to differenetiated media control | Modified rhBMP-5 Fold change relative to differenetiated media control | % of increase |
| 3 | 1.30 ± 0.21 | 2.08 ± 0.19 | 60.58 |
| 5 | 1.23 ± 0.09 | 1.07 ± 0.08 | −12.94 |
| 7 | 0.70 ± 0.06 | 1.85 ± 0.57 | 163.29 |
| 9 | 0.84 ± 0.05 | 1.17 ± 0.10 | 39.80 |
| 11 | 1.52 ± 0.19 | 3.40 ± 0.43 | 123.97 |
| 13 | 1.38 ± 0.05 | 3.38 ± 0.19 | 145.09 |

TABLE 8

Expression of ACAN

| Incubation Time (days) | rhBMP-5 Control Fold change relative to differenetiated media control | Modified rhBMP-5 Fold change relative to differenetiated media control | % of increase |
|---|---|---|---|
| 3 | 0.85 ± 0.08 | 1.94 ± 0.10 | 127.10 |
| 5 | 0.78 ± 0.05 | 2.71 ± 0.22 | 249.03 |
| 7 | 0.83 ± 0.04 | 3.46 ± 1.06 | 316.02 |
| 9 | 0.35 ± 0.01 | 3.90 ± 0.16 | 1000.43 |
| 11 | 1.97 ± 0.22 | 4.50 ± 0.56 | 128.15 |
| 13 | 4.16 ± 0.18 | 13.15 ± 0.82 | 216.02 |

TABLE 9

Expression of COMP

| Incubation Time (days) | rhBMP-5 Control Fold change relative to differenetiated media control | Modified rhBMP-5 Fold change relative to differenetiated media control | % of increase |
|---|---|---|---|
| 3 | 0.55 ± 0.06 | 1.27 ± 0.06 | 130.80 |
| 5 | 0.36 ± 0.03 | 0.23 ± 0.03 | −37.58 |
| 7 | 0.37 ± 0.03 | 0.92 ± 0.28 | 146.80 |
| 9 | 0.16 ± 0.08 | 0.89 ± 0.18 | 459.19 |
| 11 | 0.47 ± 0.06 | 1.46 ± 0.17 | 210.23 |
| 13 | 0.91 ± 0.06 | 1.77 ± 0.17 | 94.08 |

TABLE 10

Expression of SOX9

| Incubation Time (days) | rhBMP-5 Control Fold change relative to differenetiated media control | Modified rhBMP-5 Fold change relative to differenetiated media control | % of increase |
|---|---|---|---|
| 3 | 0.60 ± 0.05 | 0.67 ± 0.07 | 10.70 |
| 5 | 0.59 ± 0.18 | 0.89 ± 0.06 | 50.18 |
| 7 | 0.80 ± 0.05 | 0.71 ± 0.21 | −11.32 |
| 9 | 0.61 ± 0.04 | 0.83 ± 0.07 | 35.97 |
| 11 | 1.08 ± 0.13 | 1.18 ± 0.16 | 8.92 |
| 13 | 1.44 ± 0.26 | 2.84 ± 0.16 | 97.25 |

Example 15

Osteoinductive Potential of Mature rhBMP-5 with the Addition of Protease

C2C12 cells (ATCC CRL-1772) were cultured as described above. The mature rhBMP-5 control (200 ng/mL, R&D Systems, Inc.), or the same concentration of mature rhBMP-5 with the addition of collagenase or dispase (molarity ratio between about 1:100 and about 100:1) was introduced into wells of the C2C12 cells. C2C12 cells cultured in media alone (without addition of rhBMP-5) were used as a negative control.

After 3 days incubation at 37° C., 5% $CO_2$, an AP assay was performed as described above. The results showed that the alkaline phosphatase activities in cells induced by the mature rhBMP-5 in combination with either collagenase or dispase were 21 and 42 times higher than that induced by the mature rhBMP-5 without addition of protease, respectively.

Example 16

Preparation and Sequencing of Collagenase-Modified BMP-7

The mature rhBMP-7 was treated with collagenase in a microcentrifuge tube at a molarity ratio of between about 1:10 and about 100:1 and incubated overnight at 37° C. The treated mature rhBMP-7 was further purified by reverse phase HPLC using a C-18 column. The collected fractions from HPLC were tested for osteoinductive potential using an in vitro alkaline phosphatase assay. The fractions that showed significantly high alkaline phosphatase activities were further separated by SDS-PAGE gel electrophoresis and blotted onto PVDF membrane. Proteins on the PVDF membrane were stained by coomassie blue and the related bands were cut and sent for N-terminal sequencing.

In the Coomassie blue stained PVDF membrane, the fraction 43 sample from the collagenase-treated rhBMP-7 showed clean bands at around 15-16 kDa.

Ten amino acids of the N-terminus of the collagenase treated mature rhBMP-7 were detected using Edman degradation chemistry with an ABI Procise® 494 sequencer. The deduced amino acid sequence of the N-terminus of the treated rhBMP-7 was taken to be ENSSSDQRQA, which is the first 10 amino acids of SEQ ID NO:31 herein. This deduced N-terminus of the treated rhBMP-7 matches the untreated mature rhBMP-7 sequence except, indicating that the collagenase cleaved the mature BMP-7 after the first 27 amino acids. Western blot detected untreated and collagenase-treated mature rhBMP-7, and the treated rhBMP-7 was about 2-3 kDa smaller than the untreated rhBMP-7.

Example 17

Osteoinductive Potential of Collagenase-Modified BMP-7

Figure 9:
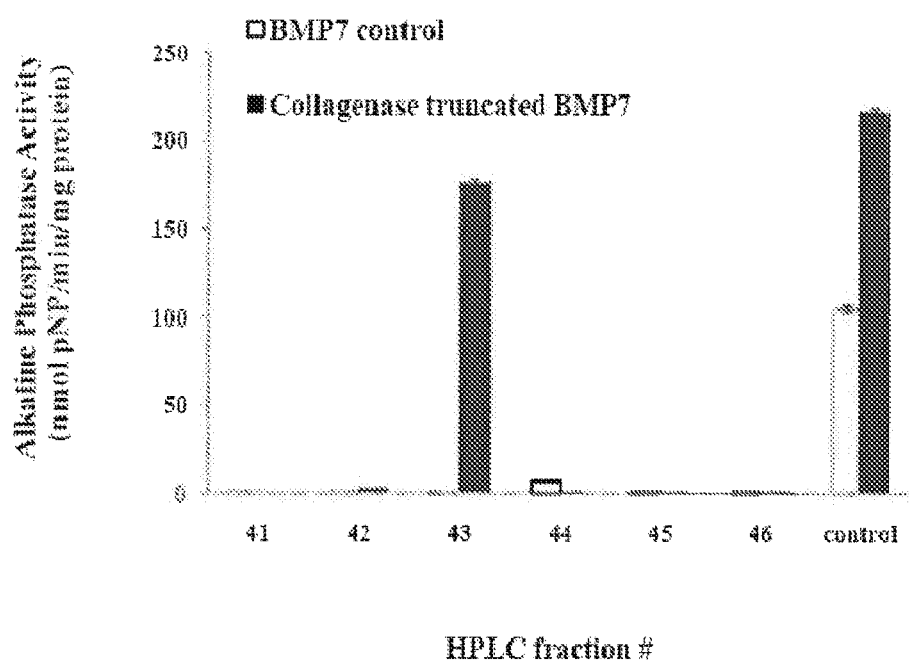
FIG. 9 depicts myoblast expression of alkaline phosphatase after being cultured with modified rhBMP-7. Myoblasts treated with modified rhBMP-7 showed significantly greater alkaline phosphatase activity over myoblasts treated with unmodified rhBMP-7. When fractionated via HPLC, fractions 43 induced the highest levels of alkaline phosphatase in myoblasts.

Alkaline phosphatase is one of the distinctive biological or biologically-derived indicators of osteoinductivity. The AP assay measures the product para-nitrophenol (pNP) at a wavelength of 405 nm after 60 minutes of incubation of the substrate para-nitrophenyl phosphate (pNPP) with a cell lysate at 37° C. The alkaline phosphatase activities induced by the HPLC fractions from Example 16 are shown in FIG. 9. The alkaline phosphatase activity induced by the fraction 43 from the collagen-treated rhBMP-7 was significantly higher than the alkaline phosphatase activity induced by other HPLC fractions.

Example 18

Dose Responsiveness of Modified rhBMP-7

C2C12 cells (ATCC CRL-1772) were seeded at a density of 25,000 cells/cm² in 24-well plates on day one. Collagenase and various concentrations of rhBMP7 were mixed in microcentrifuge tubes at molarity ratios between about 1:10 and about 1000:1 and incubated at 37° C. overnight. The collagenase-treated rhBMP7 or untreated rhBMP7 was introduced into each well of the C2C12 cell seeded 24-well plate on day two. The final concentrations of rhBMP7 were 5 ng/mL, 10 ng/mL, 25 ng/mL, 50 ng/mL, 100 ng/mL, and 200 ng/mL in each well. After 3 days of incubation at 37° C. and 5% $CO_2$, cells were collected from culture plates and cell lysates were prepared for AP assays and BCA total protein assays.

Figure 10:
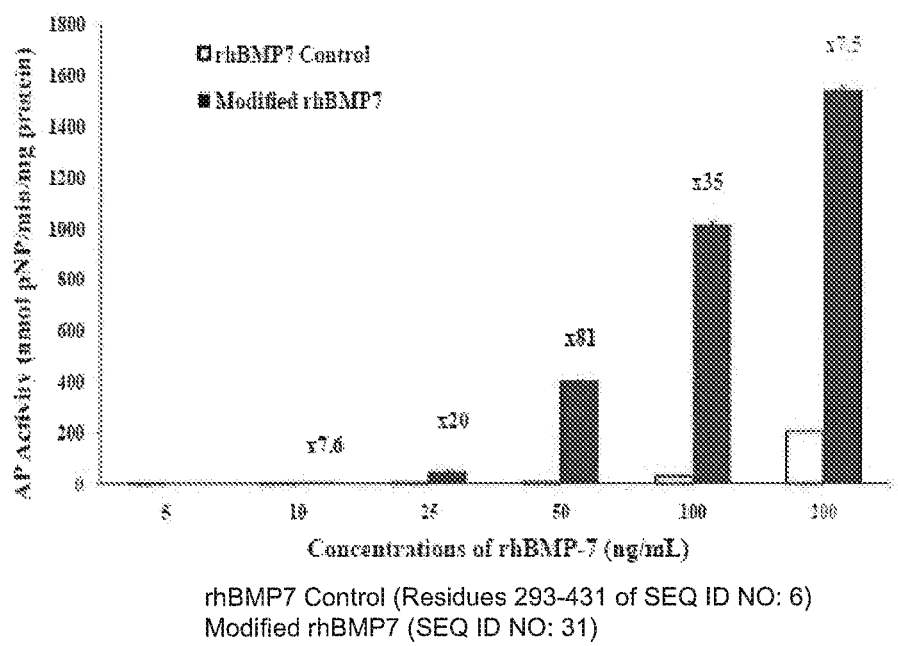
FIG. 10 depicts expression of alkaline phosphatase in myoblasts after being cultured with various concentrations of modified rhBMP-7.

The results of the in vitro AP assay are shown in FIG. 10. When cells were cultured with treated or untreated rhBMP7 at a concentration of 10 ng/mL or less, the differences in alkaline phosphatase activity were negligible. At concentrations of 25 rig/mL or higher, significant differences were found between collagenase-treated rhBMP7 groups and untreated rhBMP7 groups. At 50 ng/mL in cell culture, the alkaline phosphatase activity induced by collagenase-treated rhBMP7 was about 80 times higher than that induced by untreated rhBMP7.

Example 19

Preparation and Sequencing of Trypsin-Modified BMP-7 rhBMP-7 was incubated with trypsin overnight at 37° C. Trypsin and rhBMP-7 were used at a molarity ratio between about 1:50 and about 100:1. The treated mature rhBMP-7 was separated by SDS-PAGE gel electrophoresis followed by protein transferring onto PVDF membrane. The proteins on PVDF membrane were stained by Coomassie blue and the related bands were cut for N-terminal sequencing using Edman degradation chemistry with an ABI Procise 494 sequencer. Proteins on PVDF membrane were also detected by Western Blot using antibody against C-terminus of rhBMP-7.

By comparing the trypsin treated mature rhBMP-7 bands with the untreated mature rhBMP-7 control bands, extra band at around 14-16 kDa were cut for N-terminal sequencing. Ten amino acids of the N-terminus of the trypsin treated mature rhBMP-7 were detected using Edman degradation chemistry with an ABI Procise® 494 sequencer. The deduced amino acid sequence of the N-terminus of the treated rhBMP-7 was QACKKHELYV, which is the first 10 amino acids of SEQ ID NO:30 herein. The N-terminus of the trypsin-treated rhBMP-7 matches the untreated mature rhBMP-7 sequence, indicating that the trypsin cleaved the mature BMP-7 after the first 35 amino acids. The Western blot detected a band for trypsin treated rhBMP-7 group, which is about 2-3 kDa smaller than the band for untreated mature rhBMP-7.

Example 20

Osteoinductive Potential of Trypsin-Modified BMP-7

C2C12 cells were cultured as described above. Trypsin and rhBMP7 were mixed in a microcentrifuge tube at molarity ratios between about 1:50 and about 100 :1 and incubated at 37° C. overnight. The trypsin-modified rhBMP7 or unmodified rhBMP7 was introduced into each well of the C2C12 cell seeded 24-well plate on day two. After 3 days of incubation at 37° C. and 5% $CO_2$, cells were collected from culture plates and cell lysates were prepared for AP assays and BCA total protein assays.

Figure 11:
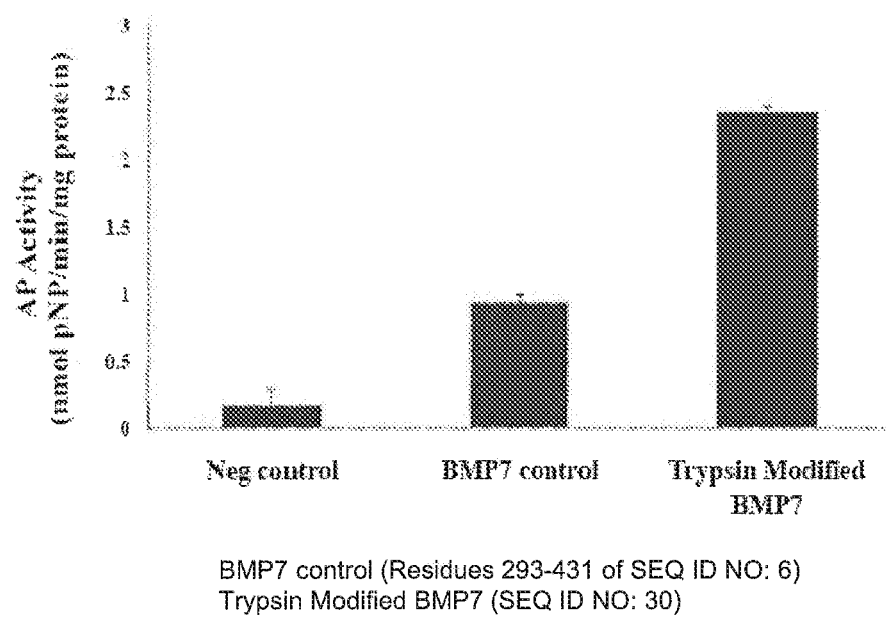
FIG. 11 depicts expression of alkaline phosphatase in myoblasts after being cultured with unmodified rhBMP-7 or trypsin-modified rhBMP-7.

The results of the in vitro AP assay are shown in FIG. 11. The alkaline phosphatase activity induced by trypsin-modified rhBMP7 was about 1.5 times higher than that induced by unmodified rhBMP7.

Example 21

Osteoinductive Potential of Modified rhBMP-7 with or without a Protease

C2C12 cells were cultured as described above. Collagenase and rhBMP-7 are mixed in microcentrifuge tubes at a molarity ratio of between about 1:10 and about 100:1 and are incubated overnight at 37° C. The treated mature rhBMP-7 is aliquoted with or without further HPLC purification described above. The aliquot with further HPLC purification (purified modified BMP-7) is quantified by ELISA. The aliquot without further HPLC purification (non-purified modified BMP-7) retained the collagenase hi the aliquot. The aliquots are used to test the effect of treated mature rhBMP-7 on osteogenic potential of C2C12 myoblasts.

Each of the rhBMP-7 control, and the purified modified rhBMP-7, and the non-purified modified rhBMP-7 at the same concentration is introduced into wells of the C2C12 cell seeded 24-well plate. C2C12 cells cultured in media alone (without addition of rhBMP-7 or modified rhBMP-7) are used as a negative control.

After 3 days incubation at 37° C., 5% $CO_2$, the AP assay as described above is performed. The alkaline phosphatase activity of cells cultured with the purified modified rhBMP-7 or the non-purified modified rhBMP-7 are significantly higher than that of cells cultured with non-treated rhBMP-7 control. The alkaline phosphatase activity of cells cultured with non-purified modified rhBMP-7 is also significantly higher than that of cells cultured with purified modified rhBMP-7. The results demonstrate a significant increase in the alkaline phosphatase activity by administering the non-purified modified rhBMP-7 compared to administering the purified modified rhBMP-7.

Example 22

Osteoinductive Potential of Modified rhBMP-7 with or without an Additional Protease Dispase and rhBMP-7 were mixed in microcentrifuge tubes at a molarity ratio between about 1:100 and about 1000:1 and incubated at 37° C. from about 15 minutes to about 24 hours.

C2C12 cells were cultured as described above. The non-treated rhBMP-7 control, dispase modified rhBMP-7 without further purification, or dispase modified rhBMP-7 with the addition of 100ug/mL collagenase in culture media were introduced into wells of the C2C12 cell seeded 24-well plate on day two. C2C12 cells cultured in media alone (without addition of rhBMP-7 or treated rhBMP-7) were used as a negative control. After 3 days of incubation at 37° C/5% $CO_2$, cells were collected from culture plates and cell lysates were prepared fur AP assays and BCA total protein assays as described above.

Figure 12:
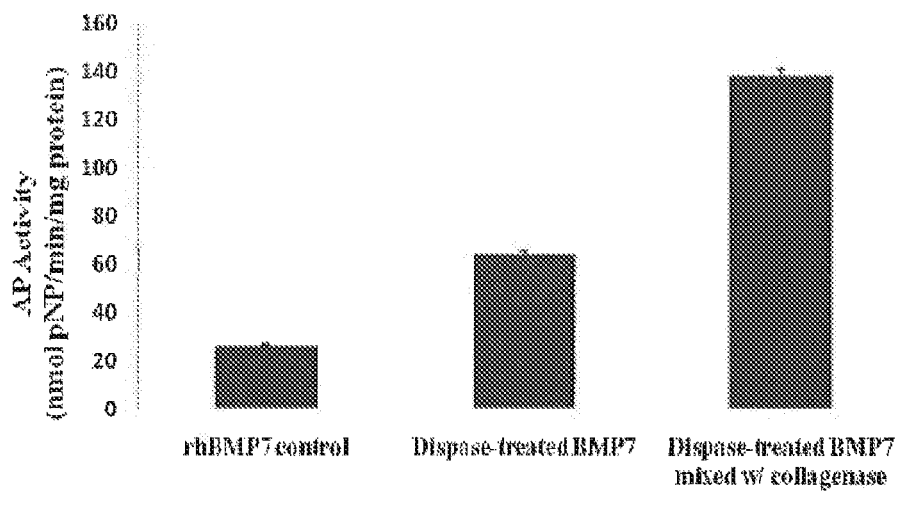
FIG. 12 depicts in vitro alkaline phosphatase expressions by myoblast cells cultured with non-treated rhBMP-7 control, dispase modified rhBMP-7, or dispase modified rhBMP-7 with the addition of collagenase in culture media.

The results of the in vitro AP assay are shown in FIG. 12. The alkaline phosphatase activity of cells cultured with dispase modified rhBMP-7 was about 141% higher than that of cells cultured with non-treated rhBMP-7 control, while the alkaline phosphatase activity of cells cultured with dispase modified rhBMP-7 with the addition of collagenase in media further increased 116% compared to the dispase modified rhBMP-7 group. The alkaline phosphatase activity of cells cultured with dispase modified rhBMP-7 with the addition of collagenase in media was about 421% higher than that of cells cultured with non-treated rhBMP-7 control.

Example 23

Osteoinductive Potential of Modified rhBMP-7 with a Protease

C2C12 cells (ATCC CRL-1772) are cultured as described above. Collagenase and rhBMP-7 are mixed in microcentrifitge tubes at a molarity ratio of between about 1:10 and about 100:1 and incubated overnight at 37° C. with agitation. The treated mature rhBMP-7 is aliquoted, and the aliquots are used to test the effect of treated mature rhBMP-7 on osteogenic potential of C2C12 myoblasts as follows.

For the osteoinductive potential assessment, base media of DMEM containing 1% FBS, 50 μg/mL of ascorbic acid and 10 mM of β-glycerolphosphate is used as a control group. The base media control with the addition of 50 ng/mL of rhBMP-7 is used as the BMP-7 positive control group. The base media control with the addition of 50 ng/mL of modified rhBMP-7 without the purification is used as the test group. The media are added into C2C12 cells seeded on chamber slides and changed every 3-4 days.

After several days of incubation at 37° C., 5% $CO_2$, photographs are also taken for cell cultures in each group. The nodule formation of C2C12 cells appear only in modified rhBMP-7 group, but not in the other two control groups. After more days of incubation, the media is removed from chamber slides and the slides are stained with Alizarin Red S. Alizarin red S is used to identify calcium-rich deposits by cells in culture or tissue sections, which indicates the effect of osteoinductive material on osteogenic potential of cells.

For the base media control group, no positive Alizarin red S staining is found at any tested time points. For the rhBMP-7 control group, some Alizarin red S staining is detected after 6 or 12 days of incubation. For the modified rhBMP-7 group, after 6 days of incubation, significant amount of nodules stain positive by Alizarin red S. After 12 days of incubation, more Alizarin red S positively stain nodules of larger size are observed in C2C12 cells cultured with modified rhBMP-7 than that in C2C12 cells cultured with unmodified rhBMP-7. This data suggests that modified rhBMP-7 has a significantly greater effect on osteogenic potential of C2C12 myoblasts as compared to the unmodified mature rhBMP-7 control.

Example 24

Preparation and Sequencing of Modified BMP-13

Modified recombinant human BMP-13 (rhBMP-13 or rhGDF-6) was obtained by treating mature rhBMP-13 with dispase (Worthington) or collagenase (Sigma-Aldrich). The mature rhBMP-13 had the sequence of amino acids 336-455 of SEQ ID NO:12 prior to modification. Aliquots of the modified mature rhBMP-13 and unmodified mature rhBMP-13 control were separated by SDS-PAGE gel electrophoresis and the peptides were transferred onto PVDF membrane. The proteins on PVDF membrane were stained by Coomassie blue or detected with Western blot using antibody against C-terminal region of mature rhBMP-13.

The related bands from Coomassie blue stained PVDF membrane were cut and used for N-terminal sequencing. Ten amino acids of the N-tenninus of the dispase modified mature rhBMP-13 were detected using Edman degradation chemistry with an ABI Procise® 494 sequencer. The deduced amino acid sequence of the N-terminus of the modified mature rhBMP-13 was taken to be GKKSRL-RCSK, which is the first 10 amino acids of SEQ ID NO:34 herein.

Example 25

Improvement of Osteoinductive Potential of Modified BMP-13

C2C12 cells (ATCC CRL-1772) were seeded at a density of 25,000 cells/cm² in 24-well plates on day one. Dispase and mature rhBMP-13 (rhGDF-6) were mixed in microcentrifuge tubes at molarity ratios between about 1:100 and about 1000 :1 and incubated at 37° C. for 5-60 minutes. The dispase-modified mature rhGDF-6 or unmodified mature rhGDF-6 control was introduced into each well of the C2C12 cell seeded 24-well plate on day two. The final concentrations of rhBMP-13 were 1 ug/mL, 2 ug/mL, and 3.67 ug/mL for both control and modified groups. After 3 days of incubation at 37° C. and 5% $CO_2$, cells were collected from culture plates and cell lysates were prepared for Alkaline phosphatase (AP) assays and BCA total protein assays. Alkaline phosphatase is one of the distinctive biological or biologically-derived indicators of osteoinductivity. The AP assay measures the product para-nitrophenol (pNP) at a wavelength of 405 nm after 60 minutes of incubation of the substrate para-nitrophenyl phosphate (pNPP) with a cell lysate at 37° C.

Figure 13:
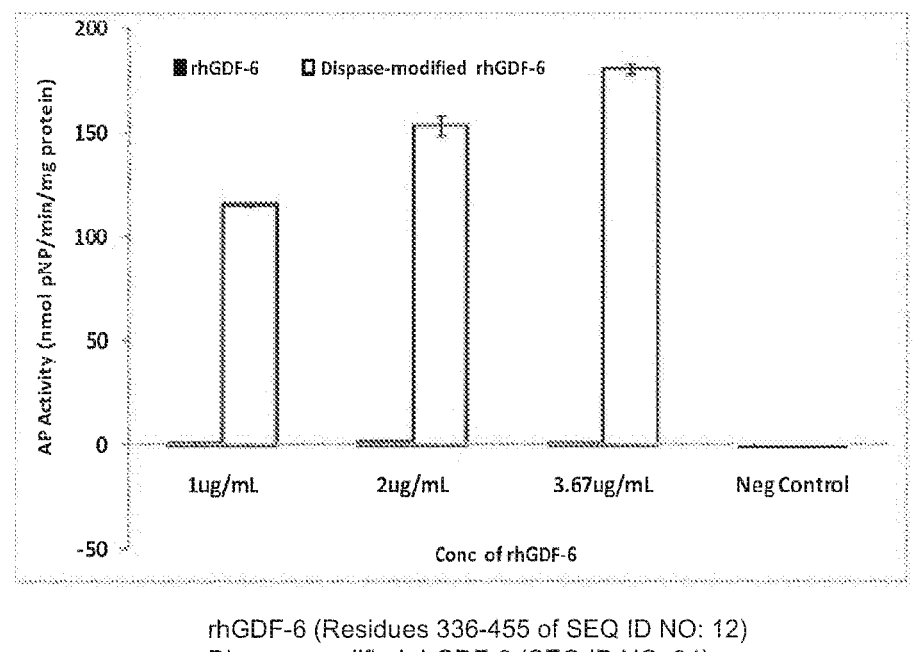
FIG. 13 depicts the expression of alkaline phosphatase in C2C12 cells after being cultured with various concentrations of unmodified or dispase modified rhBMP-13 (rhGDF-6). The alkaline phosphatase activity induced by dispase-modified mature rhBMP-13 was about 300 -350 times higher than that induced by unmodified mature rhBMP-13control.

The results of the in vitro AP assay are shown in FIG. 13. When cells were cultured with dispase-modified or unmodified rhBMP-13 at a concentration of 1 ug/mL or higher, significant enhancements of AP activity were found in cells treated with dispase-modified mature rhBMP-13 compared to the cells treated with unmodified mature rhBMP-13 (Fig.13). The alkaline phosphatase activity induced by dispase-modified mature rhBMP-13 was about 300 -350 times higher than that induced by unmodified mature rhBMP-13 control.

Example 26

Improvement of Osteoinductive Potential of Modified BMP-13

C2C12 cells (ATCC CRL-1772) were seeded at a density of 25,000 cells/cm² in 24-well plates on day one. Collagenase (Sigma) and mature rhBMP-13 were mixed in microcentrifuge tubes at molarity ratios between about 1:100 and about 1000 :1 and incubated at 37° C. for 0.5-24 hours. The collagenase-modified mature rhBMP-13 or unmodified mature rhBMP-13 control was introduced into each well of the C2C12 cell seeded 24-well plate on day two. The final concentrations of rhBMP-13 were 0.5 ug/mL, 1 ug/mL, and 2 ug/mL for both control and modified groups. After 3 days of incubation at 37° C. and 5% $CO_2$, cells were collected from culture plates and cell lysates were prepared for AP assays and BCA total protein assays.

Figure 14:
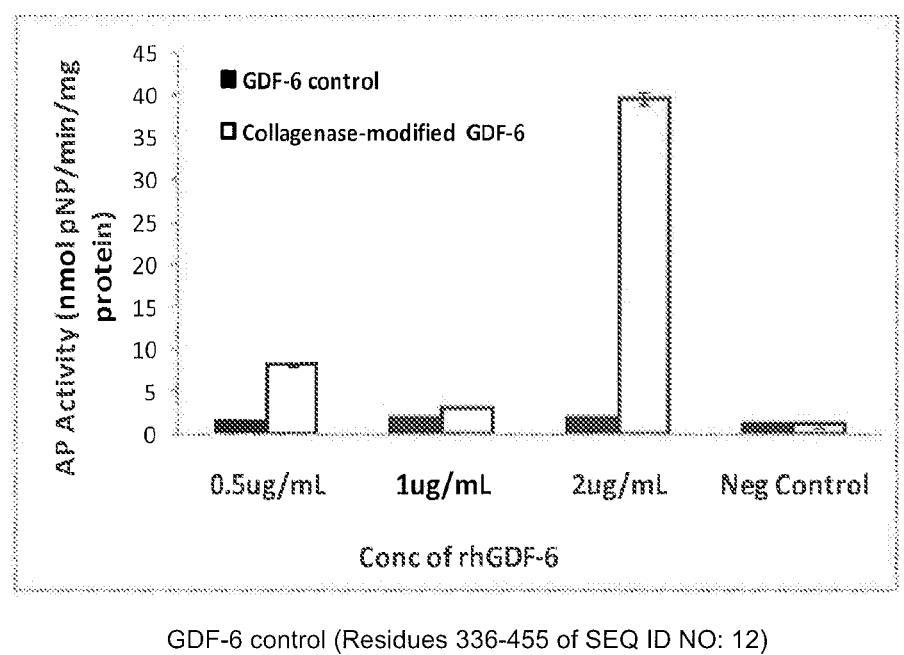
FIG. 14 depicts the expression of alkaline phosphatase in C2C12 cells after being cultured with various concentrations of unmodified or collagenase modified mature rhBMP-13 (rhGDF-6). The alkaline phosphatase activity induced by collagenase-modified mature rhBMP-13 was about 0.7 -20 times higher than that induced by unmodified mature rhBMP-13 control.

The results of the in vitro AP assay are shown in FIG. 14. When cells were cultured with collagenase-modified or unmodified rhBMP-13 at a concentration of 0.5 ug/mL or higher, significant enhancements of AP activity were found in cells treated with collagenase-modified mature rhBMP-13 compared to the cells treated with unmodified mature rhGDF-6 (FIG. 14). The alkaline phosphatase activity induced by collagenase-modified mature rhBMP-13 was about 0.7 -20 times higher than that induced by unmodified mature rhBMP-13 control.

Example 27

Osteoinductive Potential of Purified Modified rhBMP-13 with or without a Protease Dispase and rhBMP-13 (PeproTech, Inc.) were mixed in microcentrifuge tubes at a molarity ratio of between about 1:100 and about 100:1 and incubated at 35-40° C. for 10-60 minutes. The mixture was purified with reverse phase HPLC using a C-18 column. The HPLC purified modified rhBMP- 13 was used to test the effect of modified rhBMP-13 on osteogenic potential of C2C12 myoblasts.

C2C12 cells (ATCC CRL-1772) were seeded at a density of 25,000 cells/cm$^2$ in 24-well plates on day one. The purified modified rhBMP-13, or the same concentration of purified modified rhBMP-13 with the addition of dispase or collagenase (molarity ratio between about 1:100 and about 100:1), were introduced into wells of the C2C12 cells on day two. C2C12 cells cultured in media alone (without addition of modified rhBMP-13) were used as a negative control.

After 3 days of incubation at 37° C., 5% $CO_2$, the AP assay was performed as described above. The alkaline phosphatase activity in the cells induced by the purified modified rhBMP-13 in combination with either dispase or collagenase was about of 25 times and 50% higher than that induced by purified modified rhBMP-13 alone, respectively.

Example 28

Osteoinductive Potential of Modified rhBMP-13 with or without an Additional Protease C2C12 cells were cultured as described above. Non-purified modified rhBMP-13(1 ug/mL), or an equal concentration of non-purified modified rhBMP-13 with the addition of either dispase or collagenase was introduced into wells of the C2C12 cells. The AP assay was performed as described above. The alkaline phosphatase activity in the cells induced by the non-purified modified rhBMP-13 in combination with either dispase or collagenase were about 18% and 81% higher than that induced by the non-purified modified rhBMP-13 alone, respectively.

Example 29

Osteoinductive Potential of Mature rhBMP-13 with the Addition of Protease

C2C12 cells (ATCC CRL-1772) were seeded at a density of 25,000 cells/cm$^2$ in 24-well plates on day one. The mature rhBMP-13 (1 μg/mL) or the same concentration of mature rhBMP-13 with the addition of dispase or collagenase (molarity ratio between about 1:100 and about 100:1) was introduced into wells of the C2C12 cells. C2C12 cells cultured in media alone (without addition of rhBMP-13) were used as a negative control.

After 3 days incubation at 37° C., 5% $CO_2$, an AP assay was performed as described above. The results showed that the alkaline phosphatase activities in cells induced by the mature rhBMP-13 in combination with either dispase or collagenase were about 50-180 times and 235% higher than that induced by the mature rhBMP-13 without addition of protease, respectively.

Example 30

Effect of Modified rhBMP-13 on Tendon-specific Gene Expression of Human Adipose-derived Stem Cells Human adipose-derived stem cells (hASC) were isolated from fat tissue of a human donor with research consent. Cells were propagated until the 5$^{th}$ passage and seeded at 5,000 cells/cm$^2$ in 6-well plates. After one day, the culture media was changed to the differentiation media that contains rhBMP-13 control (100 ng/mL) or dispase-modified rhBMP-13 (100 ng/mL) prepared as shown above. The cells were cultured in differentiation media for a total of 12 days and the media was changed every 3 days. Cells were collected at different time points and total RNA was extracted and followed by reverse transcription using Applied Biosystems RNA-to-cDNA kit. The target tendon-specific genes, scleraxis (SCX) and tenomodulin (TMND), were amplified and quantified using TaqMan Gene Expression Assay kit from Applied Biosystems, Inc. The relative expression (ΔCt) of the target gene was normalized to GAPDH endogenous gene expression and the fold change ($2^{-\Delta\Delta Ct}$) was calculated relative to the hASC control.

As shown in table IV below, the SCX gene expression in cells cultured with dispase-modified rhBMP-13 was about 18% to 40% higher than that in cells cultured with rhBMP-13 control for the first 6 days of culture. On day 9 and day 12, the SCX expression in cells cultured with dispase-modified rhBMP-13 was about 63% and 97% higher than that in cells cultured with rhBMP-13 control. The TMND gene expression in cells cultured with dispase-modified rhBMP-13 was about 84% higher than that in cells cultured with the rhBMP-13 control on day 6.

TABLE 11

| | Expression of Scleraxis (SCX) | | |
| --- | --- | --- | --- |
| Incubation Time (days) | rhBMP-13 Control Fold change relative to differenetiated media control | Modified rhBMP-13 Fold change relative to differenetiated media control | % of increase |
| 1 | 1.34 ± 0.42 | 1.62 ± 0.71 | 20.86 |
| 2 | 1.16 ± 0.16 | 1.67 ± 0.38 | 44.73 |
| 3 | 2.05 ± 0.67 | 2.49 ± 0.93 | 21.42 |
| 6 | 1.16 ± 0.27 | 1.37 ± 0.13 | 18.1 |
| 9 | 0.98 ± 0.15 | 1.60 ± 0.19 | 63.58 |
| 12 | 1.52 ± 0.24 | 2.99 ± 0.41 | 97.25 |

Example 31

Preparation and Sequencing of Modified BMP-14

Modified recombinant human BMP-14 (rhGDF-5 or rhBMP-14) was obtained by treating mature rhBMP-14 with dispase (Worthington) or collagenase (Sigma-Aldrich). The rhBMP-14 had the sequence of amino acids 382-501 of SEQ ID NO:13 prior to modification. Aliquots of the modified mature rhBMP-14 and unmodified mature rhBMP-14 control were separated by SDS-PAGE gel electrophoresis and the peptides were transferred onto PVDF membrane. The proteins on PVDF membrane were stained by Coomassie blue or detected with Western blot using antibody against internal region of mature rhBMP-14.

The related bands from Coomassie blue stained PVDF membrane were cut and used for N-terminal sequencing. Ten amino acids of the N-terminus of the dispase modified mature rhBMP-14 were detected using Edman degradation chemistry with an ABI Procise® 494 sequencer. The deduced amino acid sequence of the N-terminus of the modified rhBMP-14 was taken to be LKARCSRKAL, which is the first 10 amino acids of SEQ ID NO:35 herein.

Example 32

Dose-dependent Change of Osteoinductive Potential of Modified BMP-14

C2C12 cells (ATCC CRL-1772) were seeded at a density of 25,000 cells/cm$^2$ in 24-well plates on day one. Dispase and rhBMP-14 were mixed in microcentrifuge tubes at molarity ratios between about 1:100 and about 1000:1 and incubated at 37° C. for 5-60 minutes. The dispase-modified rhBMP-14 or unmodified rhBMP-14 control was introduced into each well of the C2C12 cell seeded 24-well plate on day two. The final concentrations of rhBMP-14 were 0.2 ug/mL, 0.5 ug/mL, and 1 ug/mL in each well for both control and modified groups. After 3 days of incubation at 37° C. and 5% $CO_2$, cells were collected from culture plates and cell lysates were prepared for AP assays and BCA total protein assays. Alkaline phosphatase is one of the distinctive biological or biologically-derived indicators of osteoinductivity. The AP assay measures the product para-nitrophcnol (pNP) at a wavelength of 405 nm after 60 minutes of incubation of the substrate para-nitrophenyl phosphate (pNPP) with a cell lysate at 37° C.

Figure 15:
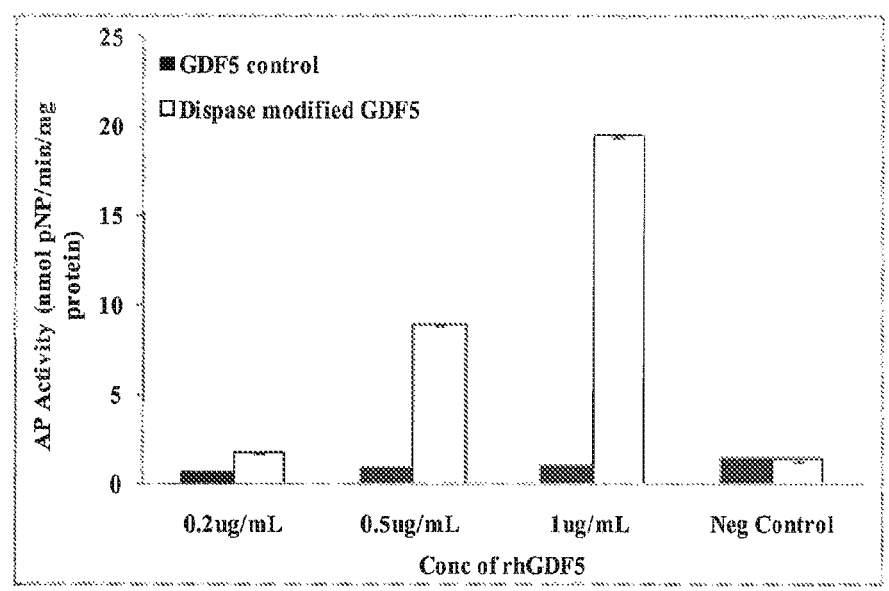
FIG. 15 depicts myoblast expression of alkaline phosphatase after being cultured with various concentrations of unmodified or modified rhBMP-14 (rhGDF-5). Myoblasts treated with dispase modified rhBMP-14 showed significantly greater alkaline phosphatase activity over myoblasts treated with unmodified rhBMP-14 control. The level of alkaline phosphatase activity increase was dose-dependent upon rhBMP-14 concentation.

The results of the in vitro AP assay are shown in FIG. 15. When cells were cultured with dispase-modified or unmodified rhBMP-14 at a concentration of 0.2 ug/mL or higher, significant enhancements were found in dispase-modified rhBMP-14 groups compared to the unmodified rhBMP-14 control groups (FIG. 15). At 0.2 ug/mL, 0.5 ug/mL, or 1 ug/mL in cell culture, the alkaline phosphatase activity induced by dispase-modified rhBMP-14 was about 1.5 times, 9 times, or 19 times higher than that induced by unmodified rhBMP-14 control, respectively.

Example 33

Osteoinductive Potential of Modified rhBMP-14 with or without a Protease

Dispase and rhBMP-14 (PeproTech, Inc.) were mixed in microcentrifuge tubes at a molarity ratio of between about 1:100 and about 100:1 and incubated at 37° C. for 10-60 minutes. The mixture was purified with reverse phase HPLC using a C-18 column. The HPLC purified modified rhBMP-14 was used to test the effect of modified rhBMP-14 on osteogenic potential of C2C12 myoblasts.

C2C12 cells (ATCC CRL-1772) were seeded at a density of 25,000 cells/cm² in 24-well plates on day one. The purified modified rhBMP-14 alone, or the same concentration of purified modified rhBMP-14 with the addition of dispase (molarity ratio between about 1:100 and about 100:1) was introduced into wells of the C2C12 cells. C2C12 cells cultured in media alone (without addition of modified rhBMP-14) were used as a negative control.

Figure 16:
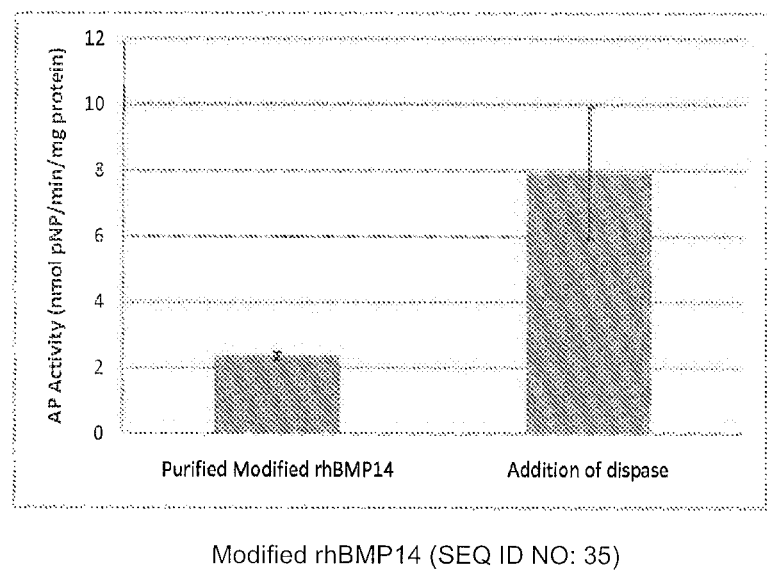
FIG. 16 depicts the expression of alkaline phosphatase in C2C12 cells after being cultured with purified modified rhBMP-14 alone, or the same concentration of purified modified rhBMP-14 with the addition of dispase. The alkaline phosphatase activity in the cells induced by the purified modified rhBMP-14 in combination with dispase was about 235% higher than that induced by the purified modified rhBMP-14 alone.

After 3 days incubation at 37° C., 5% $CO_2$, the AP assay was performed as described above. As shown in FIG. 16, the alkaline phosphatase activity in the cells induced by the purified modified rhBMP-14 in combination with dispase was about 235% higher than that induced by the purified modified rhBMP-14 alone.

Example 34

Figure 17:
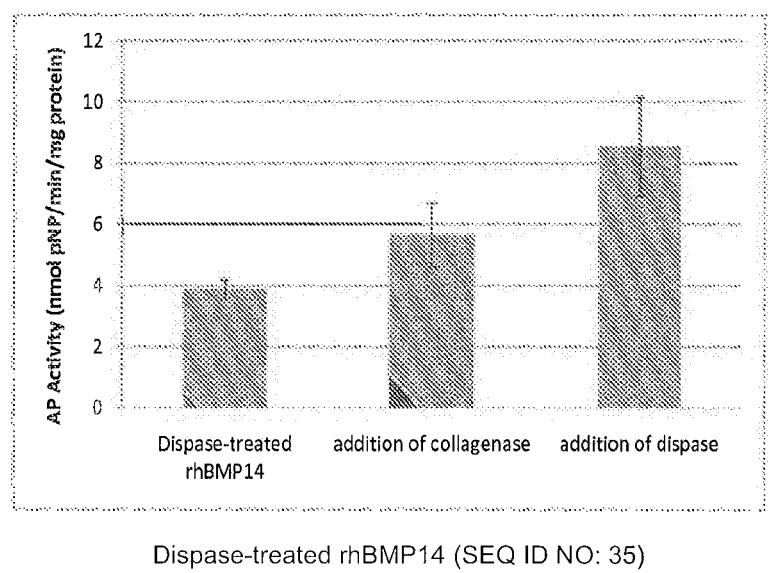
FIG. 17 depicts the expression of alkaline phosphatase in C2C12 cells after being cultured with non-purified modified rhBMP-14, or the same concentration of non-purified modified rhBMP-14 with addition of dispase or collagenase. The alkaline phosphatase activity in the cells induced by the non-purified modified rhBMP-14 in combination with dispase or collagenase were about 120% and 45% higher than that induced by the non-purified modified rhBMP-14 alone, respectively.

Osteoinductive Potential of Modified rhBMP-14 with or without an Additional Protease C2C12 cells were cultured as described above. Non-purified modified rhBMP-14 (1 ug/mL), or the same concentration of non-purified modified rhBMP-14 with addition of dispase or collagenase were introduced into wells of the C2C12 cell. The AP assay was performed as described above. As shown in FIG. 17, the alkaline phosphatase activity in the cells induced by the non-purified modified rhBMP-14 in combination with dispase or collagenase were about 120% and 45% higher than that induced by the non-purified modified rhBMP-14 alone, respectively.

Example 35

Osteoinductive Potential of Mature rhBMP-14 with the Addition of Protease

C2C12 cells (ATCC CRL-1772) were seeded at a density of 25,000 cells/cm² in 24-well plates on day one. The mature rhBMP-14 (1 μg/mL, PeproTech, Inc.), or the same concentration of mature rhBMP-14 with the addition of dispase or collagenase (molarity ratio between about 1:100 and about 100:1) was introduced into wells of the C2C12 cells. C2C12 cells cultured in media alone (without addition of rhBMP-14) were used as a negative control.

After 3 days incubation at 37° C., 5% $CO_2$, the AP assay was performed as described above. The results showed that the alkaline phosphatase activities in cells induced by the mature rhBMP-14 in combination with either dispase or collagenase was about 8-80 times and 53-150% higher than that induced by the mature rhBMP-14 without addition of protease, respectively.

Example 36

Effect of Modified rhBMP-14 on Tendon-specific Gene Expression of Human Adipose-derived Stem Cells Human adipose-derived stem cells (hASC) were isolated from fat tissue of a human donor with research consent. Cells were propagated until the $5^{th}$ passage and seeded at 5,000 cells/cm² in 6-well plates . After one day, the culture media was changed to the differentiation media that contains rhBMP-14 control (100 ng/mL) or dispose-modified rhBMP-14 (100 ng/mL) prepared as shown above.

The cells were cultured in differentiation media for a total of 12 days and the media was changed every 3 days. Cells were collected at different time points and total RNA was extracted and followed by reverse transcription using Applied Biosystems RNA-to-cDNA kit. The tendon-specific gene, scleraxis (SCX), was amplified and quantified using TaqMan Gene Expression Assay kit from Applied Biosystems, Inc. The relative expression (ΔCt) of the target gene was normalized to GAPDH endogenous gene expression and the fold change ($2^{-\Delta\Delta Ct}$) was calculated relative to the hASC control. The SCX gene expressions in cells cultured with dispase-modified rhBMP-14 were about 30% and 39% higher than that in cells cultured with the rhBMP-14 control on day 9 and day 12, respectively.

Example 37

Stability of Modified rhBMP-2 with or without a Protease in Cell Culture

C2C12 cells were cultured, and purified and non-purified modified rhBMP-2 were prepared as described herein. The purified modified rhBMP-2, the non-purified modified rhBMP-2, or the untreated mature rhBMP-2 at the same concentration was introduced into each well of the C2C12 cell seeded 24-well plate on day two. C2C12 cells cultured without addition of rhBMP-2 or modified rhBMP-2 were used as a negative control. After incubation at 37° C., 5% $CO_2$ for different durations (24 hr, 48 hr, or 72 hr), spent culture media were collected from these original 24-well plates and transferred into new 24-well plates containing fresh C2C12 cells seeded the previous day, and the new 24-well plates were incubated at 37° C., 5% $CO_2$ for another 3 days. Cells from the original 24-well plates and new 24-well plates were collected at the end of each culture period and cell lysates were prepared for AP assays and BCA total protein assays.

For the control groups wherein C2C12 cells were cultured for three days in untreated rhBMP-2 spent media collected after 24 hrs, 48 hrs, and 72 hrs, the alkaline phosphatase activity reduced 96%, 98%, and 99% respectively as compared to that of cells cultured for three days with fresh rhBMP-2 media. For the experimental groups in which C2C12 cells were cultured for three days in purified modified rhBMP-2 spent media collected after 24 hrs, 48 hrs, and 72 hrs, the alkaline phosphatase activity reduced 41%, 75%, and 99% respectively as compared to that of cells cultured for three days with fresh purified modified rhBMP-2 media. For the experimental groups in which C2C12 cells were cultured for three days in non-purified modified rhBMP-2 spent media collected after 24 hrs, 48 hrs, and 72 hrs, the alkaline phosphatase activity was maintained at a similar or higher level as compared to that of cells cultured for three days with fresh non-purified modified rhBMP-2 media. This demonstrates that the presence of a protease can further enhance the stability of modified BMP-2 in culture media.

Example 38

Stability of Modified rhBMP-5 with or without a Protease in Cell Culture

C2C12 cells were cultured. Purified dispase-modified rhBMP-5 and purified collagenase-modified rhBMP-5 were prepared as described above. The purified dispase-modified rhBMP-5, the purified collagenase-modified rhBMP-5, the purified modified rhBMP-5 with the addition of either dispase or collagenase, or the untreated mature rhBMP-5 at the same concentration were introduced into each well of the C2C12 cell seeded 24-well plate on day two. C2C12 cells cultured without addition of rhBMP-5 or modified rhBMP-5 were used as a negative control. Cells cultured with either dispase or collagenase were used as enzyme negative controls. After incubation at 37° C., 5% $CO_2$ for different durations (24 hr, 48 hr, or 72 hr), spent culture media were collected from these original 24-well plates and transferred into new 24-well plates containing fresh C2C12 cells seeded the previous day, and the new 24-well plates were incubated at 37° C., 5% $CO_2$ for another 3 days. Cells from the original 24-well plates and new 24-well plates were collected at the end of each culture period, and cell lysates were prepared for AP assays and BCA total protein assays.

The enzyme negative control groups containing either dispase or collagenase showed similar alkaline phosphatase activity as the negative control without any addition of rhBMP5 or modified rhBMP5. For the control groups wherein C2C12 cells were cultured for three days in untreated mature rhBMP-5 spent media collected after 24 hrs, 48 hrs, and 72 hrs, the alkaline phosphatase activity was reduced as compared to that of cells cultured for three days with fresh rhBMP-5 media by 82%, 92% and 94%, respectively.

For the experimental groups in which C2C12 cells were cultured for three days with the spent media of purified dispase-modified rhBMP-5 collected after 24, 48, and 72hrs, the alkaline phosphatase activity increased about 14%, reduced 10%, and 14% respectively as compared to that of cells cultured for three days with fresh purified dispase-modified BMPS media.

For the experimental groups in which C2C12 cells were cultured for three days with the spent media of purified dispase-modified rhBMP-5 and additional dispase collected after 24 hrs, 48 hrs, and 72 hrs, the alkaline phosphatase activity reduced 4%, 16%, and 4% respectively as compared to that of cells cultured for three days with fresh purified dispase-modified rhBMP-5 with the addition of dispase media.

For the experimental groups in which C2C12 cells were cultured for three days in purified collagenase-modified rhBMP-5 spent media collected after 24 hrs, 48 hrs, and 72 hrs, the alkaline phosphatase activity was maintained at similar or higher level as compared to that of cells cultured for three days with fresh purified collagenase-modified rhBMP-5 media. For the experimental groups in which C2C12 cells were cultured for three days in purified collagenase-modified rhBMP-5 with the addition of dispase or collagenase spent media collected after 24 hrs, 48 hrs, and 72 hrs, the alkaline phosphatase activity was also maintained at similar or higher level as compared to that of cells cultured for three days with fresh purified collagenase-modified rhBMP-5 with the addition of dispase or collagenase media.

For the experimental groups in which C2C12 cells were cultured for three days with the spent media of purified dispase-modified rhBMP-5 and additional collagenase collected after 24 hrs, 48 hrs, and 72 hrs, the alkaline phosphatase activity reduced 19%, 11%, and 37% respectively as compared to that of cells cultured for three days with fresh purified dispase-modified rhBMP-5 with addition of collagenase media. Therefore, the modified rhBMP-5 showed higher stability than the unmodified rhBMP-5.

Example 39

Stability of Modified rhBMP-13 with or without a Protease in Cell Culture

C2C12 cells were seeded and cultured for one day. The same quantity of non-modified mature rhBMP-13 or dispase-modified rhBMP-13 without purification was introduced into each well of the C2C12 cell seeded 24-well plate on day two. C2C12 cells cultured without addition of the non-modified rhBMP-13 or modified rhBMP-13 was used as a negative control. After incubation at 37° C., 5% $CO_2$ for different durations (24 hr, 48 hr, or 72 hr), spent culture Media were collected from these original 24-well plates and transferred into new 24-well plates containing fresh C2C12 cells seeded the previous day, and the new 24-well plates were incubated at 37° C., 5% $CO_2$ for 3 days. Cells from the original 24-well plates and new 24-well plates were collected at the end of each culture period, and cell lysates were prepared for AP assays and BCA total protein assays.

For the experimental groups in which C2C12 cells were cultured for three days in non-purified dispase-modified rhBMP-13 spent media collected after 24 hrs, 48 hrs, and 72 hrs, the alkaline phosphatase activities were 44, 46, and 30 times higher than those of cells cultured for three days with non-modified rhBMP-13 spent media collected after 24 hrs, 48 hrs, and 72 hrs, respectively.

Example 40

Stability of Modified rhBMP-14 with or without a Protease in Cell Culture

C2C12 cells were seeded and cultured for one day. The same quantity of non-modified mature rhBMP-14 or dispose-modified rhBMP-14 without purification was introduced into each well of the C2C12 cell seeded 24-well plate on day two. C2C12 cells cultured without addition of the non-modified rhBMP-14 or modified rhBMP-14 was used as a negative control. After incubation at 37° C., 5% $CO_2$ for different durations (24 hr or 48 hr), spent culture media were collected from these original 24-well plates and transferred into new 24-well plates containing fresh C2C12 cells seeded the previous day, and the new 24-well plates were incubated at 37° C., 5% $CO_2$ for 3 days. Cells from the original 24-well plates and new 24-well plates were collected at the end of each culture period, and cell lysates were prepared for AP assays and BCA total protein assays.

For the experimental groups in which C2C12 cells were cultured for three days in non-purified dispase modified rhBMP-14 spent media collected after 24 hrs or 48 hrs, the alkaline phosphatase activities were 7.5% and 103% higher than those of cells cultured for three days with non-modified rhBMP-14 spent media collected after 24 hrs and 48 hrs, respectively.

Example 41

Stability of Modified rhBMPs-4 and 7 with or without a Protease in Cell Culture

C2C12 cells are cultured, and purified and non-purified modified rhBMP-4 and 7 are prepared as described above. Each of the purified modified rhBMP-4 and 7, the non-purified modified rhBMP-4 and 7, and the untreated mature rhBMP-4 and 7 at the same concentration is introduced into each well of the C2C12 cell seeded 24-well plate on day two. C2C12 cells cultured without addition of rhBMP-4 and 7 or modified rhBMP-4 and 7 are used as a negative control. After incubation at 37° C., 5% $CO_2$ for different durations (24 hr, 48 hr, or 72 hr), spent culture media are collected from these original 24-well plates and transferred into new 24-well plates containing fresh C2C12 cells seeded the previous day, and the new 24-well plates are incubated at 37° C., 5% $CO_2$ for another 3 days. Cells from the original 24-well plates and new 24-well plates are collected at the end of each culture period, and cell lysates are prepared for AP assays and BCA total protein assays.

For the control groups wherein C2C12 cells are cultured for three days in untreated rhBMP-4 or 7 spent media collected after 24 hrs, 48 hrs, and 72 hrs, the alkaline phosphatase activity is reduced as compared to that of cells cultured for three days with fresh rhBMP-4 or 7 media, respectively. For the experimental groups in which C2C12 cells are cultured for three days in purified modified rhBMP-4 or 7 spent media collected after 24 hrs, 48 hrs, and 72 hrs, the alkaline phosphatase activity is also reduced less than for the control group. For the experimental groups in which C2C12 cells are cultured for three days in non-purified modified rhBMP-4 or 7 spent media collected after 24 hrs, 48 hrs, and 72 hrs, however, the alkaline phosphatase activity is maintained at a similar or higher level as compared to that of cells cultured for three days with fresh non-purified modified rhBMP-4 or 7 media, respectively. This demonstrates that the presence of a protease can further enhance the stability of modified BMP-4 or 7 in culture media.

Example 42

Stability of Modified rhBMP-2 with or without a Protease on Shelf

Purified and non-purified modified rhBMP-2 were prepared as described herein. Aliquots of the purified and non-purified modified rhBMP-2 at the same volume and concentration were incubated at 37° C. for different durations (2 days to 2 weeks). After each time point, one aliquot from each group was transferred into -20° C. freezer until the last time point was completed. The aliquots of purified modified rhBMP-2 or non-purified modified rhBMP-2 from different time points were introduced into each well of the C2C12 cell cultured as described above. C2C12 cells cultured without the addition of rhBMP-2 or collagenase were used as a negative control. After 3 days incubation at 37° C., 5% $CO_2$, the AP assay as described above was performed.

The alkaline phosphatase activity of cells cultured with purified modified rhBMP-2 on shelf (37° C.) for 7 days or 14 days reduced 94% and 98% respectively as compared to that of cells cultured with purified modified rhBMP-2 on shelf (37° C.) for 2 days. The alkaline phosphatase activity of cells cultured with non-purified modified rhBMP-2 on shelf (37° C.) for 7 days or 14 days reduced 7% and 6% respectively as compared to that of cells cultured with non-purified modified rhBMP-2 on shelf (37° C.) for 2 days. This demonstrates that the presence of a protease can further enhance the stability of modified BMP-2 on shelf.

Example 43

Stability of Modified rhBMP-5 with or without a Protease on Shelf

Purified modified rhBMP-5 was prepared as described in Example 11 above. Aliquots of the purified dispase-modified rhBMP-5, the purified dispase-modified rhBMP-5 with the addition of dispase or collagenase, the purified collagenase-modified rhBMP-5, or the untreated mature rhBMP-5 at the same volume and concentration were incubated at 37° C. for different durations (1 day to 7 days). After each time point, one aliquot from each group was transferred into −20° C. freezer until the last time point was completed. All the aliquots were thawed at the same time and were introduced into each well of the C2C12 cell cultured as described above. C2C12 cells cultured without the addition of rhBMP-5 or modified rhBMP-5 were used as a negative control. After 3 days incubation at 37° C., 5% $CO_2$, the AP assay as described above was performed.

The alkaline phosphatase activity of cells cultured with purified dispase-modified rhBMP-5 on shelf (37° C.) for 1 day was reduced about 99% as compared to that of cells cultured with fresh purified modified rhBMP-5, but was about 99 times higher than the alkaline phosphatase activity of the untreated mature rhBMP-5 control after 1 day of incubation. The alkaline phosphatase activity of cells cultured with purified collagenase-modified rhBMP-5 on shelf (37° C.) for 3 days or 7 days was reduced 27% and 97% respectively as compared to that of cells cultured with fresh purified collagenase-modified rhBMP-5. However, the alkaline phosphatase activity of cells cultured with purified dispase-modified rhBMP-5 with the addition of collagenase on shelf (37° C.) for 1 day, 3 days, or 7 days was reduced 17%, 36%, and 61% respectively as compared to that of cells cultured with fresh purified dispase-modified rhBMP-5 with the addition of collagenase. This demonstrates that the presence of a protease can further enhance the stability of modified BMP-5 on shelf.

In addition, the alkaline phosphatase activity of cells cultured with purified dispase-modified rhBMP-5 with the addition of collagenase on shelf (37° C.) for 1 day, 3 days, or 7 days was 1460 times, 990 times, and 603 times higher than that of cells cultured with non-modified mature rhBMP-5 after 1day, 3 day, and 7 day shelf-life, respectively.

Example 44

Stability of Modified rhBMPs-4 and 7 with or without a Protease

Purified and non-purified modified rhBMP-4 and 7 are prepared as described in Examples above. Aliquots of each of the purified and non-purified modified rhBMP-4 or 7 at the same volume and concentration are incubated at 37° C. for different durations (2 days to 2 weeks). After each time point, one aliquot from each group is transferred into −20° C. freezer until the last time point is completed. The aliquots of each of the purified modified rhBMP-4 or 7, or non-purified modified rhBMP-4 or 7 from different time points are introduced into each well of the C2C12 cell cultured as described above. C2C12 cells cultured without the addition of rhBMP-4 or 7 or collagenase are used as a negative control. After 3 days incubation at 37° C., 5% $CO_2$, the AP assay as described above is perfoi fined.

The alkaline phosphatase activity of cells cultured with purified modified rhBMP-4 or 7 on shelf (37° C.) for 7 days or 14 days is reduced as compared to that of cells cultured with purified modified rhBMP-4 or 7 on shelf (37° C.) for 2 days. The alkaline phosphatase activity of cells cultured with non-purified modified rhBMP-4 or 7 on shelf (37° C.) for 7 days or 14 days is reduced less than that of cells cultured with purified modified rhBMP-4 or 7, respectively. This demonstrates that the presence of a protease can further enhance the stability of modified BMP-4 and 7 on shelf.

Example 45

Stability of Modified rhBMP13 with or without a Protease on Shelf

The same amount of rhBMP13 without treatment and rhBMP13 with dispase or collagenase treatment but without purification were prepared and incubated at 37° C. for different durations (1 day to 10days). After each time point, one aliquot from each group was transferred into −20° C. freezer until the last time point was completed. All aliquots were thawed at the same time and were introduced into each well of the C2C12 cell cultured as described above. C2C12 cells cultured without the addition of rhBMP-13 or modified rhBMP-13 were used as a negative control. After 3 days incubation at 37° C., 5% $CO_2$, the AP assay as described above was performed.

The alkaline phosphatase activity in cells cultured with non-purified collagenase modified rhBMP-13 stored at 37° C. for 3 clays or 10 days reduced 32% and 52%, respectively, as compared to that in cells cultured with fresh non-purified collagenase modified rhBMP-13 without storage; however, they were still 291% and 174% higher than that of cells cultured with non-modified rhBMP-13 stored at 37° C. for 3 days or 10 days. The alkaline phosphatase activity in cells cultured with non-purified dispase modified rhBMP-13 (stored at 37° C.) for 3 days or 10 days were 79% and 27% higher than that of cells cultured with non-purified rhBMP-13 (stored at 37° C.) for 3 days or 10 days.

Example 46

Stability of Modified rhBMP14 with or without a Protease on Shelf

The same amount of rhBMP14 without treatment and rhBMP14 with collagenase treatment but without purification were prepared and incubated at 37° C. for different durations (1 day to 10days). After each time point, one aliquot from each group was transferred into −20° C. freezer until the last time point was completed. The aliquots of non-modified rhBMP-14 or non-purified collagenase modified rhBMP-14 from different time points were introduced into each well of the C2C12 cell cultured as described above. C2C12 cells cultured without the addition of rhBMP-14 or modified rhBMP-14 were used as a negative control. After 3 days incubation at 37° C., 5% $CO_2$, the AP assay as described above was performed.

The alkaline phosphatase activity of cells cultured with non-purified collagenase modified rhBMP-14 on shelf (37° C.) for 3 days or 7 days only reduced 11% and 12.7% respectively as compared to that of cells cultured with fresh non-purified collagenase modified rhBMP-14, while the alkaline phosphatase activity of cells cultured with non-modified rhBMP-14 on shelf (37° C.) for 3 days or 7 days reduced 25% and 39% respectively as compared to that of cells cultured with fresh non-modified rhBMP-14.

What is claimed:

1. A peptide consisting of an amino acid sequence selected from SEQ ID NOs: 20, 21, 22, 24, 25, 26, 27 and 28.

2. A pharmaceutical composition comprising the peptide of claim 1 and a pharmaceutically acceptable carrier.

3. A method of increasing a biological activity of a cell, comprising treating the cell with an effective amount of the composition of claim 2, wherein the biological activity is selected from the group consisting of osteoinductive activity, chondroinductive activity, ligament/tendon differentiating activity, osteogenic activity and growth factor activity.

4. The method of claim 3, wherein the cell is derived from placenta, bone marrow, adipose tissue, blood vessel, amniotic fluid, synovial fluid, synovial membrane, pericardium, periosteum, dura, peripheral blood, umbilical blood, menstrual blood, teeth, nucleus pulposus, brain, skin, hair follicle, intestinal crypt, neural tissue, or muscle.

5. The method of claim 3, wherein the cell is a progenitor cell or adult stem cell.

6. The method of claim 3, wherein the cell is a pluripotent stem cell.

7. The method of claim 3, wherein the cell is selected from the group consisting of mesenchymal stem cells, adipose-derived stem cells, embryonic stem cells, progenitor cells, differentiated cells, undifferentiated cells, and induced pluripotent stem cells.

8. The method of claim 3, wherein the biological activity is an osteoinductive activity.

9. The method of claim 3, wherein the biological activity is a chondroinductive activity.

10. The method of claim 3, wherein the biological activity is a ligament/tendon differentiating activity.

11. The method of claim 3, wherein the biological activity is an osteogenic activity.

12. The method of claim 3, wherein the biological activity is a growth factor activity.

13. The method of claim 3, wherein the cell is in a tissue.

14. The method of claim 13, wherein the tissue is a bone, cartilage, or connective tissue.

15. The method of claim 3, wherein the composition further comprises a protease that is not bone morphogenetic protein-1 (BMP-1).

16. The method of claim 15, wherein the protease is selected from the group consisting of dispase, collagenase and a mixture thereof.

17. The method of claim 15, wherein the protease is collagenase.

18. The method of claim 15, wherein the protease is dispase.

19. A method of increasing a biological activity of a cell, comprising treating the cell with an effective amount of a peptide consisting of an amino acid sequence selected from SEQ ID NOs: 20-28, wherein the biological activity is selected from the group consisting of osteoinductive activity, chondroinductive activity, ligament/tendon differentiating activity, osteogenic activity and growth factor activity.

* * * * *

SEQUENCE LISTING

```
<160> NUMBER OF SEQ ID NOS: 77

<210> SEQ ID NO 1
<211> LENGTH: 396
<212> TYPE: PRT
<213> ORGANISM: homo sapiens

<400> SEQUENCE: 1

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
```

```
                65                  70                  75                  80
Asp Leu Tyr Arg Arg His Ser Gly Gln Pro Gly Ser Pro Ala Pro Asp
                    85                  90                  95

His Arg Leu Glu Arg Ala Ala Ser Arg Ala Asn Thr Val Arg Ser Phe
            100                 105                 110

His His Glu Glu Ser Leu Glu Leu Pro Glu Thr Ser Gly Lys Thr
        115                 120                 125

Thr Arg Arg Phe Phe Phe Asn Leu Ser Ser Ile Pro Thr Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 2
<211> LENGTH: 472
<212> TYPE: PRT
<213> ORGANISM: homo sapiens

<400> SEQUENCE: 2

Met Ala Gly Ala Ser Arg Leu Leu Phe Leu Trp Leu Gly Cys Phe Cys
1               5                   10                  15

Val Ser Leu Ala Gln Gly Glu Arg Pro Lys Pro Pro Phe Pro Glu Leu
            20                  25                  30

Arg Lys Ala Val Pro Gly Asp Arg Thr Ala Gly Gly Gly Pro Asp Ser
        35                  40                  45
```

```
Glu Leu Gln Pro Gln Asp Lys Val Ser Glu His Met Leu Arg Leu Tyr
 50                  55                  60

Asp Arg Tyr Ser Thr Val Gln Ala Ala Arg Thr Pro Gly Ser Leu Glu
 65                  70                  75                  80

Gly Gly Ser Gln Pro Trp Arg Pro Arg Leu Leu Arg Glu Gly Asn Thr
                 85                  90                  95

Val Arg Ser Phe Arg Ala Ala Ala Glu Thr Leu Glu Arg Lys Gly
            100                 105                 110

Leu Tyr Ile Phe Asn Leu Thr Ser Leu Thr Lys Ser Glu Asn Ile Leu
            115                 120                 125

Ser Ala Thr Leu Tyr Phe Cys Ile Gly Glu Leu Gly Asn Ile Ser Leu
145                 150                     155                 160

Ile Gln Ile Asp Leu Ser Ala Trp Thr Leu Lys Phe Ser Arg Asn Gln
                165                 170                 175

Ser Gln Leu Leu Gly His Leu Ser Val Asp Met Ala Lys Ser His Arg
            180                 185                 190

Asp Ile Met Ser Trp Leu Ser Lys Asp Ile Thr Gln Phe Leu Arg Lys
            195                 200                 205

Ala Lys Glu Asn Glu Glu Phe Leu Ile Gly Phe Asn Ile Thr Ser Lys
210                 215                 220

Gly Arg Gln Leu Pro Lys Arg Leu Pro Phe Pro Glu Pro Tyr Ile
225                 230                 235                 240

Leu Val Tyr Ala Asn Asp Ala Ala Ile Ser Glu Pro Glu Ser Val Val
            245                 250                 255

Ser Ser Leu Gln Gly His Arg Asn Phe Pro Thr Gly Thr Val Pro Lys
            260                 265                 270

Trp Asp Ser His Ile Arg Ala Ala Leu Ser Ile Glu Arg Arg Lys Lys
        275                 280                 285

Arg Ser Thr Gly Val Leu Leu Pro Leu Gln Asn Asn Glu Leu Pro Gly
        290                 295                 300

Ala Glu Tyr Gln Tyr Lys Lys Asp Glu Val Trp Glu Glu Arg Lys Pro
305                 310                 315                 320

Tyr Lys Thr Leu Gln Ala Gln Ala Pro Glu Lys Ser Lys Asn Lys Lys
            325                 330                 335

Lys Gln Arg Lys Gly Pro His Arg Lys Ser Gln Thr Leu Gln Phe Asp
            340                 345                 350

Glu Gln Thr Leu Lys Lys Ala Arg Arg Lys Gln Trp Ile Glu Pro Arg
            355                 360                 365

Asn Cys Ala Arg Arg Tyr Leu Lys Val Asp Phe Ala Asp Ile Gly Trp
370                 375                 380

Ser Glu Trp Ile Ile Ser Pro Lys Ser Phe Asp Ala Tyr Tyr Cys Ser
385                 390                 395                 400

Gly Ala Cys Gln Phe Pro Met Pro Lys Ser Leu Lys Pro Ser Asn His
            405                 410                 415

Ala Thr Ile Gln Ser Ile Val Arg Ala Val Gly Val Val Pro Gly Ile
            420                 425                 430

Pro Glu Pro Cys Cys Val Pro Glu Lys Met Ser Ser Leu Ser Ile Leu
            435                 440                 445

Phe Phe Asp Glu Asn Lys Asn Val Val Leu Lys Val Tyr Pro Asn Met
450                 455                 460

Thr Val Glu Ser Cys Ala Cys Arg
```

-continued

```
<210> SEQ ID NO 3
<211> LENGTH: 408
<212> TYPE: PRT
<213> ORGANISM: homo sapiens

<400> SEQUENCE: 3

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365
```

```
Pro Lys Ala Cys Cys Val Pro Thr Glu Leu Ser Ala Ile Ser Met Leu
    370             375                 380

Tyr Leu Asp Glu Tyr Asp Lys Val Val Leu Lys Asn Tyr Gln Glu Met
385             390                 395                 400

Val Val Glu Gly Cys Gly Cys Arg
                405

<210> SEQ ID NO 4
<211> LENGTH: 454
<212> TYPE: PRT
<213> ORGANISM: homo sapiens

<400> SEQUENCE: 4

Met His Leu Thr Val Phe Leu Leu Lys Gly Ile Val Gly Phe Leu Trp
1               5                   10                  15

Ser Cys Trp Val Leu Val Gly Tyr Ala Lys Gly Gly Leu Gly Asp Asn
                20                  25                  30

His Val His Ser Ser Phe Ile Tyr Arg Arg Leu Arg Asn His Glu Arg
            35                  40                  45

Arg Glu Ile Gln Arg Glu Ile Leu Ser Ile Leu Gly Leu Pro His Arg
        50                  55                  60

Pro Arg Pro Phe Ser Pro Gly Lys Gln Ala Ser Ser Ala Pro Leu Phe
65                  70                  75                  80

Met Leu Asp Leu Tyr Asn Ala Met Thr Asn Glu Glu Asn Pro Glu Glu
                85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
        115                 120                 125

Leu Ser Arg Thr Thr Pro Leu Thr Thr Gln Ser Pro Pro Leu Ala Ser
    130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
        195                 200                 205

Phe Glu Asn Glu Thr Ile Lys Ile Ser Ile Tyr Gln Ile Ile Lys Glu
    210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
    290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser Ser His Gln Asp Ser Ser
                325                 330                 335
```

```
Arg Met Ser Ser Val Gly Asp Tyr Asn Thr Ser Glu Gln Lys Gln Ala
            340                 345                 350

Cys Lys Lys His Glu Leu Tyr Val Ser Phe Arg Asp Leu Gly Trp Gln
            355                 360                 365

Asp Trp Ile Ile Ala Pro Glu Gly Tyr Ala Ala Phe Tyr Cys Asp Gly
        370                 375                 380

Glu Cys Ser Phe Pro Leu Asn Ala His Met Asn Ala Thr Asn His Ala
385                 390                 395                 400

Ile Val Gln Thr Leu Val His Leu Met Phe Pro Asp His Val Pro Lys
                405                 410                 415

Pro Cys Cys Ala Pro Thr Lys Leu Asn Ala Ile Ser Val Leu Tyr Phe
                420                 425                 430

Asp Asp Ser Ser Asn Val Ile Leu Lys Lys Tyr Arg Asn Met Val Val
            435                 440                 445

Arg Ser Cys Gly Cys His
    450

<210> SEQ ID NO 5
<211> LENGTH: 513
<212> TYPE: PRT
<213> ORGANISM: homo sapiens

<400> SEQUENCE: 5

Met Pro Gly Leu Gly Arg Arg Ala Gln Trp Leu Cys Trp Trp Trp Gly
1               5                   10                  15

Leu Leu Cys Ser Cys Cys Gly Pro Pro Leu Arg Pro Pro Leu Pro
            20                  25                  30

Ala Ala Ala Ala Ala Ala Gly Gly Gln Leu Leu Gly Asp Gly Gly
            35                  40                  45

Ser Pro Gly Arg Thr Glu Gln Pro Pro Ser Pro Gln Ser Ser Ser
50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
            100                 105                 110

Gln Gln Gln Gln Gln Leu Pro Arg Gly Glu Pro Pro Pro Gly Arg
        115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
            180                 185                 190

Gly Ser Gly Gly Ala Ser Pro Leu Thr Ser Ala Gln Asp Ser Ala Phe
        195                 200                 205

Leu Asn Asp Ala Asp Met Val Met Ser Phe Val Asn Leu Val Glu Tyr
    210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
```

```
                245                 250                 255
Arg Ile Tyr Lys Asp Cys Val Met Gly Ser Phe Lys Asn Gln Thr Phe
            260                 265                 270

Leu Ile Ser Ile Tyr Gln Val Leu Gln Glu His Gln His Arg Asp Ser
        275                 280                 285

Asp Leu Phe Leu Leu Asp Thr Arg Val Val Trp Ala Ser Glu Glu Gly
    290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
            340                 345                 350

Tyr Asp Lys Gln Pro Phe Met Val Ala Phe Lys Val Ser Glu Val
        355                 360                 365

His Val Arg Thr Thr Arg Ser Ala Ser Ser Arg Arg Gln Gln Ser
    370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
            420                 425                 430

Pro Lys Gly Tyr Ala Ala Asn Tyr Cys Asp Gly Glu Cys Ser Phe Pro
        435                 440                 445

Leu Asn Ala His Met Asn Ala Thr Asn His Ala Ile Val Gln Thr Leu
    450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
            500                 505                 510

His

<210> SEQ ID NO 6
<211> LENGTH: 431
<212> TYPE: PRT
<213> ORGANISM: homo sapiens

<400> SEQUENCE: 6

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
```

```
                    100                 105                 110
Thr Gln Gly Pro Pro Leu Ala Ser Leu Gln Asp Ser His Phe Leu Thr
                115                 120                 125

Asp Ala Asp Met Val Met Ser Phe Val Asn Leu Val Glu His Asp Lys
130                 135                 140

Glu Phe Phe His Pro Arg Tyr His Arg Glu Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
                195                 200                 205

Phe Leu Leu Asp Ser Arg Thr Leu Trp Ala Ser Glu Glu Gly Trp Leu
                210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
                275                 280                 285

Arg Ser Ile Arg Ser Thr Gly Ser Lys Gln Arg Ser Gln Asn Arg Ser
                290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
                370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430

<210> SEQ ID NO 7
<211> LENGTH: 402
<212> TYPE: PRT
<213> ORGANISM: homo sapiens

<400> SEQUENCE: 7

Met Thr Ala Leu Pro Gly Pro Leu Trp Leu Leu Gly Leu Ala Leu Cys
1               5                   10                  15

Ala Leu Gly Gly Gly Gly Pro Gly Leu Arg Pro Pro Gly Cys Pro
                20                  25                  30

Gln Arg Arg Leu Gly Ala Arg Glu Arg Arg Asp Val Gln Arg Glu Ile
                35                  40                  45
```

```
Leu Ala Val Leu Gly Leu Pro Gly Arg Pro Arg Ala Pro Pro
    50              55                  60
Ala Ala Ser Arg Leu Pro Ala Ser Ala Pro Leu Phe Met Leu Asp Leu
65              70                  75                  80
Tyr His Ala Met Ala Gly Asp Asp Glu Asp Gly Ala Pro Ala Glu
                85                  90                  95
Arg Arg Leu Gly Arg Ala Asp Leu Val Met Ser Phe Val Asn Met Val
                100                 105                 110
Glu Arg Asp Arg Ala Leu Gly His Gln Glu Pro His Trp Lys Glu Phe
                115                 120                 125
Arg Phe Asp Leu Thr Gln Ile Pro Ala Gly Glu Ala Val Thr Ala Ala
130                 135                 140
Glu Phe Arg Ile Tyr Lys Val Pro Ser Ile His Leu Leu Asn Arg Thr
145                 150                 155                 160
Leu His Val Ser Met Phe Gln Val Val Gln Glu Gln Ser Asn Arg Glu
                165                 170                 175
Ser Asp Leu Phe Phe Leu Asp Leu Gln Thr Leu Arg Ala Gly Asp Glu
                180                 185                 190
Gly Trp Leu Val Leu Asp Val Thr Ala Ala Ser Asp Cys Trp Leu Leu
                195                 200                 205
Lys Arg His Lys Asp Leu Gly Leu Arg Leu Tyr Val Glu Thr Glu Asp
210                 215                 220
Gly His Ser Val Asp Pro Gly Leu Ala Gly Leu Leu Gly Gln Arg Ala
225                 230                 235                 240
Pro Arg Ser Gln Gln Pro Phe Val Val Thr Phe Phe Arg Ala Ser Pro
                245                 250                 255
Ser Pro Ile Arg Thr Pro Arg Ala Val Arg Pro Leu Arg Arg Arg Gln
                260                 265                 270
Pro Lys Lys Ser Asn Glu Leu Pro Gln Ala Asn Arg Leu Pro Gly Ile
                275                 280                 285
Phe Asp Asp Val His Gly Ser His Gly Arg Gln Val Cys Arg Arg His
290                 295                 300
Glu Leu Tyr Val Ser Phe Gln Asp Leu Gly Trp Leu Asp Trp Val Ile
305                 310                 315                 320
Ala Pro Gln Gly Tyr Ser Ala Tyr Tyr Cys Glu Gly Glu Cys Ser Phe
                325                 330                 335
Pro Leu Asp Ser Cys Met Asn Ala Thr Asn His Ala Ile Leu Gln Ser
                340                 345                 350
Leu Val His Leu Met Met Pro Asp Ala Val Pro Lys Ala Cys Cys Ala
                355                 360                 365
Pro Thr Lys Leu Ser Ala Thr Ser Val Leu Tyr Tyr Asp Ser Ser Asn
370                 375                 380
Asn Val Ile Leu Arg Lys His Arg Asn Met Val Val Lys Ala Cys Gly
385                 390                 395                 400
Cys His

<210> SEQ ID NO 8
<211> LENGTH: 429
<212> TYPE: PRT
<213> ORGANISM: homo sapiens

<400> SEQUENCE: 8

Met Cys Pro Gly Ala Leu Trp Val Ala Leu Pro Leu Leu Ser Leu Leu
1               5                   10                  15
```

```
Ala Gly Ser Leu Gln Gly Lys Pro Leu Gln Ser Trp Gly Arg Gly Ser
            20                  25                  30

Ala Gly Gly Asn Ala His Ser Pro Leu Gly Val Pro Gly Gly Gly Leu
            35                  40                  45

Pro Glu His Thr Phe Asn Leu Lys Met Phe Leu Glu Asn Val Lys Val
50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
            85                  90                  95

Thr Ser Asp Lys Ser Thr Thr Pro Ala Ser Asn Ile Val Arg Ser Phe
            100                 105                 110

Ser Met Glu Asp Ala Ile Ser Ile Thr Ala Thr Glu Asp Phe Pro Phe
            115                 120                 125

Gln Lys His Ile Leu Leu Phe Asn Ile Ser Ile Pro Arg His Glu Gln
            130                 135                 140

Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
            165                 170                 175

Asp Gly Thr Asp Ala Trp Asp Ser Ala Thr Glu Thr Lys Thr Phe Leu
            180                 185                 190

Val Ser Gln Asp Ile Gln Asp Glu Gly Trp Glu Thr Leu Glu Val Ser
            195                 200                 205

Ser Ala Val Lys Arg Trp Val Arg Ser Asp Ser Thr Lys Ser Lys Asn
210                 215                 220

Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
            245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
            275                 280                 285

Lys Asp Gly Ser Thr Glu Ala Gly Glu Ser Ser His Glu Glu Asp Thr
            290                 295                 300

Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
            325                 330                 335

Glu Asp Ile Gly Trp Asp Ser Trp Ile Ile Ala Pro Lys Glu Tyr Glu
            340                 345                 350

Ala Tyr Glu Cys Lys Gly Gly Cys Phe Phe Pro Leu Ala Asp Asp Val
            355                 360                 365

Thr Pro Thr Lys His Ala Ile Val Gln Thr Leu Val His Leu Lys Phe
            370                 375                 380

Pro Thr Lys Val Gly Lys Ala Cys Cys Val Pro Thr Lys Leu Ser Pro
385                 390                 395                 400

Ile Ser Val Leu Tyr Lys Asp Asp Met Gly Val Pro Thr Leu Lys Tyr
            405                 410                 415

His Tyr Glu Gly Met Ser Val Ala Glu Cys Gly Cys Arg
            420                 425
```

<210> SEQ ID NO 9
<211> LENGTH: 424
<212> TYPE: PRT
<213> ORGANISM: homo sapiens

<400> SEQUENCE: 9

Met Gly Ser Leu Val Leu Thr Leu Cys Ala Leu Phe Cys Leu Ala Ala
1               5                   10                  15

Tyr Leu Val Ser Gly Ser Pro Ile Met Asn Leu Glu Gln Ser Pro Leu
            20                  25                  30

Glu Glu Asp Met Ser Leu Phe Gly Asp Val Phe Ser Glu Gln Asp Gly
        35                  40                  45

Val Asp Phe Asn Thr Leu Leu Gln Ser Met Lys Asp Glu Phe Leu Lys
    50                  55                  60

Thr Leu Asn Leu Ser Asp Ile Pro Thr Gln Asp Ser Ala Lys Val Asp
65                  70                  75                  80

Pro Pro Glu Tyr Met Leu Glu Leu Tyr Asn Lys Phe Ala Thr Asp Arg
                85                  90                  95

Thr Ser Met Pro Ser Ala Asn Ile Ile Arg Ser Phe Lys Asn Glu Asp
            100                 105                 110

Leu Phe Ser Gln Pro Val Ser Phe Asn Gly Leu Arg Lys Tyr Pro Leu
        115                 120                 125

Leu Phe Asn Val Ser Ile Pro His His Glu Glu Val Ile Met Ala Glu
    130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
            180                 185                 190

Gly Thr Asn Ser Glu Trp Glu Thr Phe Asp Val Thr Asp Ala Ile Arg
        195                 200                 205

Arg Trp Gln Lys Ser Gly Ser Ser Thr His Gln Leu Glu Val His Ile
    210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
            260                 265                 270

Met Ile Ser His Glu Gln Leu Pro Glu Leu Asp Asn Leu Gly Leu Asp
        275                 280                 285

Ser Phe Ser Ser Gly Pro Gly Glu Glu Ala Leu Leu Gln Met Arg Ser
    290                 295                 300

Asn Ile Ile Tyr Asp Ser Thr Ala Arg Ile Arg Arg Asn Ala Lys Gly
305                 310                 315                 320

Asn Tyr Cys Lys Arg Thr Pro Leu Tyr Ile Asp Phe Lys Glu Ile Gly
                325                 330                 335

Trp Asp Ser Trp Ile Ile Ala Pro Pro Gly Tyr Glu Ala Tyr Glu Cys
            340                 345                 350

Arg Gly Val Cys Asn Tyr Pro Leu Ala Glu His Leu Thr Pro Thr Lys
        355                 360                 365

His Ala Ile Ile Gln Ala Leu Val His Leu Lys Asn Ser Gln Lys Ala
    370                 375                 380

-continued

```
Ser Lys Ala Cys Cys Val Pro Thr Lys Leu Glu Pro Ile Ser Ile Leu
385                 390                 395                 400

Tyr Leu Asp Lys Gly Val Val Thr Tyr Lys Phe Lys Tyr Glu Gly Met
            405                 410                 415

Ala Val Ser Glu Cys Gly Cys Arg
            420

<210> SEQ ID NO 10
<211> LENGTH: 407
<212> TYPE: PRT
<213> ORGANISM: homo sapiens

<400> SEQUENCE: 10

Met Val Leu Ala Ala Pro Leu Leu Gly Phe Leu Leu Leu Ala Leu
1               5                   10                  15

Glu Leu Arg Pro Arg Gly Glu Ala Glu Gly Pro Ala Ala Ala
            20                  25                  30

Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335
```

```
Lys Ala Asn Tyr Cys Ser Gly Gln Cys Glu Tyr Met Phe Met Gln Lys
                340             345                 350

Tyr Pro His Thr His Leu Val Gln Gln Ala Asn Pro Arg Gly Ser Ala
            355                 360                 365

Gly Pro Cys Cys Thr Pro Thr Lys Met Ser Pro Ile Asn Met Leu Tyr
            370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 11
<211> LENGTH: 461
<212> TYPE: PRT
<213> ORGANISM: homo sapiens

<400> SEQUENCE: 11

Met Asp Leu Ser Ala Ala Ala Leu Cys Leu Trp Leu Leu Ser Ala
1               5                   10                  15

Cys Arg Pro Arg Asp Gly Leu Glu Ala Ala Val Leu Arg Ala Ala
                20                  25                  30

Gly Ala Gly Pro Ala Trp Ser Pro Gly Gly Gly Gly Arg Thr
            35                  40                  45

Leu Ala Arg Ala Pro Gly Pro Ser Ala Leu Gln Ala Ala Val Pro
            50                  55                  60

Gly Pro Arg Ala Val Arg Arg Ala Ala Gly Ser Gly Phe Arg Asn Gly
65                  70                  75                  80

Ser Val Val Pro His His Phe Met Met Ser Leu Tyr Arg Ser Leu Ala
                85                  90                  95

Gly Arg Ala Pro Val Ala Ala Ser Gly His Gly Arg Val Asp Thr
            100                 105                 110

Ile Thr Gly Phe Thr Asp Gln Ala Thr Gln Asp Glu Thr Ala Ala Ala
                115                 120                 125

Glu Pro Gly Gln Ser Phe Leu Phe Asp Val Ser Ser Leu Ser Glu Ala
130                 135                 140

Asp Glu Val Val Asn Ala Glu Leu Arg Val Leu Arg Arg Ser Pro
145                 150                 155                 160

Glu Pro Asp Arg Asp Ser Ala Thr Leu Leu Pro Arg Leu Leu Leu Ser
                165                 170                 175

Thr Cys Pro Asp Glu Ala Gly Thr Ala His Leu Leu His Ser Arg Ala
            180                 185                 190

Ala Glu Pro Leu Gly Gly Ala Arg Trp Glu Ala Phe Asp Val Thr Asp
                195                 200                 205

Ala Val Gln Ser His Arg Arg Trp Pro Arg Ala Ser Arg Lys Phe Cys
210                 215                 220

Leu Val Leu Arg Ala Val Thr Ala Ser Glu Ser Ser Pro Leu Ala Leu
225                 230                 235                 240

Arg Arg Leu Gly Phe Gly Trp Pro Gly Gly Gly Asp Gly Gly Thr
                245                 250                 255

Ala Ala Glu Glu Arg Ala Leu Leu Val Ile Ser Ser Arg Thr Gln Arg
                260                 265                 270

Lys Glu Ser Leu Phe Arg Glu Ile Arg Ala Gln Ala Arg Ala Leu Arg
                275                 280                 285

Ala Ala Ala Glu Pro Pro Pro Asp Pro Gly Pro Gly Ala Gly Ser Arg
```

```
                290             295             300
Lys Ala Asn Leu Gly Gly Arg Arg Arg Thr Ala Leu Ala Gly
305                 310             315                 320

Thr Arg Gly Ala Gln Gly Ser Gly Gly Gly Gly Gly Gly Gly
                325             330             335

Gly Gly Gly Gly Gly Gly Gly Gly Gly Ala Gly Arg Gly His
                340             345             350

Gly Arg Arg Gly Arg Ser Arg Cys Ser Arg Lys Ser Leu His Val Asp
            355             360             365

Phe Lys Glu Leu Gly Trp Asp Asp Trp Ile Ile Ala Pro Leu Asp Tyr
            370             375             380

Glu Ala Tyr His Cys Glu Gly Val Cys Asp Phe Pro Leu Arg Ser His
385                 390             395                 400

Leu Glu Pro Thr Asn His Ala Ile Ile Gln Thr Leu Leu Asn Ser Met
                405             410             415

Ala Pro Asp Ala Ala Pro Ala Ser Cys Cys Val Pro Ala Arg Leu Ser
                420             425             430

Pro Ile Ser Ile Leu Tyr Ile Asp Ala Ala Asn Asn Val Val Tyr Lys
                435             440             445

Gln Tyr Glu Asp Met Val Val Glu Ala Cys Gly Cys Arg
450                 455             460

<210> SEQ ID NO 12
<211> LENGTH: 455
<212> TYPE: PRT
<213> ORGANISM: homo sapiens

<400> SEQUENCE: 12

Met Asp Thr Pro Arg Val Leu Leu Ser Ala Val Phe Leu Ile Ser Phe
1               5               10              15

Leu Trp Asp Leu Pro Gly Phe Gln Gln Ala Ser Ile Ser Ser Ser Ser
                20              25              30

Ser Ser Ala Glu Leu Gly Ser Thr Lys Gly Met Arg Ser Arg Lys Glu
            35              40              45

Gly Lys Met Gln Arg Ala Pro Arg Asp Ser Asp Ala Gly Arg Glu Gly
    50              55              60

Gln Glu Pro Gln Pro Arg Pro Gln Asp Glu Pro Arg Ala Gln Gln Pro
65              70              75                  80

Arg Ala Gln Glu Pro Pro Gly Arg Gly Pro Arg Val Val Pro His Glu
                85              90              95

Tyr Met Leu Ser Ile Tyr Arg Thr Tyr Ser Ile Ala Glu Lys Leu Gly
                100             105             110

Ile Asn Ala Ser Phe Phe Gln Ser Ser Lys Ser Ala Asn Thr Ile Thr
            115             120             125

Ser Phe Val Asp Arg Gly Leu Asp Asp Leu Ser His Thr Pro Leu Arg
130             135             140

Arg Gln Lys Tyr Leu Phe Asp Val Ser Met Leu Ser Asp Lys Glu Glu
145                 150             155                 160

Leu Val Gly Ala Glu Leu Arg Leu Phe Arg Gln Ala Pro Ser Ala Pro
                165             170             175

Trp Gly Pro Pro Ala Gly Pro Leu His Val Gln Leu Phe Pro Cys Leu
                180             185             190

Ser Pro Leu Leu Leu Asp Ala Arg Thr Leu Asp Pro Gln Gly Ala Pro
                195             200             205
```

-continued

Pro Ala Gly Trp Glu Val Phe Asp Val Trp Gln Gly Leu Arg His Gln
    210                 215                 220

Pro Trp Lys Gln Leu Cys Leu Glu Leu Arg Ala Ala Trp Gly Glu Leu
225                 230                 235                 240

Asp Ala Gly Glu Ala Glu Ala Arg Ala Arg Gly Pro Gln Gln Pro Pro
                245                 250                 255

Pro Pro Asp Leu Arg Ser Leu Gly Phe Gly Arg Arg Val Arg Pro Pro
            260                 265                 270

Gln Glu Arg Ala Leu Leu Val Val Phe Thr Arg Ser Gln Arg Lys Asn
        275                 280                 285

Leu Phe Ala Glu Met Arg Glu Gln Leu Gly Ser Ala Glu Ala Ala Gly
    290                 295                 300

Pro Gly Ala Gly Ala Glu Gly Ser Trp Pro Pro Ser Gly Ala Pro
305                 310                 315                 320

Asp Ala Arg Pro Trp Leu Pro Ser Pro Gly Arg Arg Arg Arg Thr
                325                 330                 335

Ala Phe Ala Ser Arg His Gly Lys Arg His Gly Lys Lys Ser Arg Leu
            340                 345                 350

Arg Cys Ser Lys Lys Pro Leu His Val Asn Phe Lys Glu Leu Gly Trp
        355                 360                 365

Asp Asp Trp Ile Ile Ala Pro Leu Glu Tyr Glu Ala Tyr His Cys Glu
    370                 375                 380

Gly Val Cys Asp Phe Pro Leu Arg Ser His Leu Glu Pro Thr Asn His
385                 390                 395                 400

Ala Ile Ile Gln Thr Leu Met Asn Ser Met Asp Pro Gly Ser Thr Pro
                405                 410                 415

Pro Ser Cys Cys Val Pro Thr Lys Leu Thr Pro Ile Ser Ile Leu Tyr
            420                 425                 430

Ile Asp Ala Gly Asn Asn Val Val Tyr Lys Gln Tyr Glu Asp Met Val
        435                 440                 445

Val Glu Ser Cys Gly Cys Arg
    450                 455

<210> SEQ ID NO 13
<211> LENGTH: 501
<212> TYPE: PRT
<213> ORGANISM: homo sapiens

<400> SEQUENCE: 13

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
                20                  25                  30

Gln Arg Pro Gln Gly Thr Arg Pro Gly Leu Ala Lys Ala Glu Ala Lys
            35                  40                  45

Glu Arg Pro Pro Leu Ala Arg Asn Val Phe Arg Pro Gly Gly His Ser
        50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

```
Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 14
<211> LENGTH: 392
<212> TYPE: PRT
<213> ORGANISM: homo sapiens
```

<400> SEQUENCE: 14

Met Val Leu Leu Ser Ile Leu Arg Ile Leu Phe Leu Cys Glu Leu Val
1               5                   10                  15

Leu Phe Met Glu His Arg Ala Gln Met Ala Glu Gly Gly Gln Ser Ser
            20                  25                  30

Ile Ala Leu Leu Ala Glu Ala Pro Thr Leu Pro Leu Ile Glu Glu Leu
        35                  40                  45

Leu Glu Glu Ser Pro Gly Glu Gln Pro Arg Lys Pro Arg Leu Leu Gly
    50                  55                  60

His Ser Leu Arg Tyr Met Leu Glu Leu Tyr Arg Arg Ser Ala Asp Ser
65                  70                  75                  80

His Gly His Pro Arg Glu Asn Arg Thr Ile Gly Ala Thr Met Val Arg
                85                  90                  95

Leu Val Lys Pro Leu Thr Asn Val Ala Arg Pro His Arg Gly Thr Trp
            100                 105                 110

His Ile Gln Ile Leu Gly Phe Pro Leu Arg Pro Asn Arg Gly Leu Tyr
        115                 120                 125

Gln Leu Val Arg Ala Thr Val Val Tyr Arg His His Leu Gln Leu Thr
    130                 135                 140

Arg Phe Asn Leu Ser Cys His Val Glu Pro Trp Val Gln Lys Asn Pro
145                 150                 155                 160

Thr Asn His Phe Pro Ser Ser Glu Gly Asp Ser Ser Lys Pro Ser Leu
                165                 170                 175

Met Ser Asn Ala Trp Lys Glu Met Asp Ile Thr Gln Leu Val Gln Gln
            180                 185                 190

Arg Phe Trp Asn Asn Lys Gly His Arg Ile Leu Arg Leu Arg Phe Met
    195                 200                 205

Cys Gln Gln Gln Lys Asp Ser Gly Gly Leu Glu Leu Trp His Gly Thr
210                 215                 220

Ser Ser Leu Asp Ile Ala Phe Leu Leu Leu Tyr Phe Asn Asp Thr His
225                 230                 235                 240

Lys Ser Ile Arg Lys Ala Lys Phe Leu Pro Arg Gly Met Glu Glu Phe
                245                 250                 255

Met Glu Arg Glu Ser Leu Leu Arg Arg Thr Arg Gln Ala Asp Gly Ile
            260                 265                 270

Ser Ala Glu Val Thr Ala Ser Ser Lys His Ser Gly Pro Glu Asn
    275                 280                 285

Asn Gln Cys Ser Leu His Pro Phe Gln Ile Ser Phe Arg Gln Leu Gly
290                 295                 300

Trp Asp His Trp Ile Ile Ala Pro Pro Phe Tyr Thr Pro Asn Tyr Cys
305                 310                 315                 320

Lys Gly Thr Cys Leu Arg Val Leu Arg Asp Gly Leu Asn Ser Pro Asn
                325                 330                 335

His Ala Ile Ile Gln Asn Leu Ile Asn Gln Leu Val Asp Gln Ser Val
            340                 345                 350

Pro Arg Pro Ser Cys Val Pro Tyr Lys Tyr Val Pro Ile Ser Val Leu
    355                 360                 365

Met Ile Glu Ala Asn Gly Ser Ile Leu Tyr Lys Glu Tyr Glu Gly Met
370                 375                 380

Ile Ala Glu Ser Cys Thr Cys Arg
385                 390

<210> SEQ ID NO 15

```
<211> LENGTH: 280
<212> TYPE: PRT
<213> ORGANISM: homo sapiens

<400> SEQUENCE: 15

Val Asp Gly Gln Asn Trp Thr Phe Ala Phe Asp Phe Ser Phe Leu Ser
1               5                   10                  15

Gln Gln Glu Asp Leu Ala Trp Ala Glu Leu Arg Leu Gln Leu Ser Ser
            20                  25                  30

Pro Val Asp Leu Pro Thr Glu Gly Ser Leu Ala Ile Glu Ile Phe His
        35                  40                  45

Gln Pro Lys Pro Asp Thr Glu Gln Ala Ser Asp Ser Cys Leu Glu Arg
    50                  55                  60

Phe Gln Met Asp Leu Phe Thr Val Thr Leu Ser Gln Val Thr Phe Ser
65                  70                  75                  80

Leu Gly Ser Met Val Leu Glu Val Thr Arg Pro Leu Ser Lys Trp Leu
                85                  90                  95

Lys Arg Pro Gly Ala Leu Glu Lys Gln Met Ser Arg Val Ala Gly Glu
            100                 105                 110

Cys Trp Pro Arg Pro Thr Pro Ala Thr Asn Val Leu Leu Met
        115                 120                 125

Leu Tyr Ser Asn Leu Ser Gln Glu Gln Arg Gln Leu Gly Gly Ser Thr
    130                 135                 140

Leu Leu Trp Glu Ala Glu Ser Ser Trp Arg Ala Gln Glu Gly Gln Leu
145                 150                 155                 160

Ser Trp Glu Trp Gly Lys Arg His Arg His His Leu Pro Asp Arg
                165                 170                 175

Ser Gln Leu Cys Arg Lys Val Lys Phe Gln Val Asp Phe Asn Leu Ile
            180                 185                 190

Gly Trp Gly Ser Trp Ile Ile Tyr Pro Lys Gln Tyr Asn Ala Tyr Arg
        195                 200                 205

Cys Glu Gly Glu Cys Pro Asn Pro Val Gly Glu Phe His Pro Thr
    210                 215                 220

Asn His Ala Tyr Ile Gln Ser Leu Leu Lys Arg Tyr Gln Pro His Arg
225                 230                 235                 240

Val Pro Ser Thr Cys Cys Ala Pro Val Lys Thr Lys Pro Leu Ser Met
                245                 250                 255

Leu Tyr Val Asp Asn Gly Arg Val Leu Asp His His Lys Asp Met
            260                 265                 270

Ile Val Glu Glu Cys Gly Cys Leu
        275                 280

<210> SEQ ID NO 16
<211> LENGTH: 103
<212> TYPE: PRT
<213> ORGANISM: homo sapiens

<400> SEQUENCE: 16

Ser Ser Cys Lys Arg His Pro Leu Tyr Val Asp Phe Ser Asp Val Gly
1               5                   10                  15

Trp Asn Asp Trp Ile Val Ala Pro Pro Gly Tyr His Ala Phe Tyr Cys
            20                  25                  30

His Gly Glu Cys Pro Phe Pro Leu Ala Asp His Leu Asn Ser Thr Asn
        35                  40                  45

His Ala Ile Val Gln Thr Leu Val Asn Ser Val Asn Ser Lys Ile Pro
    50                  55                  60
```

-continued

```
Lys Ala Cys Cys Val Pro Thr Glu Leu Ser Ala Ile Ser Met Leu Tyr
65                  70                  75                  80

Leu Asp Glu Asn Glu Lys Val Val Leu Lys Asn Tyr Gln Asp Met Val
                85                  90                  95

Val Glu Gly Cys Gly Cys Arg
            100

<210> SEQ ID NO 17
<211> LENGTH: 107
<212> TYPE: PRT
<213> ORGANISM: homo sapiens

<400> SEQUENCE: 17

Lys Arg Leu Lys Ser Ser Cys Lys Arg His Pro Leu Tyr Val Asp Phe
1               5                   10                  15

Ser Asp Val Gly Trp Asn Asp Trp Ile Val Ala Pro Pro Gly Tyr His
                20                  25                  30

Ala Phe Tyr Cys His Gly Glu Cys Pro Phe Pro Leu Ala Asp His Leu
            35                  40                  45

Asn Ser Thr Asn His Ala Ile Val Gln Thr Leu Val Asn Ser Val Asn
50                  55                  60

Ser Lys Ile Pro Lys Ala Cys Cys Val Pro Thr Glu Leu Ser Ala Ile
65                  70                  75                  80

Ser Met Leu Tyr Leu Asp Glu Asn Glu Lys Val Val Leu Lys Asn Tyr
                85                  90                  95

Gln Asp Met Val Val Glu Gly Cys Gly Cys Arg
            100                 105

<210> SEQ ID NO 18
<211> LENGTH: 105
<212> TYPE: PRT
<213> ORGANISM: homo sapiens

<400> SEQUENCE: 18

Leu Lys Ser Ser Cys Lys Arg His Pro Leu Tyr Val Asp Phe Ser Asp
1               5                   10                  15

Val Gly Trp Asn Asp Trp Ile Val Ala Pro Pro Gly Tyr His Ala Phe
                20                  25                  30

Tyr Cys His Gly Glu Cys Pro Phe Pro Leu Ala Asp His Leu Asn Ser
            35                  40                  45

Thr Asn His Ala Ile Val Gln Thr Leu Val Asn Ser Val Asn Ser Lys
50                  55                  60

Ile Pro Lys Ala Cys Cys Val Pro Thr Glu Leu Ser Ala Ile Ser Met
65                  70                  75                  80

Leu Tyr Leu Asp Glu Asn Glu Lys Val Val Leu Lys Asn Tyr Gln Asp
                85                  90                  95

Met Val Val Glu Gly Cys Gly Cys Arg
            100                 105

<210> SEQ ID NO 19
<211> LENGTH: 106
<212> TYPE: PRT
<213> ORGANISM: homo sapiens

<400> SEQUENCE: 19

Lys Lys Asn Lys Asn Cys Arg Arg His Ser Leu Tyr Val Asp Phe Ser
1               5                   10                  15
```

```
Asp Val Gly Trp Asn Asp Trp Ile Val Ala Pro Pro Gly Tyr Gln Ala
            20                  25                  30

Phe Tyr Cys His Gly Asp Cys Pro Phe Pro Leu Ala Asp His Leu Asn
        35                  40                  45

Ser Thr Asn His Ala Ile Val Gln Thr Leu Val Asn Ser Val Asn Ser
50                  55                  60

Ser Ile Pro Lys Ala Cys Cys Val Pro Thr Glu Leu Ser Ala Ile Ser
65                  70                  75                  80

Met Leu Tyr Leu Asp Glu Tyr Asp Lys Val Val Leu Lys Asn Tyr Gln
                85                  90                  95

Glu Met Val Val Glu Gly Cys Gly Cys Arg
                100                 105
```

<210> SEQ ID NO 20
<211> LENGTH: 115
<212> TYPE: PRT
<213> ORGANISM: homo sapiens

<400> SEQUENCE: 20

```
Ser Val Gly Asp Tyr Asn Thr Ser Glu Gln Lys Gln Ala Cys Lys Lys
1               5                   10                  15

His Glu Leu Tyr Val Ser Phe Arg Asp Leu Gly Trp Gln Asp Trp Ile
                20                  25                  30

Ile Ala Pro Glu Gly Tyr Ala Ala Phe Tyr Cys Asp Gly Glu Cys Ser
                35                  40                  45

Phe Pro Leu Asn Ala His Met Asn Ala Thr Asn His Ala Ile Val Gln
            50                  55                  60

Thr Leu Val His Leu Met Phe Pro Asp His Val Pro Lys Pro Cys Cys
65                  70                  75                  80

Ala Pro Thr Lys Leu Asn Ala Ile Ser Val Leu Tyr Phe Asp Asp Ser
                85                  90                  95

Ser Asn Val Ile Leu Lys Lys Tyr Arg Asn Met Val Val Arg Ser Cys
                100                 105                 110

Gly Cys His
        115
```

<210> SEQ ID NO 21
<211> LENGTH: 111
<212> TYPE: PRT
<213> ORGANISM: homo sapiens

<400> SEQUENCE: 21

```
Tyr Asn Thr Ser Glu Gln Lys Gln Ala Cys Lys Lys His Glu Leu Tyr
1               5                   10                  15

Val Ser Phe Arg Asp Leu Gly Trp Gln Asp Trp Ile Ile Ala Pro Glu
                20                  25                  30

Gly Tyr Ala Ala Phe Tyr Cys Asp Gly Glu Cys Ser Phe Pro Leu Asn
            35                  40                  45

Ala His Met Asn Ala Thr Asn His Ala Ile Val Gln Thr Leu Val His
        50                  55                  60

Leu Met Phe Pro Asp His Val Pro Lys Pro Cys Cys Ala Pro Thr Lys
65                  70                  75                  80

Leu Asn Ala Ile Ser Val Leu Tyr Phe Asp Asp Ser Ser Asn Val Ile
                85                  90                  95

Leu Lys Lys Tyr Arg Asn Met Val Val Arg Ser Cys Gly Cys His
                100                 105                 110
```

<210> SEQ ID NO 22
<211> LENGTH: 109
<212> TYPE: PRT
<213> ORGANISM: homo sapiens

<400> SEQUENCE: 22

Thr Ser Glu Gln Lys Gln Ala Cys Lys Lys His Glu Leu Tyr Val Ser
1               5                   10                  15

Phe Arg Asp Leu Gly Trp Gln Asp Trp Ile Ile Ala Pro Glu Gly Tyr
            20                  25                  30

Ala Ala Phe Tyr Cys Asp Gly Glu Cys Ser Phe Pro Leu Asn Ala His
        35                  40                  45

Met Asn Ala Thr Asn His Ala Ile Val Gln Thr Leu Val His Leu Met
    50                  55                  60

Phe Pro Asp His Val Pro Lys Pro Cys Cys Ala Pro Thr Lys Leu Asn
65                  70                  75                  80

Ala Ile Ser Val Leu Tyr Phe Asp Asp Ser Ser Asn Val Ile Leu Lys
                85                  90                  95

Lys Tyr Arg Asn Met Val Val Arg Ser Cys Gly Cys His
            100                 105

<210> SEQ ID NO 23
<211> LENGTH: 112
<212> TYPE: PRT
<213> ORGANISM: homo sapien

<400> SEQUENCE: 23

Asp Tyr Asn Thr Ser Glu Gln Lys Gln Ala Cys Lys Lys His Glu Leu
1               5                   10                  15

Tyr Val Ser Phe Arg Asp Leu Gly Trp Gln Asp Trp Ile Ile Ala Pro
            20                  25                  30

Glu Gly Tyr Ala Ala Phe Tyr Cys Asp Gly Glu Cys Ser Phe Pro Leu
        35                  40                  45

Asn Ala His Met Asn Ala Thr Asn His Ala Ile Val Gln Thr Leu Val
    50                  55                  60

His Leu Met Phe Pro Asp His Val Pro Lys Pro Cys Cys Ala Pro Thr
65                  70                  75                  80

Lys Leu Asn Ala Ile Ser Val Leu Tyr Phe Asp Asp Ser Ser Asn Val
                85                  90                  95

Ile Leu Lys Lys Tyr Arg Asn Met Val Val Arg Ser Cys Gly Cys His
            100                 105                 110

<210> SEQ ID NO 24
<211> LENGTH: 117
<212> TYPE: PRT
<213> ORGANISM: homo sapien

<400> SEQUENCE: 24

Met Ser Ser Val Gly Asp Tyr Asn Thr Ser Glu Gln Lys Gln Ala Cys
1               5                   10                  15

Lys Lys His Glu Leu Tyr Val Ser Phe Arg Asp Leu Gly Trp Gln Asp
            20                  25                  30

Trp Ile Ile Ala Pro Glu Gly Tyr Ala Ala Phe Tyr Cys Asp Gly Glu
        35                  40                  45

Cys Ser Phe Pro Leu Asn Ala His Met Asn Ala Thr Asn His Ala Ile
    50                  55                  60

Val Gln Thr Leu Val His Leu Met Phe Pro Asp His Val Pro Lys Pro

```
                65                  70                  75                  80
Cys Cys Ala Pro Thr Lys Leu Asn Ala Ile Ser Val Leu Tyr Phe Asp
                    85                  90                  95

Asp Ser Ser Asn Val Ile Leu Lys Lys Tyr Arg Asn Met Val Val Arg
                100                 105                 110

Ser Cys Gly Cys His
        115

<210> SEQ ID NO 25
<211> LENGTH: 114
<212> TYPE: PRT
<213> ORGANISM: homo sapien

<400> SEQUENCE: 25

Val Gly Asp Tyr Asn Thr Ser Glu Gln Lys Gln Ala Cys Lys Lys His
1               5                   10                  15

Glu Leu Tyr Val Ser Phe Arg Asp Leu Gly Trp Gln Asp Trp Ile Ile
            20                  25                  30

Ala Pro Glu Gly Tyr Ala Ala Phe Tyr Cys Asp Gly Glu Cys Ser Phe
        35                  40                  45

Pro Leu Asn Ala His Met Asn Ala Thr Asn His Ala Ile Val Gln Thr
    50                  55                  60

Leu Val His Leu Met Phe Pro Asp His Val Pro Lys Pro Cys Cys Ala
65                  70                  75                  80

Pro Thr Lys Leu Asn Ala Ile Ser Val Leu Tyr Phe Asp Asp Ser Ser
                85                  90                  95

Asn Val Ile Leu Lys Lys Tyr Arg Asn Met Val Val Arg Ser Cys Gly
                100                 105                 110

Cys His

<210> SEQ ID NO 26
<211> LENGTH: 104
<212> TYPE: PRT
<213> ORGANISM: homo sapien

<400> SEQUENCE: 26

Gln Ala Cys Lys Lys His Glu Leu Tyr Val Ser Phe Arg Asp Leu Gly
1               5                   10                  15

Trp Gln Asp Trp Ile Ile Ala Pro Glu Gly Tyr Ala Ala Phe Tyr Cys
            20                  25                  30

Asp Gly Glu Cys Ser Phe Pro Leu Asn Ala His Met Asn Ala Thr Asn
        35                  40                  45

His Ala Ile Val Gln Thr Leu Val His Leu Met Phe Pro Asp His Val
    50                  55                  60

Pro Lys Pro Cys Cys Ala Pro Thr Lys Leu Asn Ala Ile Ser Val Leu
65                  70                  75                  80

Tyr Phe Asp Asp Ser Ser Asn Val Ile Leu Lys Lys Tyr Arg Asn Met
                85                  90                  95

Val Val Arg Ser Cys Gly Cys His
            100

<210> SEQ ID NO 27
<211> LENGTH: 107
<212> TYPE: PRT
<213> ORGANISM: homo sapien

<400> SEQUENCE: 27
```

Glu Gln Lys Gln Ala Cys Lys Lys His Glu Leu Tyr Val Ser Phe Arg
1               5                   10                  15

Asp Leu Gly Trp Gln Asp Trp Ile Ile Ala Pro Glu Gly Tyr Ala Ala
            20                  25                  30

Phe Tyr Cys Asp Gly Glu Cys Ser Phe Pro Leu Asn Ala His Met Asn
        35                  40                  45

Ala Thr Asn His Ala Ile Val Gln Thr Leu Val His Leu Met Phe Pro
    50                  55                  60

Asp His Val Pro Lys Pro Cys Cys Ala Pro Thr Lys Leu Asn Ala Ile
65                  70                  75                  80

Ser Val Leu Tyr Phe Asp Asp Ser Ser Asn Val Ile Leu Lys Lys Tyr
                85                  90                  95

Arg Asn Met Val Val Arg Ser Cys Gly Cys His
            100                 105

<210> SEQ ID NO 28
<211> LENGTH: 108
<212> TYPE: PRT
<213> ORGANISM: homo sapien

<400> SEQUENCE: 28

Ser Glu Gln Lys Gln Ala Cys Lys Lys His Glu Leu Tyr Val Ser Phe
1               5                   10                  15

Arg Asp Leu Gly Trp Gln Asp Trp Ile Ile Ala Pro Glu Gly Tyr Ala
            20                  25                  30

Ala Phe Tyr Cys Asp Gly Glu Cys Ser Phe Pro Leu Asn Ala His Met
        35                  40                  45

Asn Ala Thr Asn His Ala Ile Val Gln Thr Leu Val His Leu Met Phe
    50                  55                  60

Pro Asp His Val Pro Lys Pro Cys Cys Ala Pro Thr Lys Leu Asn Ala
65                  70                  75                  80

Ile Ser Val Leu Tyr Phe Asp Asp Ser Ser Asn Val Ile Leu Lys Lys
                85                  90                  95

Tyr Arg Asn Met Val Val Arg Ser Cys Gly Cys His
            100                 105

<210> SEQ ID NO 29
<211> LENGTH: 117
<212> TYPE: PRT
<213> ORGANISM: homo sapiens

<400> SEQUENCE: 29

Val Ser Ser Ala Ser Asp Tyr Asn Ser Ser Glu Leu Lys Thr Ala Cys
1               5                   10                  15

Arg Lys His Glu Leu Tyr Val Ser Phe Gln Asp Leu Gly Trp Gln Asp
            20                  25                  30

Trp Ile Ile Ala Pro Lys Gly Tyr Ala Ala Asn Tyr Cys Asp Gly Glu
        35                  40                  45

Cys Ser Phe Pro Leu Asn Ala His Met Asn Ala Thr Asn His Ala Ile
    50                  55                  60

Val Gln Thr Leu Val His Leu Met Asn Pro Glu Tyr Val Pro Lys Pro
65                  70                  75                  80

Cys Cys Ala Pro Thr Lys Leu Asn Ala Ile Ser Val Leu Tyr Phe Asp
                85                  90                  95

Asp Asn Ser Asn Val Ile Leu Lys Lys Tyr Arg Asn Met Val Val Arg
            100                 105                 110

-continued

Ala Cys Gly Cys His
        115

<210> SEQ ID NO 30
<211> LENGTH: 104
<212> TYPE: PRT
<213> ORGANISM: homo sapiens

<400> SEQUENCE: 30

Gln Ala Cys Lys Lys His Glu Leu Tyr Val Ser Phe Arg Asp Leu Gly
1               5                   10                  15

Trp Gln Asp Trp Ile Ile Ala Pro Glu Gly Tyr Ala Ala Tyr Tyr Cys
            20                  25                  30

Glu Gly Glu Cys Ala Phe Pro Leu Asn Ser Tyr Met Asn Ala Thr Asn
        35                  40                  45

His Ala Ile Val Gln Thr Leu Val His Phe Ile Asn Pro Glu Thr Val
    50                  55                  60

Pro Lys Pro Cys Cys Ala Pro Thr Gln Leu Asn Ala Ile Ser Val Leu
65                  70                  75                  80

Tyr Phe Asp Asp Ser Ser Asn Val Ile Leu Lys Lys Tyr Arg Asn Met
                85                  90                  95

Val Val Arg Ala Cys Gly Cys His
            100

<210> SEQ ID NO 31
<211> LENGTH: 112
<212> TYPE: PRT
<213> ORGANISM: homo sapiens

<400> SEQUENCE: 31

Glu Asn Ser Ser Ser Asp Gln Arg Gln Ala Cys Lys Lys His Glu Leu
1               5                   10                  15

Tyr Val Ser Phe Arg Asp Leu Gly Trp Gln Asp Trp Ile Ile Ala Pro
            20                  25                  30

Glu Gly Tyr Ala Ala Tyr Tyr Cys Glu Gly Glu Cys Ala Phe Pro Leu
        35                  40                  45

Asn Ser Tyr Met Asn Ala Thr Asn His Ala Ile Val Gln Thr Leu Val
    50                  55                  60

His Phe Ile Asn Pro Glu Thr Val Pro Lys Pro Cys Cys Ala Pro Thr
65                  70                  75                  80

Gln Leu Asn Ala Ile Ser Val Leu Tyr Phe Asp Asp Ser Ser Asn Val
                85                  90                  95

Ile Leu Lys Lys Tyr Arg Asn Met Val Val Arg Ala Cys Gly Cys His
            100                 105                 110

<210> SEQ ID NO 32
<211> LENGTH: 117
<212> TYPE: PRT
<213> ORGANISM: homo sapiens

<400> SEQUENCE: 32

Met Ala Asn Val Ala Glu Asn Ser Ser Ser Asp Gln Arg Gln Ala Cys
1               5                   10                  15

Lys Lys His Glu Leu Tyr Val Ser Phe Arg Asp Leu Gly Trp Gln Asp
            20                  25                  30

Trp Ile Ile Ala Pro Glu Gly Tyr Ala Ala Tyr Tyr Cys Glu Gly Glu
        35                  40                  45

Cys Ala Phe Pro Leu Asn Ser Tyr Met Asn Ala Thr Asn His Ala Ile

```
              50                  55                  60
Val Gln Thr Leu Val His Phe Ile Asn Pro Glu Thr Val Pro Lys Pro
 65                  70                  75                  80

Cys Cys Ala Pro Thr Gln Leu Asn Ala Ile Ser Val Leu Tyr Phe Asp
                 85                  90                  95

Asp Ser Ser Asn Val Ile Leu Lys Lys Tyr Arg Asn Met Val Val Arg
            100                 105                 110

Ala Cys Gly Cys His
            115

<210> SEQ ID NO 33
<211> LENGTH: 114
<212> TYPE: PRT
<213> ORGANISM: homo sapiens

<400> SEQUENCE: 33

Val Ala Glu Asn Ser Ser Ser Asp Gln Arg Gln Ala Cys Lys Lys His
  1               5                  10                  15

Glu Leu Tyr Val Ser Phe Arg Asp Leu Gly Trp Gln Asp Trp Ile Ile
                 20                  25                  30

Ala Pro Glu Gly Tyr Ala Ala Tyr Tyr Cys Glu Gly Glu Cys Ala Phe
             35                  40                  45

Pro Leu Asn Ser Tyr Met Asn Ala Thr Asn His Ala Ile Val Gln Thr
 50                  55                  60

Leu Val His Phe Ile Asn Pro Glu Thr Val Pro Lys Pro Cys Cys Ala
 65                  70                  75                  80

Pro Thr Gln Leu Asn Ala Ile Ser Val Leu Tyr Phe Asp Asp Ser Ser
                 85                  90                  95

Asn Val Ile Leu Lys Lys Tyr Arg Asn Met Val Val Arg Ala Cys Gly
            100                 105                 110

Cys His

<210> SEQ ID NO 34
<211> LENGTH: 109
<212> TYPE: PRT
<213> ORGANISM: homo sapiens

<400> SEQUENCE: 34

Gly Lys Lys Ser Arg Leu Arg Cys Ser Lys Lys Pro Leu His Val Asn
  1               5                  10                  15

Phe Lys Glu Leu Gly Trp Asp Asp Trp Ile Ile Ala Pro Leu Glu Tyr
                 20                  25                  30

Glu Ala Tyr His Cys Glu Gly Val Cys Asp Phe Pro Leu Arg Ser His
             35                  40                  45

Leu Glu Pro Thr Asn His Ala Ile Ile Gln Thr Leu Met Asn Ser Met
 50                  55                  60

Asp Pro Gly Ser Thr Pro Pro Ser Cys Cys Val Pro Thr Lys Leu Thr
 65                  70                  75                  80

Pro Ile Ser Ile Leu Tyr Ile Asp Ala Gly Asn Asn Val Val Tyr Lys
                 85                  90                  95

Gln Tyr Glu Asp Met Val Val Glu Ser Cys Gly Cys Arg
            100                 105

<210> SEQ ID NO 35
<211> LENGTH: 106
<212> TYPE: PRT
<213> ORGANISM: homo sapiens
```

<400> SEQUENCE: 35

Leu Lys Ala Arg Cys Ser Arg Lys Ala Leu His Val Asn Phe Lys Asp
1               5                   10                  15

Met Gly Trp Asp Asp Trp Ile Ile Ala Pro Leu Glu Tyr Glu Ala Phe
            20                  25                  30

His Cys Glu Gly Leu Cys Glu Phe Pro Leu Arg Ser His Leu Glu Pro
        35                  40                  45

Thr Asn His Ala Val Ile Gln Thr Leu Met Asn Ser Met Asp Pro Glu
    50                  55                  60

Ser Thr Pro Pro Thr Cys Cys Val Pro Thr Arg Leu Ser Pro Ile Ser
65                  70                  75                  80

Ile Leu Phe Ile Asp Ser Ala Asn Asn Val Val Tyr Lys Gln Tyr Glu
                85                  90                  95

Asp Met Val Val Glu Ser Cys Gly Cys Arg
            100                 105

<210> SEQ ID NO 36
<211> LENGTH: 11
<212> TYPE: PRT
<213> ORGANISM: homo sapiens

<400> SEQUENCE: 36

Gln Ala Lys His Lys Gln Arg Lys Arg Leu Lys
1               5                   10

<210> SEQ ID NO 37
<211> LENGTH: 7
<212> TYPE: PRT
<213> ORGANISM: homo sapiens

<400> SEQUENCE: 37

Gln Ala Lys His Lys Gln Arg
1               5

<210> SEQ ID NO 38
<211> LENGTH: 9
<212> TYPE: PRT
<213> ORGANISM: homo sapiens

<400> SEQUENCE: 38

Gln Ala Lys His Lys Gln Arg Lys Arg
1               5

<210> SEQ ID NO 39
<211> LENGTH: 10
<212> TYPE: PRT
<213> ORGANISM: homo sapiens

<400> SEQUENCE: 39

Ser Pro Lys His His Ser Gln Arg Ala Arg
1               5                   10

<210> SEQ ID NO 40
<211> LENGTH: 23
<212> TYPE: PRT
<213> ORGANISM: homo sapiens

<400> SEQUENCE: 40

Ala Ala Asn Lys Arg Lys Asn Gln Asn Arg Asn Lys Ser Ser Ser His
1               5                   10                  15

Gln Asp Ser Ser Arg Met Ser
            20

<210> SEQ ID NO 41
<211> LENGTH: 27
<212> TYPE: PRT
<213> ORGANISM: homo sapiens

<400> SEQUENCE: 41

Ala Ala Asn Lys Arg Lys Asn Gln Asn Arg Asn Lys Ser Ser Ser His
1               5                   10                  15
Gln Asp Ser Ser Arg Met Ser Ser Val Gly Asp
            20                  25

<210> SEQ ID NO 42
<211> LENGTH: 29
<212> TYPE: PRT
<213> ORGANISM: homo sapiens

<400> SEQUENCE: 42

Ala Ala Asn Lys Arg Lys Asn Gln Asn Arg Asn Lys Ser Ser Ser His
1               5                   10                  15
Gln Asp Ser Ser Arg Met Ser Ser Val Gly Asp Tyr Asn
            20                  25

<210> SEQ ID NO 43
<211> LENGTH: 26
<212> TYPE: PRT
<213> ORGANISM: homo sapien

<400> SEQUENCE: 43

Ala Ala Asn Lys Arg Lys Asn Gln Asn Arg Asn Lys Ser Ser Ser His
1               5                   10                  15
Gln Asp Ser Ser Arg Met Ser Ser Val Gly
            20                  25

<210> SEQ ID NO 44
<211> LENGTH: 21
<212> TYPE: PRT
<213> ORGANISM: homo sapien

<400> SEQUENCE: 44

Ala Ala Asn Lys Arg Lys Asn Gln Asn Arg Asn Lys Ser Ser Ser His
1               5                   10                  15
Gln Asp Ser Ser Arg
            20

<210> SEQ ID NO 45
<211> LENGTH: 24
<212> TYPE: PRT
<213> ORGANISM: homo sapien

<400> SEQUENCE: 45

Ala Ala Asn Lys Arg Lys Asn Gln Asn Arg Asn Lys Ser Ser Ser His
1               5                   10                  15
Gln Asp Ser Ser Arg Met Ser Ser
            20

<210> SEQ ID NO 46
<211> LENGTH: 31
<212> TYPE: PRT
<213> ORGANISM: homo sapien

<400> SEQUENCE: 46

Ala Ala Asn Lys Arg Lys Asn Gln Asn Arg Asn Lys Ser Ser Ser His
1               5                   10                  15

Gln Asp Ser Ser Arg Met Ser Ser Val Gly Asp Tyr Asn Thr Ser
            20                  25                  30

<210> SEQ ID NO 47
<211> LENGTH: 34
<212> TYPE: PRT
<213> ORGANISM: homo sapien

<400> SEQUENCE: 47

Ala Ala Asn Lys Arg Lys Asn Gln Asn Arg Asn Lys Ser Ser Ser His
1               5                   10                  15

Gln Asp Ser Ser Arg Met Ser Ser Val Gly Asp Tyr Asn Thr Ser Glu
            20                  25                  30

Gln Lys

<210> SEQ ID NO 48
<211> LENGTH: 30
<212> TYPE: PRT
<213> ORGANISM: homo sapien

<400> SEQUENCE: 48

Ala Ala Asn Lys Arg Lys Asn Gln Asn Arg Asn Lys Ser Ser Ser His
1               5                   10                  15

Gln Asp Ser Ser Arg Met Ser Ser Val Gly Asp Tyr Asn Thr
            20                  25                  30

<210> SEQ ID NO 49
<211> LENGTH: 22
<212> TYPE: PRT
<213> ORGANISM: homo sapiens

<400> SEQUENCE: 49

Ser Ala Ser Ser Arg Arg Arg Gln Gln Ser Arg Asn Arg Ser Thr Gln
1               5                   10                  15

Ser Gln Asp Val Ala Arg
            20

<210> SEQ ID NO 50
<211> LENGTH: 35
<212> TYPE: PRT
<213> ORGANISM: homo sapiens

<400> SEQUENCE: 50

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg
        35

<210> SEQ ID NO 51
<211> LENGTH: 27
<212> TYPE: PRT
<213> ORGANISM: homo sapiens

<400> SEQUENCE: 51

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala
            20                  25

<210> SEQ ID NO 52
<211> LENGTH: 22
<212> TYPE: PRT
<213> ORGANISM: homo sapiens

<400> SEQUENCE: 52

Ser Thr Gly Ser Lys Gln Arg Ser Gln Asn Arg Ser Lys Thr Pro Lys
1               5                   10                  15

Asn Gln Glu Ala Leu Arg
            20

<210> SEQ ID NO 53
<211> LENGTH: 25
<212> TYPE: PRT
<213> ORGANISM: homo sapiens

<400> SEQUENCE: 53

Ser Thr Gly Ser Lys Gln Arg Ser Gln Asn Arg Ser Lys Thr Pro Lys
1               5                   10                  15

Asn Gln Glu Ala Leu Arg Met Ala Asn
            20                  25

<210> SEQ ID NO 54
<211> LENGTH: 11
<212> TYPE: PRT
<213> ORGANISM: homo sapiens

<400> SEQUENCE: 54

Thr Ala Phe Ala Ser Arg His Gly Lys Arg His
1               5                   10

<210> SEQ ID NO 55
<211> LENGTH: 14
<212> TYPE: PRT
<213> ORGANISM: homo sapiens

<400> SEQUENCE: 55

Ala Pro Leu Ala Thr Arg Gln Gly Lys Arg Pro Ser Lys Asn
1               5                   10

<210> SEQ ID NO 56
<211> LENGTH: 36
<212> TYPE: PRT
<213> ORGANISM: artificial
<220> FEATURE:
<223> OTHER INFORMATION: TAT protein

<400> SEQUENCE: 56

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35

<210> SEQ ID NO 57
<211> LENGTH: 10
<212> TYPE: PRT
<213> ORGANISM: artificial
<220> FEATURE:

<223> OTHER INFORMATION: TAT protein

<400> SEQUENCE: 57

Gly Arg Lys Lys Arg Arg Gln Arg Arg Arg
1               5                   10

<210> SEQ ID NO 58
<211> LENGTH: 309
<212> TYPE: DNA
<213> ORGANISM: artificial
<220> FEATURE:
<223> OTHER INFORMATION: nucleic acid sequence for truncated BMP

<400> SEQUENCE: 58

```
agcagctgca aacgccatcc gctgtatgtg gattttagcg atgtgggctg gaacgattgg    60
attgtggcgc cgccgggcta tcatgcgttt tattgccatg gcgaatgccc gtttccgctg   120
gcggatcatc tgaacagcac caaccatgcg attgtgcaga ccctggtgaa cagcgtgaac   180
agcaaaattc cgaaagcgtg ctgcgtgccg accgaactga gcgcgattag catgctgtat   240
ctggatgaaa acgaaaaagt ggtgctgaaa aactatcagg atatggtggt ggaaggctgc   300
ggctgccgc                                                           309
```

<210> SEQ ID NO 59
<211> LENGTH: 321
<212> TYPE: DNA
<213> ORGANISM: artificial
<220> FEATURE:
<223> OTHER INFORMATION: nucleic acid sequence for truncated BMP

<400> SEQUENCE: 59

```
aaacgcctga aaagcagctg caaacgccat ccgctgtatg tggattttag cgatgtgggc    60
tggaacgatt ggattgtggc gccgccgggc tatcatgcgt tttattgcca tggcgaatgc   120
ccgtttccgc tggcggatca tctgaacagc accaaccatg cgattgtgca gaccctggtg   180
aacagcgtga acagcaaaat tccgaaagcg tgctgcgtgc cgaccgaact gagcgcgatt   240
agcatgctgt atctggatga aaacgaaaaa gtggtgctga aaaactatca ggatatggtg   300
gtggaaggct gcggctgccg c                                             321
```

<210> SEQ ID NO 60
<211> LENGTH: 315
<212> TYPE: DNA
<213> ORGANISM: artificial
<220> FEATURE:
<223> OTHER INFORMATION: nucleic acid for truncated BMP

<400> SEQUENCE: 60

```
ctgaaaagca gctgcaaacg ccatccgctg tatgtggatt ttagcgatgt gggctggaac    60
gattggattg tggcgccgcc gggctatcat gcgttttatt gccatggcga atgccgttt   120
ccgctggcgg atcatctgaa cagcaccaac catgcgattg tgcagaccct ggtgaacagc   180
gtgaacagca aaattccgaa agcgtgctgc gtgccgaccg aactgagcgc gattagcatg   240
ctgtatctgg atgaaaacga aaaagtggtg ctgaaaaact atcaggatat ggtggtggaa   300
ggctgcggct gccgc                                                    315
```

<210> SEQ ID NO 61
<211> LENGTH: 318
<212> TYPE: DNA
<213> ORGANISM: artificial
<220> FEATURE:

<223> OTHER INFORMATION: nucleic acid sequence for truncated BMP

<400> SEQUENCE: 61

```
aaaaaaaaca aaaactgccg ccgccatagc ctgtatgtgg attttagcga tgtgggctgg      60
aacgattgga ttgtggcgcc gccgggctat caggcgtttt attgccatgg cgattgcccg     120
tttccgctgg cggatcatct gaacagcacc aaccatgcga ttgtgcagac cctggtgaac     180
agcgtgaaca gcagcattcc gaaagcgtgc tgcgtgccga ccgaactgag cgcgattagc     240
atgctgtatc tggatgaata tgataaagtg gtgctgaaaa actatcagga aatggtggtg     300
gaaggctgcg gctgccgc                                                    318
```

<210> SEQ ID NO 62
<211> LENGTH: 345
<212> TYPE: DNA
<213> ORGANISM: artificial
<220> FEATURE:
<223> OTHER INFORMATION: nucleic acid sequence for truncated BMP

<400> SEQUENCE: 62

```
agcgtgggcg attataacac cagcgaacag aaacaggcgt gcaaaaaaca tgaactgtat      60
gtgagctttc gcgatctggg ctggcaggat tggattattg cgccggaagg ctatgcggcg     120
ttttattgcg atggcgaatg cagctttccg ctgaacgcgc atatgaacgc gaccaaccat     180
gcgattgtgc agaccctggt gcatctgatg tttccggatc atgtgccgaa accgtgctgc     240
gcgccgacca aactgaacgc gattagcgtg ctgtattttg atgatagcag caacgtgatt     300
ctgaaaaaat atcgcaacat ggtggtgcgc agctgcggct gccat                      345
```

<210> SEQ ID NO 63
<211> LENGTH: 333
<212> TYPE: DNA
<213> ORGANISM: artificial
<220> FEATURE:
<223> OTHER INFORMATION: nucleic acid sequence for truncated BMP

<400> SEQUENCE: 63

```
tataacacca gcgaacagaa acaggcgtgc aaaaaacatg aactgtatgt gagctttcgc      60
gatctgggct ggcaggattg gattattgcg ccggaaggct atgcggcgtt ttattgcgat     120
ggcgaatgca gctttccgct gaacgcgcat atgaacgcga ccaaccatgc gattgtgcag     180
accctggtgc atctgatgtt tccggatcat gtgccgaaac cgtgctgcgc gccgaccaaa     240
ctgaacgcga ttagcgtgct gtattttgat gatagcagca acgtgattct gaaaaaatat     300
cgcaacatgg tggtgcgcag ctgcggctgc cat                                    333
```

<210> SEQ ID NO 64
<211> LENGTH: 327
<212> TYPE: DNA
<213> ORGANISM: artificial
<220> FEATURE:
<223> OTHER INFORMATION: nucleic acid sequence for truncated BMP

<400> SEQUENCE: 64

```
accagcgaac agaaacaggc gtgcaaaaaa catgaactgt atgtgagctt tcgcgatctg      60
ggctggcagg attggattat tgcgccggaa ggctatgcgg cgttttattg cgatggcgaa     120
tgcagctttc cgctgaacgc gcatatgaac gcgaccaacc atgcgattgt gcagaccctg     180
gtgcatctga tgtttccgga tcatgtgccg aaaccgtgct gcgcgccgac caaactgaac     240
gcgattagcg tgctgtattt tgatgatagc agcaacgtga ttctgaaaaa atatcgcaac     300
```

```
atggtggtgc gcagctgcgg ctgccat                                          327

<210> SEQ ID NO 65
<211> LENGTH: 336
<212> TYPE: DNA
<213> ORGANISM: artificial
<220> FEATURE:
<223> OTHER INFORMATION: nucleic acid sequence for truncated BMP

<400> SEQUENCE: 65
gattataaca ccagcgaaca gaaacaggcg tgcaaaaaac atgaactgta tgtgagcttt      60
cgcgatctgg gctggcagga ttggattatt gcgccggaag ctatgcggc gttttattgc      120 gatggcgaat gcagctttcc gctgaacgcg catatgaacg cgaccaacca tgcgattgtg     180
cagaccctgg tgcatctgat gtttccggat catgtgccga accgtgctg cgcgccgacc      240 aaactgaacg cgattagcgt gctgtatttt gatgatagca gcaacgtgat tctgaaaaaa     300
tatcgcaaca tggtggtgcg cagctgcggc tgccat                               336

<210> SEQ ID NO 66
<211> LENGTH: 351
<212> TYPE: DNA
<213> ORGANISM: artificial
<220> FEATURE:
<223> OTHER INFORMATION: nucleic acid sequence for truncated BMP

<400> SEQUENCE: 66
atgagcagcg tgggcgatta taacaccagc gaacagaaac aggcgtgcaa aaaacatgaa      60
ctgtatgtga gctttcgcga tctgggctgg caggattgga ttattgcgcc ggaaggctat     120
gcggcgtttt attgcgatgg cgaatgcagc tttccgctga acgcgcatat gaacgcgacc     180
aaccatgcga ttgtgcagac cctggtgcat ctgatgtttc cggatcatgt gccgaaaccg     240
tgctgcgcgc cgaccaaact gaacgcgatt agcgtgctgt attttgatga tagcagcaac     300
gtgattctga aaaatatcg caacatggtg gtgcgcagct gcggctgcca t               351

<210> SEQ ID NO 67
<211> LENGTH: 342
<212> TYPE: DNA
<213> ORGANISM: artificial
<220> FEATURE:
<223> OTHER INFORMATION: nucleic acid sequence for truncated BMP

<400> SEQUENCE: 67
gtgggcgatt ataacaccag cgaacagaaa caggcgtgca aaaacatga actgtatgtg       60 agctttcgcg atctgggctg gcaggattgg attattgcgc cggaaggcta tgcggcgttt    120
tattgcgatg gcgaatgcag ctttccgctg aacgcgcata tgaacgcgac caaccatgcg    180
attgtgcaga ccctggtgca tctgatgttt ccggatcatg tgccgaaacc gtgctgcgcg    240
ccgaccaaac tgaacgcgat tagcgtgctg tattttgatg atagcagcaa cgtgattctg    300 aaaaatatc gcaacatggt ggtgcgcagc tgcggctgcc at                        342

<210> SEQ ID NO 68
<211> LENGTH: 393
<212> TYPE: DNA
<213> ORGANISM: artificial
<220> FEATURE:
<223> OTHER INFORMATION: nucleic acid sequence for truncated BMP

<400> SEQUENCE: 68
```

```
gaacagaaac aggcgtgcaa aaaacatgaa ctgtatgtga gctttcgcga tctgggctgg      60
caggattgga ttattgcgcc ggaaggctat gcggcgtttt attgcgatgg cgaatgcagc     120
tttccgctga acgcgcatat gaacgcgacc aaccatgcga ttgtgcagac cctggtgcat    180
ctgatgtttc cggatcatgt gccgaaaccg tgctgcgcgc cgaccaaact gaacgcgatt    240
agcgtgctgt attttgatga tagcagcaac gtgattctga aaaaatatcg caacatggtg    300
gtgcgcagct gcggctgcca ttattttgat gatagcagca cgtgattct gaaaaaatat    360 cgcaacatgg tggtgcgcag ctgcggctgc cat                                  393

<210> SEQ ID NO 69
<211> LENGTH: 312
<212> TYPE: DNA
<213> ORGANISM: artificial
<220> FEATURE:
<223> OTHER INFORMATION: nucleic acid sequence for truncated BMP

<400> SEQUENCE: 69
caggcgtgca aaaacatga actgtatgtg agctttcgcg atctgggctg gcaggattgg      60
attattgcgc cggaaggcta tgcggcgttt tattgcgatg gcgaatgcag ctttccgctg    120
aacgcgcata tgaacgcgac caaccatgcg attgtgcaga ccctggtgca tctgatgttt    180
ccggatcatg tgccgaaacc gtgctgcgcg ccgaccaaac tgaacgcgat tagcgtgctg    240
tattttgatg atagcagcaa cgtgattctg aaaaaatatc gcaacatggt ggtgcgcagc    300
tgcggctgcc at                                                         312

<210> SEQ ID NO 70
<211> LENGTH: 66
<212> TYPE: DNA
<213> ORGANISM: artificial
<220> FEATURE:
<223> OTHER INFORMATION: nucleic acid sequence for truncated BMP

<400> SEQUENCE: 70
agcgcgagca gccgccgccg ccagcagagc cgcaaccgca gcacccagag ccaggatgtg      60
gcgcgc                                                                 66

<210> SEQ ID NO 71
<211> LENGTH: 324
<212> TYPE: DNA
<213> ORGANISM: artificial
<220> FEATURE:
<223> OTHER INFORMATION: nucleic acid sequence for truncated BMP

<400> SEQUENCE: 71
agcgaacaga acaggcgtg caaaaaacat gaactgtatg tgagctttcg cgatctgggc      60
tggcaggatt ggattattgc gccggaaggc tatgcggcgt tttattgcga tggcgaatgc    120
agctttccgc tgaacgcgca tatgaacgcg accaaccatg cgattgtgca gaccctggtg    180
catctgatgt ttccggatca tgtgccgaaa ccgtgctgcg cgccgaccaa actgaacgcg    240
attagcgtgc tgtattttga tgatagcagc aacgtgattc tgaaaaaata tcgcaacatg    300
gtggtgcgca gctgcggctg ccat                                            324

<210> SEQ ID NO 72
<211> LENGTH: 312
<212> TYPE: DNA
<213> ORGANISM: artificial
<220> FEATURE:
<223> OTHER INFORMATION: nucleic acid sequence for truncated BMP
```

<400> SEQUENCE: 72

```
caggcgtgca aaaaacatga actgtatgtg agctttcgcg atctgggctg gcaggattgg      60
attattgcgc cggaaggcta tgcggcgtat tattgcgaag gcaatgcgc gtttccgctg      120
aacagctata tgaacgcgac caaccatgcg attgtgcaga ccctggtgca ttttattaac     180
ccggaaaccg tgccgaaacc gtgctgcgcg ccgacccagc tgaacgcgat tagcgtgctg     240
tatttgatg atagcagcaa cgtgattctg aaaaatatc gcaacatggt ggtgcgcgcg      300
tgcggctgcc at                                                        312
```

<210> SEQ ID NO 73
<211> LENGTH: 336
<212> TYPE: DNA
<213> ORGANISM: artificial
<220> FEATURE:
<223> OTHER INFORMATION: nucleic acid sequence for truncated BMP

<400> SEQUENCE: 73

```
gaaaacagca gcagcgatca gcgccaggcg tgcaaaaaac atgaactgta tgtgagcttt     60
cgcgatctgg gctggcagga ttggattatt gcgccggaag gctatgcggc gtattattgc    120
gaaggcgaat gcgcgtttcc gctgaacagc tatatgaacg cgaccaacca tgcgattgtg    180
cagacccctgg tgcattttat aacccggaa accgtgccga aaccgtgctg cgcgccgacc    240
cagctgaacg cgattagcgt gctgtatttt gatgatagca gcaacgtgat tctgaaaaaa    300
tatcgcaaca tggtggtgcg cgcgtgcggc tgccat                              336
```

<210> SEQ ID NO 74
<211> LENGTH: 351
<212> TYPE: DNA
<213> ORGANISM: artificial
<220> FEATURE:
<223> OTHER INFORMATION: nucleic acid sequence for truncated BMP

<400> SEQUENCE: 74

```
atggcgaacg tggcggaaaa cagcagcagc gatcagcgcc aggcgtgcaa aaaacatgaa     60
ctgtatgtga gctttcgcga tctgggctgg caggattgga ttattgcgcc ggaaggctat    120
gcggcgtatt attgcgaagg cgaatgcgcg tttccgctga acagctatat gaacgcgacc    180
aaccatgcga ttgtgcagac cctggtgcat tttattaacc cggaaaccgt gccgaaaccg    240
tgctgcgcgc cgacccagct gaacgcgatt agcgtgctgt attttgatga tagcagcaac    300
gtgattctga aaaatatcg caacatggtg gtgcgcgcgt gcggctgcca t              351
```

<210> SEQ ID NO 75
<211> LENGTH: 342
<212> TYPE: DNA
<213> ORGANISM: artificial
<220> FEATURE:
<223> OTHER INFORMATION: nucleic acid sequence for truncated BMP

<400> SEQUENCE: 75

```
gtggcggaaa acagcagcag cgatcagcgc caggcgtgca aaaaacatga actgtatgtg     60
agctttcgcg atctgggctg gcaggattgg attattgcgc cggaaggcta tgcggcgtat    120
tattgcgaag gcgaatgcgc gtttccgctg aacagctata tgaacgcgac caaccatgcg    180
attgtgcaga ccctggtgca ttttattaac ccggaaaccg tgccgaaacc gtgctgcgcg    240
ccgacccagc tgaacgcgat tagcgtgctg tattttgatg atagcagcaa cgtgattctg    300
```

```
aaaaaatatc gcaacatggt ggtgcgcgcg tgcggctgcc at                     342

<210> SEQ ID NO 76
<211> LENGTH: 327
<212> TYPE: DNA
<213> ORGANISM: artificial
<220> FEATURE:
<223> OTHER INFORMATION: nucleic acid sequence for truncated BMP

<400> SEQUENCE: 76
ggcaaaaaaa gccgcctgcg ctgcagcaaa aaaccgctgc atgtgaactt taaagaactg     60
ggctgggatg attggattat tgcgccgctg aatatgaag cgtatcattg cgaaggcgtg    120
tgcgattttc cgctgcgcag ccatctggaa ccgaccaacc atgcgattat tcagaccctg    180
atgaacagca tggatccggg cagcaccccg ccgagctgct gcgtgccgac caaactgacc    240
ccgattagca ttctgtatat tgatgcgggc aacaacgtgg tgtataaaca gtatgaagat    300
atggtggtgg aaagctgcgg ctgccgc                                        327

<210> SEQ ID NO 77
<211> LENGTH: 318
<212> TYPE: DNA
<213> ORGANISM: artificial
<220> FEATURE:
<223> OTHER INFORMATION: nucleic acid sequence for truncated BMP

<400> SEQUENCE: 77
ctgaaagcgc gctgcagccg caaagcgctg catgtgaact ttaaagatat gggctgggat     60
gattggatta ttgcgccgct ggaatatgaa gcgtttcatt gcgaaggcct gtgcgaattt    120
ccgctgcgca gccatctgga accgaccaac catgcggtga ttcagaccct gatgaacagc    180
atggatccgg aaagcacccc gccgacctgc tgcgtgccga cccgcctgag cccgattagc    240
attctgttta ttgatagcgc gaacaacgtg gtgtataaac agtatgaaga tatggtggtg    300
gaaagctgcg gctgccgc                                                 318
```